United States Patent
Saitoh et al.

(10) Patent No.: US 7,365,198 B2
(45) Date of Patent: Apr. 29, 2008

(54) SILYL COMPOUND, LIGHT EMITTING MATERIAL, AND ORGANIC LIGHT EMITTING DEVICE USING THE SAME

(75) Inventors: Akihito Saitoh, Yokohama (JP); Masataka Yashima, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 11/677,925

(22) Filed: Feb. 22, 2007

(65) Prior Publication Data
US 2007/0205715 A1    Sep. 6, 2007

(30) Foreign Application Priority Data
Mar. 2, 2006    (JP) .............................. 2006-056958

(51) Int. Cl.
*C07F 5/02*   (2006.01)
*C07F 5/04*   (2006.01)
*C07F 7/02*   (2006.01)

(52) U.S. Cl. .................... 544/229; 546/14; 548/406; 549/4; 556/413; 556/489

(58) Field of Classification Search ................ 556/400, 556/413, 489; 544/229; 546/14; 548/406; 549/4
See application file for complete search history.

(56) References Cited

U.S. PATENT DOCUMENTS

| | | | | |
|---|---|---|---|---|
| 5,187,310 | A | 2/1993 | Mishima et al. | 556/413 |
| 5,352,554 | A * | 10/1994 | Mishima et al. | 430/58.2 |
| 5,635,308 | A | 6/1997 | Inoue et al. | 428/690 |
| 5,759,444 | A | 6/1998 | Enokida et al. | 252/301.16 |
| 6,251,531 | B1 | 6/2001 | Enokida et al. | 428/690 |
| 6,713,192 | B2 | 3/2004 | Fukuoka et al. | 428/690 |
| 2006/0226768 | A1 * | 10/2006 | Yu et al. | 313/504 |

FOREIGN PATENT DOCUMENTS

| | | |
|---|---|---|
| JP | 03-008897 | 1/1991 |
| JP | 03-271296 | 12/1991 |
| JP | 08-012600 | 1/1996 |
| JP | 09-157643 | 6/1997 |
| JP | 10-072579 | 3/1998 |
| JP | 11-008068 | 1/1999 |
| JP | 11-040357 | 2/1999 |
| JP | 2001-284050 | 10/2001 |
| JP | 2004103463 | * 4/2004 |
| WO | WO 2005090365 | * 9/2005 |

OTHER PUBLICATIONS

Kyushin, et al., "Synthesis and . . . Disilylanthracenes"; Organometallics, vol. 15, 1667-1670 (1996).

* cited by examiner

*Primary Examiner*—Yvonne (Bonnie) Eyler
*Assistant Examiner*—Chukwuma O. Nwaonicha
(74) *Attorney, Agent, or Firm*—Fitzpatrick, Cella, Harper & Scinto

(57) ABSTRACT

Provided is an organic light emitting device capable of emitting light with high efficiency by incorporating a silyl compound in which a silyl group is directly bonded to an anthracene ring particularly into its light emitting layer. In the organic light emitting device including: a pair of electrodes formed of an anode and a cathode, at least one of which being transparent or semi-transparent; and one or more layers containing an organic compound layer interposed between the pair of electrodes, at least one of the layer containing the organic compound contains the following silyl compound, and a layer containing at least one kind of the silyl compound is a light emitting layer

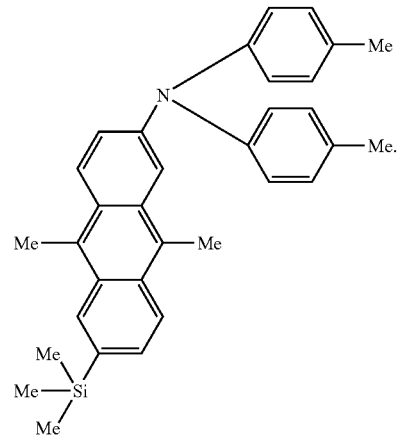

2 Claims, 4 Drawing Sheets

SILYL COMPOUND, LIGHT EMITTING MATERIAL, AND ORGANIC LIGHT EMITTING DEVICE USING THE SAME

BACKGROUND OF THE INVENTION

1. Field of the Invention

The present invention relates to a silyl compound, a light emitting material, and an organic light emitting device using the same.

2. Description of the Related Art

An organic light emitting device is a device which includes a thin film containing a fluorescent organic compound interposed between an anode and a cathode, which generates an exciton from the fluorescent compound by injection of an electron and a hole from each electrode, and which utilizes light to be irradiated when the exciton returns to a ground state.

Japanese Patent Application Laid-Open No. H08-12600 discloses a phenylanthracene derivative and an organic light emitting device using the derivative as examples of a material containing an anthracene ring and an organic light emitting device using the material. The document describes that, particularly when the derivative is used as a blue light emitting material or as an electron injecting or transporting material, a good organic film can be formed because the derivative has low crystallinity. However, none of the luminous efficiency and durable lifetime of the organic film is sufficient for practical use.

Japanese Patent Application Laid-Open No. H09-157643 and Japanese Patent Application Laid-Open No. H10-72579 disclose an aminoanthracene derivative and a diaminoanthracene derivative, respectively. The documents each describe that the use of each of the derivatives as a light emitting material can provide green light emission. However, the luminous efficiency of a device using each of the derivatives is low, and the durable lifetime of the device is not sufficient for practical use.

Japanese Patent No. 3,008,897 discloses a device using a specific bianthryl compound as a light emitting material, and describes that the device can emit light with high luminance. However, the document has no description concerning the luminous efficiency or durable lifetime of the device. Japanese Patent Application Laid-Open No. H11-8068 discloses a device using a specific anthracene compound containing an olefin site as a light emitting material, and describes that the device can emit light having a color ranging from a yellow color to a red color. However, the luminous efficiency of the device is not sufficient for practical use.

Japanese Patent Application Laid-Open No. 2001-284050 discloses a device containing an anthracene derivative with a specific structure, an electron transporting compound, and another fluorescent compound in a light emitting medium layer, to thereby provide a red light emitting device with improved reliability. However, the device has insufficient luminous efficiency for practical use.

Japanese Patent Application Laid-Open No. H03-271296 discloses an anthracene compound having a diarylamino group and a silyl group as a charge transport material in an electrophotographic photosensitive member. However, the document has no description concerning the application of the compound to an organic light emitting device.

SUMMARY OF THE INVENTION

The present invention has been made in view of solving problems in the conventional art, and an object of the present invention is therefore to provide an organic light emitting device exhibiting an optical output with high efficiency, high luminance, and a long lifetime. In addition, another object of the present invention is to provide an organic light emitting device which can be produced easily and at relatively low cost. Another object of the present invention is to provide a silyl compound for use in the light emitting layer of the organic light emitting device. Another object of the present invention is to provide a light emitting material formed of the silyl compound.

The inventors of the present invention have made extensive studies with a view to achieving the above-mentioned objects. As a result, they have completed the present invention.

(1) Therefore, the present invention provides a silyl compound represented by the following general formula (1):

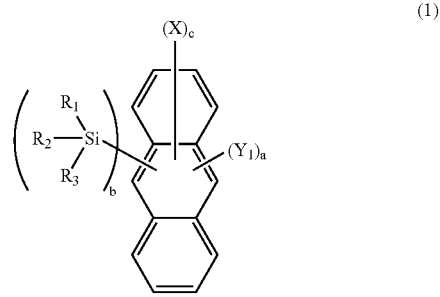

wherein $R_1$, $R_2$, and $R_3$ each represent a group selected from the group consisting of a hydrogen atom, a halogen atom, a substituted or unsubstituted alkyl group, a substituted or unsubstituted aralkyl group, a substituted or unsubstituted aryl group, and a substituted or unsubstituted heterocyclic group, and may be identical to or different from one another, X represents a group selected from the group consisting of a halogen atom, a substituted or unsubstituted alkyl group, a substituted or unsubstituted aralkyl group, a substituted or unsubstituted alkenyl group, a substituted or unsubstituted alkynyl group, a substituted or unsubstituted alkoxy group, a substituted or unsubstituted sulfide group, a substituted or unsubstituted silyl group, a substituted or unsubstituted amino group, a substituted or unsubstituted aryl group, and a substituted or unsubstituted heterocyclic group, and X's may be identical to or different from each other, $Y_1$ represents a substituted or unsubstituted amino group, a substituted or unsubstituted amino group linked by one group selected from the group consisting of an arylene group and a divalent heterocyclic group, a substituent formed of an aromatic fused polycyclic unit selected from naphthalene, phenanthrene, acenaphthylene, acephenanthrylene, aceanthrylene, triphenylene, pyrene, fluoranthene, chrysene, benzo[c]phenanthrene, naphthacene, dibenzo[a,c]anthracene, dibenzo[a,h]anthracene, dibenzo[b,def]chrysene, picene, perylene, and pentacene, or a substituent formed of a heterocyclic unit selected from substituted or unsubstituted pyridine, substituted or unsubstituted thiophene, substituted or unsubstituted quinoline, substituted or unsubstituted isoquinoline, substituted or unsubstituted quinoxaline, substituted or unsubstituted naphthyridine, substituted or unsubstituted quinazoline, substituted or unsubstituted phenanthridine, substituted or unsubstituted carbazole, substituted or unsubstituted benzothiophene, substituted or unsubstituted benzofuran, substituted or unsubstituted dibenzothiophene, substituted or unsubstituted dibenzofuran, substituted or unsubstituted acridine, and substituted or unsubstituted phenazine provided that, when $Y_1$ represents a substituted or unsubstituted amino group, an $R_1R_2R_3Si$—group substitutes at any one of 1- to 8-positions of an anthracene ring, and, furthermore, when X represents a substituted or unsubstituted silyl group, X substitutes at any one of 1- to 8-positions of the anthracene ring except a substitution site of the $R_1R_2R_3Si—$ group, a represents an integer of 1 or more to 3 or less, b represents an integer of 1 or more to 3 or less, and c represents an integer of 0 or more to 8 or less provided that a relationship of $a+b+c \leq 10$ is established.

(2) Further, the present invention provides the silyl compound according to the item (1), in which $Y_1$ represents a substituted or unsubstituted amino group, and the $R_1R_2R_3Si—$ group substitutes at any one of 1- to 8-positions of the anthracene ring.

(3) Further, the present invention provides the silyl compound according to the item (1), in which $Y_1$ is represented by the following general formula (3):

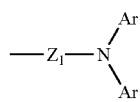

(3)

wherein $Z_1$ represents a group selected from the group consisting of an arylene group and a divalent heterocyclic group, $Ar_1$ and $Ar_2$ each represent a group selected from the group consisting of a substituted or unsubstituted alkyl group, a substituted or unsubstituted aralkyl group, a substituted or unsubstituted aryl group, and a substituted or unsubstituted heterocyclic group, and $Ar_1$ and $Ar_2$ may be identical to or different from each other.

(4) Further, the present invention provides the silyl compound according to the item (1), in which $Y_1$ represents a substituent formed of an aromatic fused polycyclic unit selected from naphthalene, phenanthrene, acenaphthylene, acephenanthrylene, aceanthrylene, triphenylene, pyrene, fluoranthene, chrysene, benzo[c]phenanthrene, naphthacene, dibenzo[a,c]anthracene, dibenzo[a,h]anthracene, dibenzo[b,def]chrysene, picene, perylene, and pentacene, or a substituent formed of a heterocyclic unit selected from substituted or unsubstituted pyridine, substituted or unsubstituted thiophene, substituted or unsubstituted quinoline, substituted or unsubstituted isoquinoline, substituted or unsubstituted quinoxaline, substituted or unsubstituted naphthyridine, substituted or unsubstituted quinazoline, substituted or unsubstituted phenanthridine, substituted or unsubstituted carbazole, substituted or unsubstituted benzothiophene, substituted or unsubstituted benzofuran, substituted or unsubstituted dibenzothiophene, substituted or unsubstituted dibenzofuran, substituted or unsubstituted acridine, and substituted or unsubstituted phenazine (5) Further, the present invention provides a silyl compound represented by the following general formula (2):

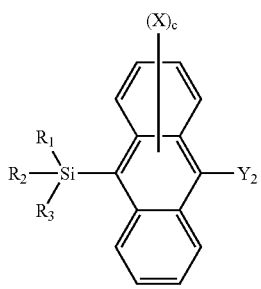

(2)

wherein $R_1$, $R_2$, and $R_3$ each represent a group selected from the group consisting of a hydrogen atom, a halogen atom, a substituted or unsubstituted alkyl group, a substituted or unsubstituted aralkyl group, a substituted or unsubstituted aryl group, and a substituted or unsubstituted heterocyclic group, and may be identical to or different from one another, X represents a group selected from the group consisting of a halogen atom, a substituted or unsubstituted alkyl group, a substituted or unsubstituted aralkyl group, a substituted or unsubstituted alkenyl group, a substituted or unsubstituted alkynyl group, a substituted or unsubstituted alkoxy group, a substituted or unsubstituted sulfide group, a substituted or unsubstituted silyl group, a substituted or unsubstituted amino group, a substituted or unsubstituted aryl group, and a substituted or unsubstituted heterocyclic group, and X's may be identical to or different from each other, $Y_2$ represents a substituted or unsubstituted amino group linked by one group selected from the group consisting of an arylene group and a divalent heterocyclic group, a substituent formed of an aromatic fused polycyclic unit selected from naphthalene, phenanthrene, acenaphthylene, acephenanthrylene, aceanthrylene, triphenylene, pyrene, fluoranthene, chrysene, benzo[c]phenanthrene, naphthacene, dibenzo[a,c]anthracene, dibenzo[a,h]anthracene, dibenzo[b,def]chrysene, picene, perylene, and pentacene, or a substituent formed of a heterocyclic unit selected from substituted or unsubstituted pyridine, substituted or unsubstituted thiophene, substituted or unsubstituted quinoline, substituted or unsubstituted isoquinoline, substituted or unsubstituted quinoxaline, substituted or unsubstituted naphthyridine, substituted or unsubstituted quinazoline, substituted or unsubstituted phenanthridine, substituted or unsubstituted carbazole, substituted or unsubstituted benzothiophene, substituted or unsubstituted benzofuran, substituted or unsubstituted dibenzothiophene, substituted or unsubstituted dibenzofuran, substituted or unsubstituted acridine, and substituted or unsubstituted phenazine, and c represents an integer of 0 or more to 8 or less.

(6) Further, the present invention provides the silyl compound according the item (5), in which $Y_2$ is represented by the following general formula (3):

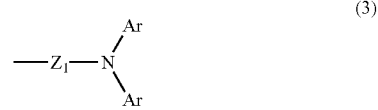

(3)

wherein $Z_1$ represents a group selected from the group consisting of an arylene group and a divalent heterocyclic group, $Ar_1$ and $Ar_2$ each represent a group selected from the group consisting of a substituted or unsubstituted alkyl group, a substituted or unsubstituted aralkyl group, a substituted or unsubstituted aryl group, and a substituted or unsubstituted heterocyclic group, and $Ar_1$ and $Ar_2$ may be identical to or different from each other.

(7) Further, the present invention provides an organic light emitting device, including:
a pair of electrodes formed of an anode and a cathode; and
an organic compound layer interposed between the pair of electrodes,
in which the organic compound layer contains the silyl compound according to the item (1).

(8) Further, the present invention provides an organic light emitting device, including:
a pair of electrodes formed of an anode and a cathode; and
an organic compound layer interposed between the pair of electrodes, in which the organic compound layer contains the silyl compound according to the item (5).

(9) Further, the present invention provides an organic light emitting device according the item (7), in which the organic compound layer is a light emitting layer.

(10) Further, the present invention provides the organic light emitting device according to the item (8), in which the organic compound layer is a light emitting layer.

(11) Further, the present invention provides the organic light emitting device according to the item (9), in which the light emitting layer contains a compound represented by the following general formula (4):

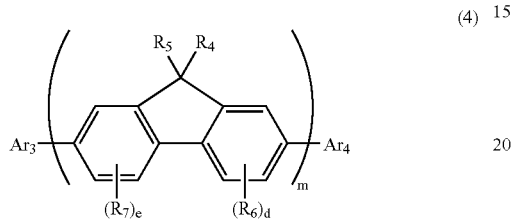

(4)

wherein $R_4$ and $R_5$ each represent a hydrogen atom, a substituted or unsubstituted alkyl group, a substituted or unsubstituted aralkyl group, a substituted or unsubstituted aryl group, or a substituted or unsubstituted heterocyclic group, and $R_4$ and $R_5$ may be identical to or different from each other, $R_6$ and $R_7$ each represent a substituted or unsubstituted alkyl group, a substituted or unsubstituted aralkyl group, a substituted or unsubstituted aryl group, a substituted or unsubstituted heterocyclic group, a substituted amino group, a cyano group, or a halogen atom, $R_6$ and $R_7$ may be identical to or different from each other, and $R_6$'s or $R_7$'s may be identical to or different from each other, $Ar_3$ and $Ar_4$ each represent a substituted or unsubstituted aryl group, or a substituted or unsubstituted heterocyclic group, and $Ar_3$ and $Ar_4$ may be identical to or different from each other, m represents an integer of 1 or more to 10 or less, and d and e each represent an integer of 0 or more to 3 or less.

(12) Further, the present invention provides the organic light emitting device according to the item (10), in which the light emitting layer contains a compound represented by the following general formula (4):

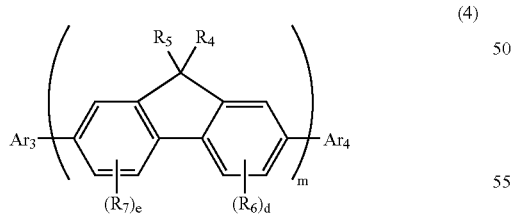

(4)

wherein $R_4$ and $R_5$ each represent a hydrogen atom, a substituted or unsubstituted alkyl group, a substituted or unsubstituted aralkyl group, a substituted or unsubstituted aryl group, or a substituted or unsubstituted heterocyclic group, and $R_4$ and $R_5$ may be identical to or different from each other, $R_6$ and $R_7$ each represent a substituted or unsubstituted alkyl group, a substituted or unsubstituted aralkyl group, a substituted or unsubstituted aryl group, a substituted or unsubstituted heterocyclic group, a substituted amino group, a cyano group, or a halogen atom, $R_6$ and $R_7$ may be identical to or different from each other, and $R_6$'s or $R_7$'s may be identical to or different from each other, $Ar_3$ and $Ar_4$ each represent a substituted or unsubstituted aryl group, or a substituted or unsubstituted heterocyclic group, and $Ar_3$ and $Ar_4$ may be identical to or different from each other, m represents an integer of 1 or more to 10 or less, and d and e each represent an integer of 0 or more to 3 or less.

(13) Further, the present invention provides the organic light emitting device according to the item (9), in which the light emitting layer contains a compound represented by the following general formula (5):

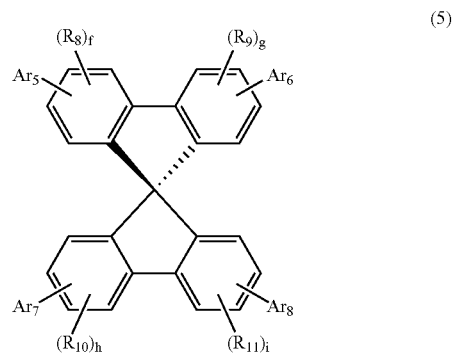

(5)

wherein $R_8$ to $R_{11}$ each represent a substituted or unsubstituted alkyl group, a substituted or unsubstituted aralkyl group, a substituted or unsubstituted aryl group, a substituted or unsubstituted heterocyclic group, a substituted amino group, a cyano group, or a halogen atom, $R_8$ to $R_{11}$ may be identical to or different from one another, and $R_8$'s, $R_9$'s, $R_{10}$'s, or $R_{11}$'s may be identical to or different from each other, $Ar_5$ to $Ar_8$ each represent a substituted or unsubstituted aryl group, or a substituted or unsubstituted heterocyclic group, and $Ar_5$ to $Ar_8$ may be identical to or different from one another, and f, g, h, and i each represent an integer of 0 or more to 3 or less.

(14) Further, the present invention provides the organic light emitting device according to the item (10), in which the light emitting layer contains a compound represented by the following general formula (5):

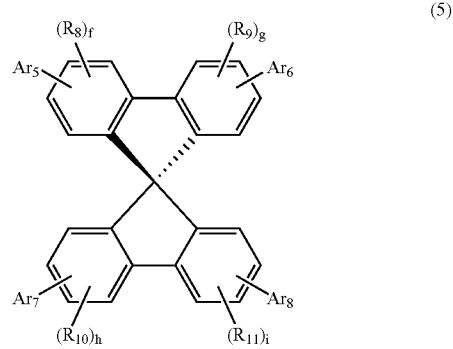

(5)

wherein $R_8$ to $R_{11}$ each represent a substituted or unsubstituted alkyl group, a substituted or unsubstituted aralkyl group, a substituted or unsubstituted aryl group, a substituted or unsubstituted heterocyclic group, a substituted amino group, a cyano group, or a halogen atom, $R_8$ to $R_{11}$ may be identical to or different from one another, and $R_8$'s, $R_9$'s, $R_{10}$'s, or $R_{11}$'s may be identical to or different from each other, $Ar_5$ to $Ar_8$ each represent a substituted or unsubstituted aryl group, or a substituted or unsubstituted heterocyclic group, and $Ar_5$ to $Ar_8$ may be identical to or different from one another, and f, g, h, and i each represent an integer of 0 or more to 3 or less.

(15) Further, the present invention provides the organic light emitting device according to the item (9), in which the light emitting layer contains a compound represented by the following general formula (6):

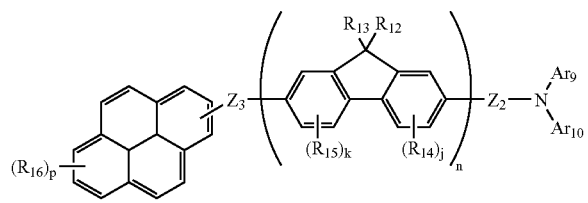

(6)

wherein $R_{12}$ and $R_{13}$ each represent a hydrogen atom, a substituted or unsubstituted alkyl group, a substituted or unsubstituted aralkyl group, a substituted or unsubstituted aryl group, or a substituted or unsubstituted heterocyclic group, and $R_{12}$ and $R_{13}$ may be identical to or different from each other, $R_{14}$ and $R_{15}$ each represent a substituted or unsubstituted alkyl group, a substituted or unsubstituted aralkyl group, a substituted or unsubstituted aryl group, a substituted or unsubstituted heterocyclic group, a substituted amino group, a cyano group, or a halogen atom, $R_{14}$ and $R_{15}$ may be identical to or different from each other, and $R_{14}$'s or $R_{15}$'s may be identical to or different from each other, $R_{16}$ represents a substituted or unsubstituted alkyl group, a substituted or unsubstituted aralkyl group, a substituted or unsubstituted aryl group, or a substituted or unsubstituted heterocyclic group, and $R_{16}$'s may be identical to or different from each other, $Z_2$ and $Z_3$ each represent a group selected from the group consisting of a direct single bond, a substituted or unsubstituted alkylene group, a substituted or unsubstituted alkenylene group, a substituted or unsubstituted alkynylene group, a substituted or unsubstituted aralkylene group, a substituted or unsubstituted arylene group, a substituted or unsubstituted divalent heterocyclic group, a substituted or unsubstituted silyl group, an ether group, a thioether group, and a carbonyl group, and each of $Z_1$ and $Z_2$ may further have a linking group, $Ar_9$ and $Ar_{10}$ each represent a substituted or unsubstituted aryl group, or a substituted or unsubstituted heterocyclic group, $Ar_9$ and $Ar_{10}$ may be identical to or different from each other, and $Ar_9$ and $Ar_{10}$ may form a ring, n represents an integer of 1 or more to 10 or less, j and k each represent an integer of 0 or more to 3 or less, and p represents an integer of 0 or more to 9 or less.

(16) Further, the present invention provides the organic light emitting device according to the item (10), in which the light emitting layer contains a compound represented by the following general formula (6):

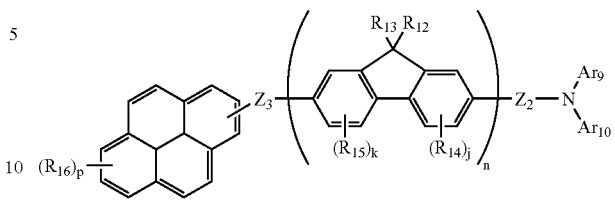

(6)

wherein $R_{12}$ and $R_{13}$ each represent a hydrogen atom, a substituted or unsubstituted alkyl group, a substituted or unsubstituted aralkyl group, a substituted or unsubstituted aryl group, or a substituted or unsubstituted heterocyclic group, and $R_{12}$ and $R_{13}$ may be identical to or different from each other, $R_{14}$ and $R_{15}$ each represent a substituted or unsubstituted alkyl group, a substituted or unsubstituted aralkyl group, a substituted or unsubstituted aryl group, a substituted or unsubstituted heterocyclic group, a substituted amino group, a cyano group, or a halogen atom, $R_{14}$ and $R_{15}$ may be identical to or different from each other, and $R_{14}$'s or $R_{15}$'s may be identical to or different from each other, $R_{16}$ represents a substituted or unsubstituted alkyl group, a substituted or unsubstituted aralkyl group, a substituted or unsubstituted aryl group, or a substituted or unsubstituted heterocyclic group, and $R_{16}$'s may be identical to or different from each other, $Z_2$ and $Z_3$ each represent a group selected from the group consisting of a direct single bond, a substituted or unsubstituted alkylene group, a substituted or unsubstituted alkenylene group, a substituted or unsubstituted alkynylene group, a substituted or unsubstituted aralkylene group, a substituted or unsubstituted arylene group, a substituted or unsubstituted divalent heterocyclic group, a substituted or unsubstituted silyl group, an ether group, a thioether group, and a carbonyl group, and each of $Z_1$ and $Z_2$ may further have a linking group, $Ar_9$ and $Ar_{10}$ each represent a substituted or unsubstituted aryl group, or a substituted or unsubstituted heterocyclic group, $Ar_9$ and $Ar_{10}$ may be identical to or different from each other, and $Ar_9$ and $Ar_{10}$ may form a ring, n represents an integer of 1 or more to 10 or less, j and k each represent an integer of 0 or more to 3 or less, and p represents an integer of 0 or more to 9 or less.

(17) Further, the present invention provides the organic light emitting device according the item (9), in which the light emitting layer contains a compound represented by the following general formula (7):

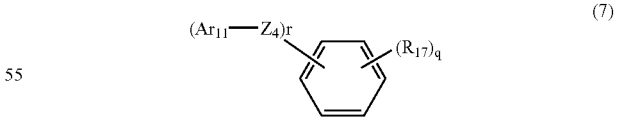

(7)

wherein $Ar_{11}$ represents a group selected from the group consisting of a substituted or unsubstituted aralkyl group, a substituted or unsubstituted aryl group, and a substituted or unsubstituted heterocyclic group, and, when r represents 2 or more, $Ar_{11}$'s may be identical to or different from each other, $Z_4$ represents a group selected from the group consisting of a direct single bond, a substituted or unsubstituted alkylene group, a substituted or unsubstituted alkenylene group, a substituted or unsubstituted alkynylene group, a substituted or unsubstituted aralkylene group, a substituted or unsubstituted arylene group, a substituted or unsubstituted, divalent heterocyclic group, a substituted or unsubstituted silyl group, an ether group, a thioether group, and a carbonyl group, $Z_3$ may further have a linking group, and, when r represents 2 or more, $Z_3$'s may be identical to or different from each other, $R_{17}$ represents a group selected from the group consisting of a halogen atom, a substituted or unsubstituted alkyl group, a substituted or unsubstituted alkoxy group, a substituted or unsubstituted sulfide group, a substituted or unsubstituted amino group, and a substituted or unsubstituted silyl group, and, when q represents 2 or more, $R_{17}$'s may be identical to or different from each other, r represents an integer of 1 or more to 6 or less, and q represents an integer of 0 or more to 5 or less provided that a relationship of $q+r \leq 6$ is satisfied.

(18) Further, the present invention provides the organic light emitting device according to the item (10), in which the light emitting layer contains a compound represented by the following general formula (7):

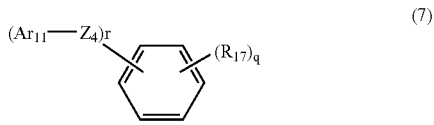

(7)

wherein $Ar_{11}$ represents a group selected from the group consisting of a substituted or unsubstituted aralkyl group, a substituted or unsubstituted aryl group, and a substituted or unsubstituted heterocyclic group, and, when r represents 2 or more, $Ar_{11}$'s may be identical to or different from each other, $Z_4$ represents a group selected from the group consisting of a direct single bond, a substituted or unsubstituted alkylene group, a substituted or unsubstituted alkenylene group, a substituted or unsubstituted alkynylene group, a substituted or unsubstituted aralkylene group, a substituted or unsubstituted arylene group, a substituted or unsubstituted, divalent heterocyclic group, a substituted or unsubstituted silyl group, an ether group, a thioether group, and a carbonyl group, $Z_3$ may further have a linking group, and, when r represents 2 or more, $Z_3$'s may be identical to or different from each other, $R_{17}$ represents a group selected from the group consisting of a halogen atom, a substituted or unsubstituted alkyl group, a substituted or unsubstituted alkoxy group, a substituted or unsubstituted sulfide group, a substituted or unsubstituted amino group, and a substituted or unsubstituted silyl group, and, when q represents 2 or more, $R_{17}$'s may be identical to or different from each other, r represents an integer of 1 or more to 6 or less, and q represents an integer of 0 or more to 5 or less provided that a relationship of $q+r \leq 6$ is satisfied.

The incorporation of a silyl compound in which a silyl group is directly bonded to an anthracene ring particularly into the light emitting layer of the organic light emitting device of the present invention enables the device to emit light with high efficiency. The organic light emitting device of the present invention emits light with high efficiency at a low applied voltage, and is excellent in durability. Further, there can be provided a light emitting material consisting of the silyl compound.

Further features of the present invention will become apparent from the following description of exemplary embodiments with reference to the attached drawings.

DESCRIPTION OF THE EMBODIMENTS

Figure 1:
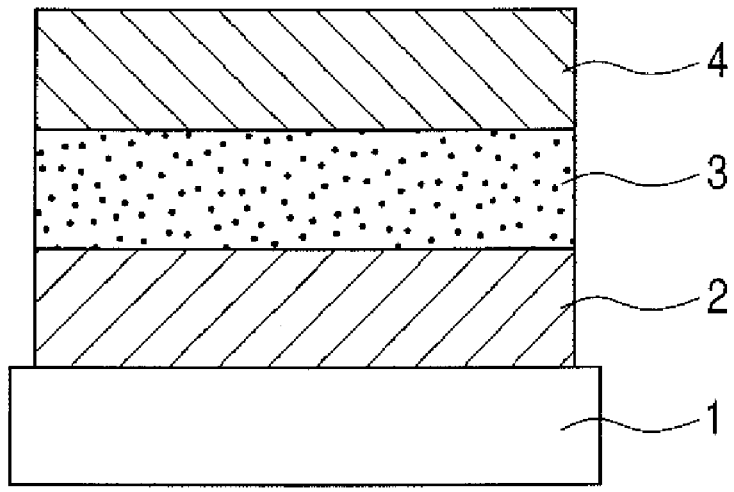
FIG. 1 is a sectional view illustrating an example of an organic light emitting device according to the present invention.

Hereinafter, the present invention will be described in detail.

First, description will be given of a silyl compound represented by the following general formula (1) to be incorporated into an organic compound layer interposed between a pair of electrodes formed of an anode and a cathode in an organic light emitting device of the present invention. Particular examples of an organic compound layer using a silyl compound of the present invention include a light emitting layer, an electron injecting or transporting layer, and a hole injecting or transporting layer.

The silyl compound represented by the general formula (1) to be used in the present invention can be used as a material for an organic light emitting device in one or more layers each containing an organic compound. The silyl compound may be used alone, or may be mixed with a compound represented by any one of the general formulae (4) to (7) before use. When the silyl compound is mixed with the compound represented by any one of the general formulae (4) to (7) before use, the content of the silyl compound is desirably in the range of 0.01 wt % or more to 80 wt % or less, or preferably 1 wt % or more to 40 wt % or less with respect to the total of the silyl compound and the compound represented by any one of the general formulae (4) to (7).

When the silyl compound of the present invention is used for a light emitting layer, for example, the compound can be used alone in the light emitting layer, and can be used to serve as a dopant (guest) material or a host material, whereby a device having a high color purity, high emission efficiency, and a long lifetime can be obtained.

When the silyl compound is used as a dopant material in the organic light emitting device of the present invention, a dopant concentration with respect to the host material is 0.01 wt % or more to 80 wt % or less, or preferably 1 wt % or more to 40 wt % or less. The dopant material may be incorporated into the entirety of a layer formed of the host material uniformly or with a concentration gradient. Alternatively, the dopant material may be incorporated into a certain region of the host material layer partially so that a region of the host material layer containing no dopant material is present. It should be noted that, when the silyl compound of the present invention is used for a light emitting layer, the dopant material and the host material each refer to a material for constituting a light emitting layer 3 in an organic light emitting device illustrated in each of FIGS. 1 to 5.

The silyl compound to be used in the present invention is of a structure in which a silyl group is directly bonded to an anthracene ring, whereby the compound has realized an improvement in fluorescent quantum efficiency, that is, highly efficient light emission in an organic light emitting device. "Organometallics" 1996, 15, 1067-1070 describes an effect of the introduction of a silyl group into anthracene on an improvement in fluorescent quantum efficiency. In the present invention, various substituents as well as a silyl group have been introduced into an anthracene ring in consideration of, for example, an additional improvement in quantum efficiency, the adjustment of a luminescent color, and the mobility of a carrier. In the present invention, based on the foregoing consideration, a material for an organic light emitting device formed of one or more layers each containing an organic compound, the one or more layers being interposed between a pair of electrodes formed of an anode and a cathode, has been mainly designed. The use of the organic compound mainly in a light emitting layer has provided an organic light emitting device having high efficiency and a long lifetime.

In each of the general formulae (1) to (7), a hydrogen atom that constitutes any one of a hydrogen atom group and the following substituents may be substituted by a deuterium atom.

Examples of a substituted or unsubstituted alkyl group in the general formulae (1) to (7) include, but are not limited to: a methyl group; a methyl-d1 group; a methyl-d3 group; an ethyl group; an ethyl-d5 group; an n-propyl group; an n-butyl group; an n-pentyl group; an n-hexyl group; an n-heptyl group; an n-octyl group; an n-decyl group; an iso-propyl group; an iso-propyl-d7 group; an iso-butyl group; a sec-butyl group; a tert-butyl group; a tert-butyl-d9 group; an iso-pentyl group; a neopentyl group; a tert-octyl group; a fluoromethyl group; a difluoromethyl group; a trifluoromethyl group; a 2-fluoroethyl group; a 2,2,2-trifluoroethyl group; a perfluoroethyl group; a 3-fluoropropyl group; a perfluoropropyl group; a 4-fluorobutyl group; a perfluorobutyl group; a 5-fluoropentyl group; a 6-fluorohexyl group; a chloromethyl group; a trichloromethyl group; 2-chloroethyl group; a 2,2,2-trichloroethyl group; a 4-chlorobutyl group; a 5-chloropentyl group; a 6-chlorohexyl group; a bromomethyl group; a 2-bromoethyl group; an iodomethyl group; a 2-iodoethyl group; a hydroxymethyl group; a hydroxyethyl group; a cyclopropyl group; a cyclobutyl group; a cyclopentyl group; a cyclohexyl group; a cyclopentylmethyl group; a cyclohexylmethyl group; a cyclohexylethyl group; a 4-fluorocyclohexyl group; a norbornyl group; and an adamantyl group. Note that d1 of the methyl-d1 group indicates that one of the hydrogen atoms of the methyl group is substituted by one deuterium atom.

Examples of a substituted or unsubstituted aralkyl group include, but are not limited to: a benzyl group; a 2-phenylethyl group; a 2-phenylisopropyl group; a 1-naphthylmethyl group; a 2-naphthylmethyl group; a 2-(1-napthyl)ethyl group; a 2-(2-napthyl)ethyl group; a 9-anthrylmethyl group; a 2-(9-anthryl)ethyl group; a 2-fluorobenzyl group; a 3-fluorobenzyl group; a 4-fluorobenzyl group; a 2-chlorobenzyl group; a 3-chlorobenzyl group; a 4-chlorobenzyl group; a 2-bromobenzyl group; a 3-bromobenzyl group; and a 4-bromobenzyl group.

Examples of a substituted or unsubstituted alkenyl group include, but are not limited to: a vinyl group; an allyl group (a 2-propenyl group); a 1-propenyl group; an iso-propenyl group; a 1-butenyl group; a 2-butenyl group; a 3-butenyl group; and a styryl group.

Examples of a substituted or unsubstituted alkynyl group include, but are not limited to: an acetylenyl group; a phenylacetylenyl group; and a 1-propynyl group.

Examples of a substituted or unsubstituted aryl group include, but are not limited to: a phenyl group; a phenyl-d5 group; a 4-methylphenyl group; a 4-methoxyphenyl group; a 4-ethylphenyl group; a 4-fluorophenyl group; a 4-trifluorophenyl group; a 3,5-dimethylphenyl group; a 2,6-diethylphenyl group; a mesityl group; a 4-tert-butylphenyl group; a ditolylaminophenyl group; a biphenyl group; a terphenyl group; a naphthyl group; a naphthyl-d7 group; an acenaphthylenyl group; an anthryl group; an anthryl-d9 group; a phenanthryl group; a phenanthryl-d9 group; a pyrenyl group; a pyrenyl-d9 group; an acephenanthrylenyl group; an aceanthrylenyl group; a chrysenyl group; a dibenzo chrysenyl group; a benzoanthryl group; a benzoanthryl-d11 group; a dibenzoanthryl group; a naphthacenyl group; a picenyl group; a pentacenyl group; a fluorenyl group; a triphenylenyl group; a perylenyl group; and a perylenyl-d11 group.

Examples of a substituted or unsubstituted heterocyclic group include, but are not limited to: a pyrrolyl group; a pyridyl group; a pyridyl-d5 group; a bipyridyl group; a methylpyridyl group; a pyrimidinyl group; a pyrazinyl group; a pyridazinyl group; a terpyrrolyl group; a thienyl group; a thienyl-d4 group; a terthienyl group; a propylthienyl group; a benzothienyl group; a dibenzothienyl group; a dibenzothienyl-d7 group; a furyl group; a furyl-d4 group; a benzofuryl group; an isobenzofuryl group; dibenzofuryl group; a dibenzofuryl-d7 group; a quinolyl group; a quinolyl-d6 group; an isoquinolyl group; a quinoxalinyl group; a naphthylidinyl group; a quinazolinyl group; a phenanthridinyl group; an indolizinyl group; a phenazinyl group; a carbazolyl group; an oxazolyl group; an oxadiazolyl group; a thiazolyl group; a thiadiazolyl group; an acridinyl group; and a phenazinyl group.

In a substituted or unsubstituted amino (—NR'R") group, examples of R' and R" include, but are not limited to: a hydrogen atom; a deuterium atom; the above-mentioned substituted or unsubstituted alkyl group, aralkyl group, aryl group, or heterocyclic group; an alkyl group, alkenyl group, alkynyl group, aralkyl group, or amino group bonded through a substituted or unsubstituted arylene group or divalent heterocyclic group; a silyl group; an ether group; a thioether group; and a carbonyl group. Examples of the substituted or unsubstituted amino group include, but are not limited to: an amino group; an N-methylamino group; an N-ethylamino group; an N,N-dimethylamino group; an N,N-diethylamino group; an N-methyl-N-ethylamino group; an N-benzylamino group; an N-methyl-N-benzylamino group; an N,N-dibenzylamino group; an anilino group; an N,N-diphenylamino group; an N-phenyl-N-tolylamino group; an N,N-ditolylamino group; an N-methyl-N-phenylamino group; an N,N-dianisolylamino group; an N-mesityl-N-phenylamino group; an N,N-dimesitylamino group; an N-phenyl-N-(4-tert-butylphenyl)amino group; and an N-phenyl-N-(4-trifluoromethylphenyl)amino group.

Examples of a substituted or unsubstituted alkoxy group include: an alkyloxy group or aralkyloxy group having the above-mentioned substituted or unsubstituted alkyl group or aralkyl group; and an aryloxy group having the above-mentioned substituted or unsubstituted aryl group or heterocyclic group. Specific examples thereof include, but are not limited to: a methoxy group; an ethoxy group; a propoxy group; a 2-ethyl-octyloxy group; a phenoxy group; a 4-tert-butylphenoxy group; a benzyloxy group; and a thienyloxy group.

Examples of a substituted or unsubstituted sulfide group include: an alkylsulfide group or aralkylsulfide group having the above-mentioned substituted or unsubstituted alkyl group or aralkyl group; and an arylsulfide group having the above-mentioned substituted or unsubstituted aryl group or heterocyclic group. Specific examples thereof include, but are not limited to: a methylsulfide group; an ethylsulfide group; a phenylsulfide group; and a 4-methylphenylsulfide group.

Examples of the substituted or unsubstituted silyl group include, but are not limited to, a trimethylsilyl group, a triethylsilyl group, a tert-butyldimethylsilyl group, an iso-propyldimethylsilyl group, a triphenylsilyl group, a phenyldimethylsilyl group, a mesityldimethylsilyl group, and a dimesitylmethylsilyl group.

Examples of the substituted or unsubstituted alkylene group include, but are not limited to, a methylene group, an ethylene group, a propylene group, a 2-methylpropylene group, a fluoromethylene group, a difluoromethylene group, a bromomethylene group, and a bromoethylene group.

Examples of a substituted or unsubstituted aralkylene group include, but are not limited to: a benzylene group; a 2-phenylethylene group; a 2-phenylisopropylene group; a 1-naphthylmethylene group; a 2-naphthylmethylene group; a 9-anthrylmethylene group; a 2-fluorobenzylene group; a 3-fluorobenzylene group; a 4-fluorobenzylene group; a 4-chlorobenzylene group; and a 4-bromobenzylene group.

Examples of a substituted or unsubstituted alkenylene group include, but are not limited to: a vinylene group; an iso-propenylene group; a styrylene group; and a 1,2-diphenylvinylene group.

Examples of a substituted or unsubstituted alkynylene group include, but are not limited to, an acetylenylene group and a phenyl acetylenylene group.

Examples of a substituted or unsubstituted arylene group include, but are not limited to: a phenylene group; a biphenylene group; a tetrafluorophenylene group; a dimethylphenylene group; a naphthylene group; a phenanthrylene group; a pyrenylene group; a tetracenylene group; a pentacenylene group; and a perylenylene group.

Examples of a substituted or unsubstituted divalent heterocyclic group include, but are not limited to: a furylene group; a pyrrolylene group; a pyridylene group; a terpyridylene group; a thienylene group; a terthienylene group; an oxazolylene group; a thiazolylene group; and a carbazolylene group.

Examples of the linking group include, but are not limited to, the substituted or unsubstituted alkylene group, the substituted or unsubstituted alkenylene group, the substituted or unsubstituted alkynylene group, the substituted or unsubstituted aralkylene group, the substituted or unsubstituted arylene group, and the substituted or unsubstituted divalent heterocyclic group.

Examples of a substituent which may further be included in the above-mentioned substituents include, but are not limited to: a deuterium atom; an alkyl group or aralkyl group such as a methyl group, an ethyl group, an n-propyl group, an n-butyl group, an n-pentyl group, an n-hexyl group, an n-heptyl group, an n-octyl group, an n-decyl group, an iso-propyl group, an iso-butyl group, a sec-butyl group, a tert-butyl group, an iso-pentyl group, a neopentyl group, a tert-octyl group, a benzyl group, or a 2-phenylethyl group; an alkoxy group such as a methoxy group, an ethoxy group, a propoxy group, a 2-ethyl-octyloxy group, a phenoxy group, a 4-tert-butylphenoxy group, or a benzyloxy group; an aryl group such as a phenyl group, a 4-methylphenyl group, a 4-ethylphenyl group, a 3-chlorophenyl group, a 3,5-dimethylphenyl group, a triphenylamino group, a biphenyl group, a terphenyl group, a naphthyl group, an anthryl group, a phenanthryl group, or a pyrenyl group; a heterocyclic group such as a pyridyl group, a bipyridyl group, a methylpyridyl group, a thienyl group, a terthienyl group, a propylthienyl group, a furyl group, a quinolyl group, a carbazolyl group, or an N-ethylcarbazolyl group; a halogen group; a hydroxyl group; a cyano group; and a nitro group.

The general formula of the silyl compound of the present invention will be further specifically exemplified. One example is a compound characterized in that $Y_1$ of the general formula (1) represents a substituted or unsubstituted amino group, and a silyl group substitutes at any one of 1- to 8-positions of an anthracene ring. Another example is a silyl compound characterized in that $Y_1$ of the general formula (1) or $Y_2$ of the general formula (2) is represented by the following general formula (3), and $Z_1$ is a group selected from the group consisting of an arylene group and a divalent heterocyclic group:

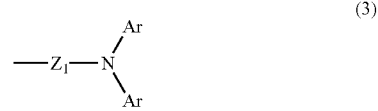

(3)

wherein $Z_1$ represents a group selected from the group consisting of an arylene group and a divalent heterocyclic group, $Ar_1$ and $Ar_2$ each represent a group selected from the group consisting of a substituted or unsubstituted alkyl group, a substituted or unsubstituted aralkyl group, a substituted or unsubstituted aryl group, and a substituted or unsubstituted heterocyclic group, and $Ar_1$ and $Ar_2$ may be identical to or different from each other.

Another example is a silyl compound characterized in that $Y_1$ of the general formula (1) represents a substituent formed of an aromatic fused polycyclic unit selected from naphthalene, phenanthrene, acenaphthylene, acephenanthrylene, aceanthrylene, triphenylene, pyrene, fluoranthene, chrysene, benzo[c]phenanthrene, naphthacene, dibenzo[a,c]anthracene, dibenzo[a,h]anthracene, dibenzo[b,def]chrysene, picene, perylene, and pentacene, or a substituent formed of a heterocyclic unit selected from substituted or unsubstituted pyridine, substituted or unsubstituted thiophene, substituted or unsubstituted quinoline, substituted or unsubstituted isoquinoline, substituted or unsubstituted quinoxaline, substituted or unsubstituted naphthyridine, substituted or unsubstituted quinazoline, substituted or unsubstituted phenanthridine, substituted or unsubstituted carbazole, substituted or unsubstituted benzothiophene, substituted or unsubstituted benzofuran, substituted or unsubstituted dibenzothiophene, substituted or unsubstituted dibenzofuran, substituted or unsubstituted acridine, and substituted or unsubstituted phenazine.

In addition, a second compound for use in the light emitting layer will be further exemplified. Examples of the compound include the following general formulae (4) to (7).

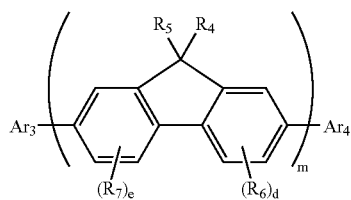
(4)
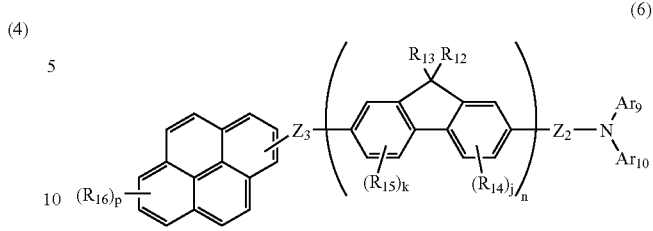
(6)
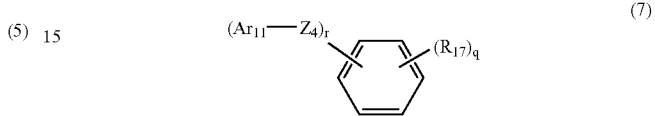
(5)
(7)
Further, specific compounds to be used in the present invention are shown below. However, the present invention is not limited to those compounds.
It should be noted that Me represents a methyl group, tBu represents a tert-butyl group, D represents a deuterium group, Ph represents a phenyl group, and Et represents an ethyl group.
General Formulae (1), (2)
| Compound No. | A | A—B—C B | C |
|---|---|---|---|
| 101 | | | |
| 102 | | | |
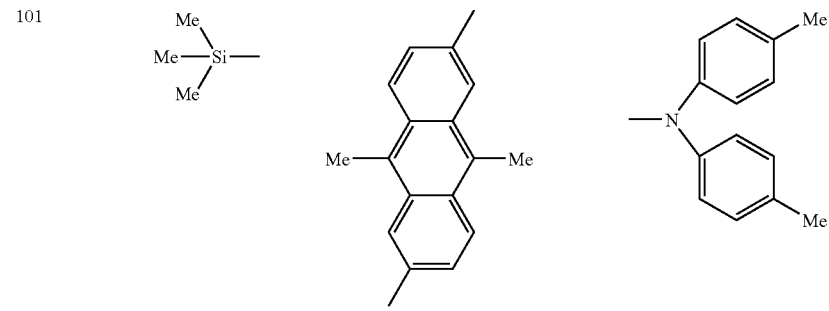
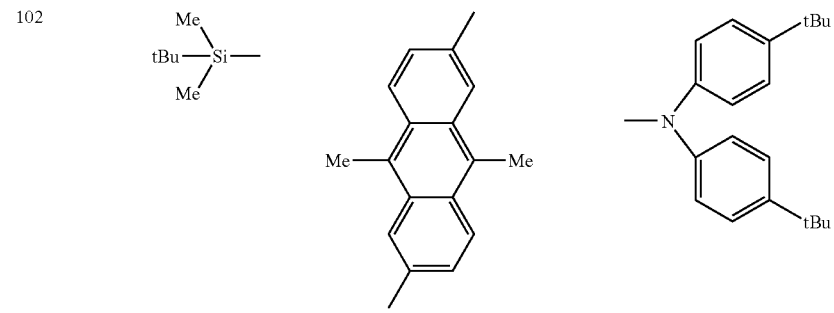

-continued
| Compound No. | A | B | C |
|---|---|---|---|
| 103 | 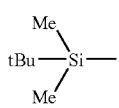 | 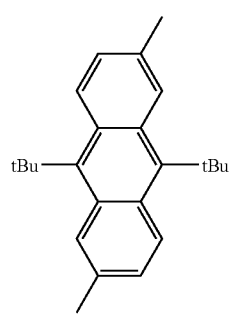 | 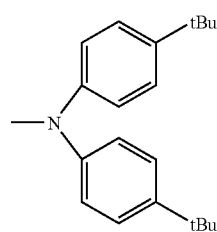 |
| 104 | 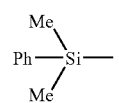 | 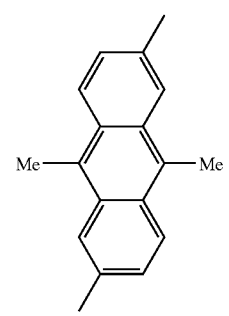 | 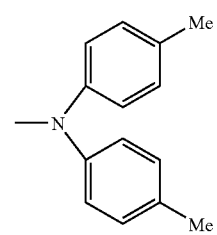 |
| 105 | 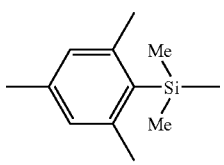 | 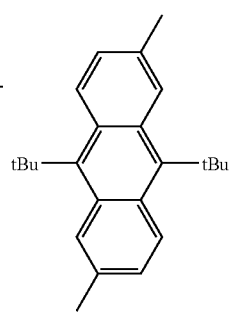 | 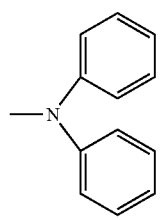 |
| 106 | 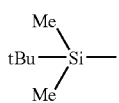 | 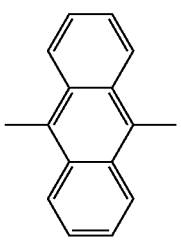 | 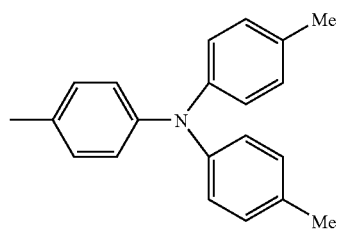 |
| 107 | 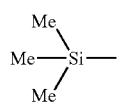 | 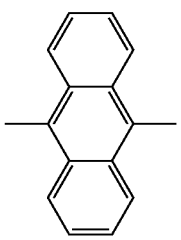 | 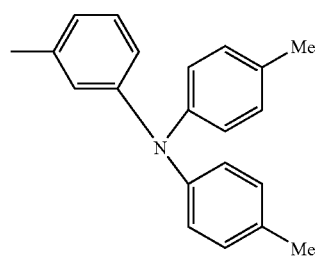 |

-continued
| Compound No. | A | B | C |
|---|---|---|---|
| 108 | 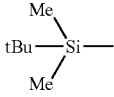 | 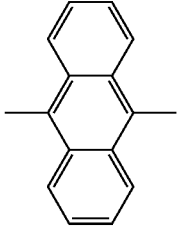 | 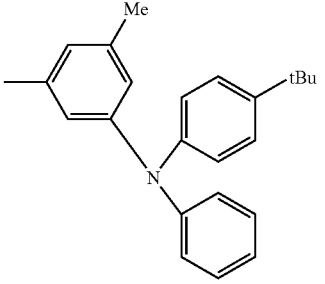 |
| 109 | 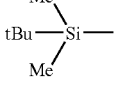 | 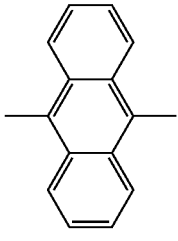 | 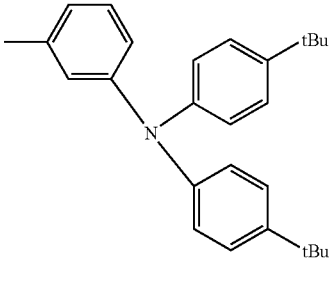 |
| 110 | 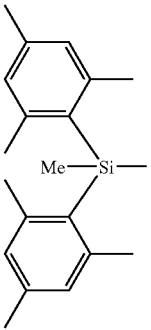 | 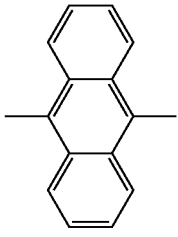 | 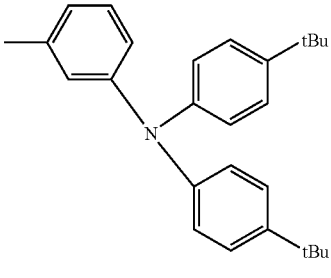 |
| 111 | 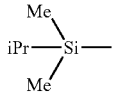 | 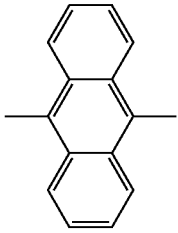 | 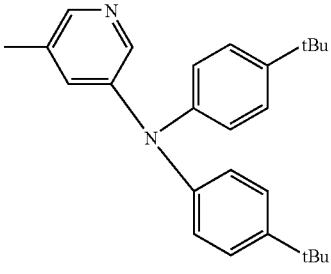 |
| 112 | 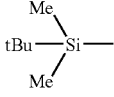 | 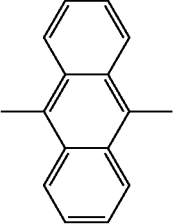 | 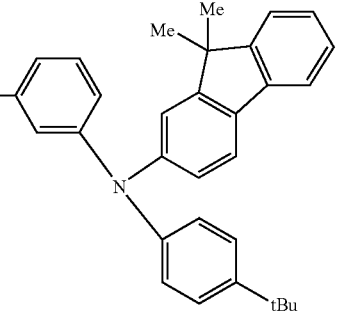 |

-continued
| Compound No. | A | B | C |
|---|---|---|---|
| 113 | 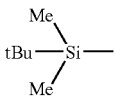 | 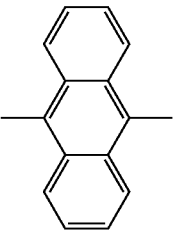 | 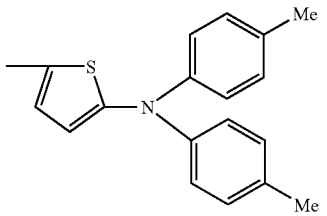 |
| 114 | 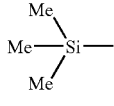 | 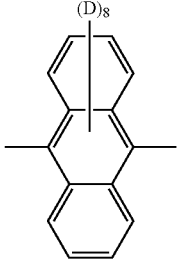 | 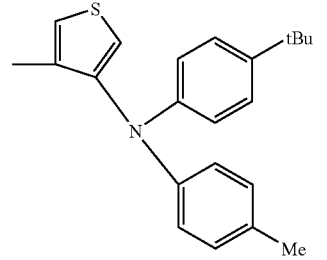 |
| 115 | 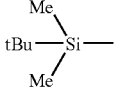 | 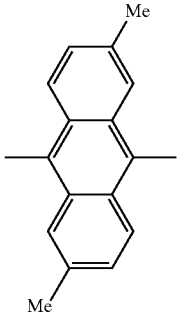 | 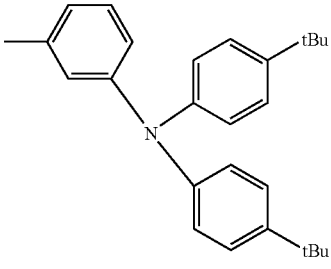 |
| 116 | 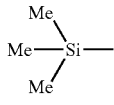 | 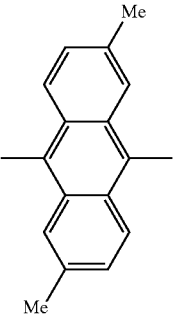 | 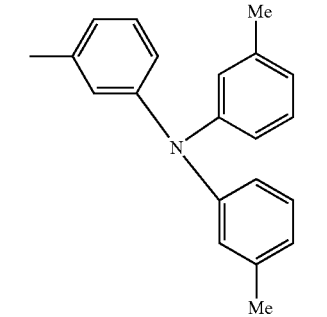 |
| 117 | 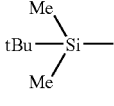 | 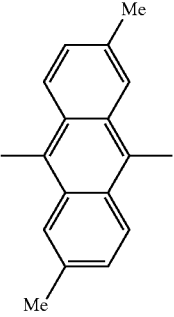 | 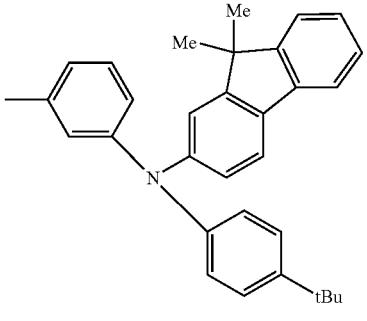 |

-continued
| Compound No. | A | B | C |
|---|---|---|---|
| 118 | 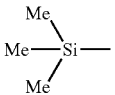 | 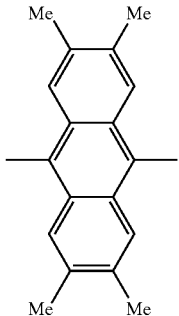 | 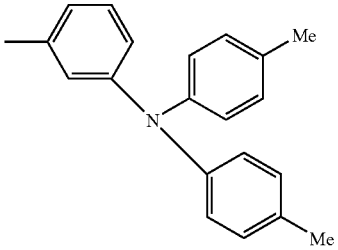 |
| 119 | 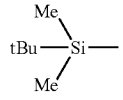 | 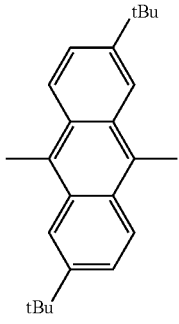 | 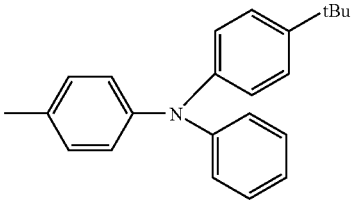 |
| 120 | 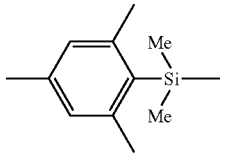 | 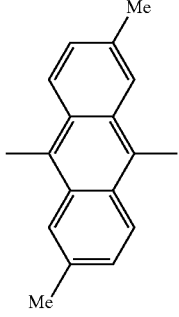 | 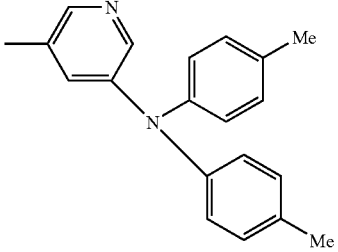 |
| 121 | 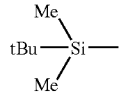 | 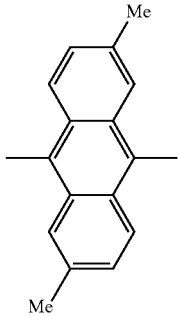 | 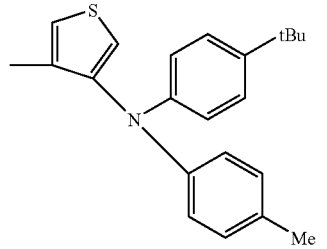 |
| 122 | 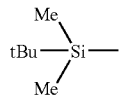 | 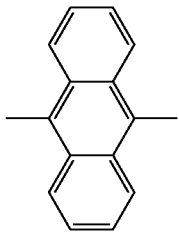 | 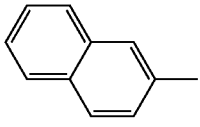 |

-continued

| Compound No. | A | B | C |
|---|---|---|---|
| 123 | Me, iPr—Si—, Me | 9,10-anthracenediyl | 1-naphthyl |
| 124 | Me, tBu—Si—, Me | 9,10-anthracenediyl | phenanthrenyl |
| 125 | Me, tBu—Si—, Me | 9,10-anthracenediyl | phenanthrenyl |
| 126 | Me, tBu—Si—, Me | 9,10-anthracenediyl | (D)$_9$ pyrenyl |
| 127 | Me, Me—Si—, Me | 9,10-anthracenediyl | tBu,Me-pyrenyl |
| 128 | Me, tBu—Si—, Me | 9,10-anthracenediyl | fluoranthenyl |

-continued
| Compound No. | A | B | C |
|---|---|---|---|
| 129 | 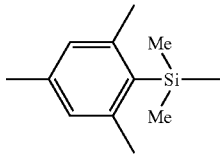 | 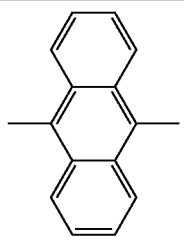 | 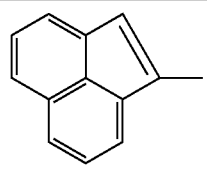 |
| 130 | 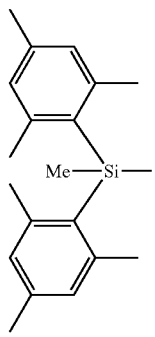 | 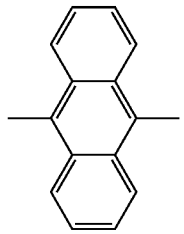 | 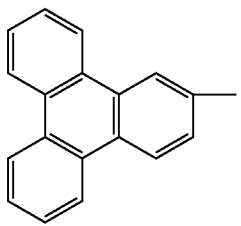 |
| 131 | 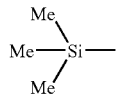 | 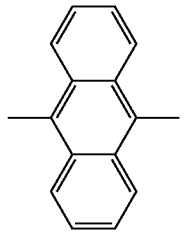 | 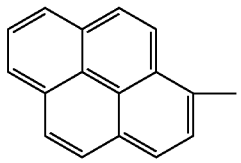 |
| 132 | 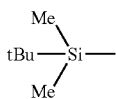 | 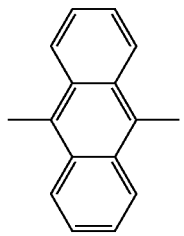 | 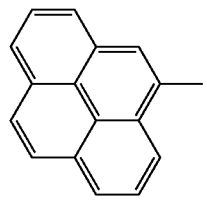 |
| 133 | 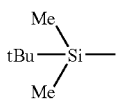 | 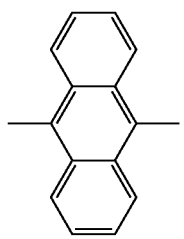 | 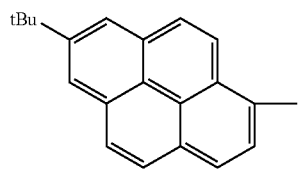 |
| 134 | 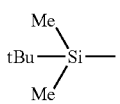 | 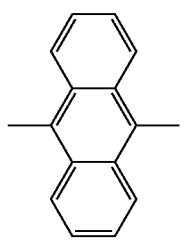 | 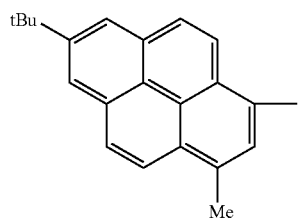 |

-continued
| Compound No. | A | B | C |
|---|---|---|---|
| 135 | 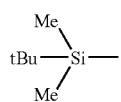 | 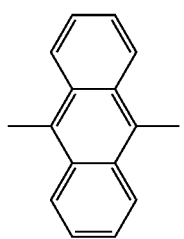 | 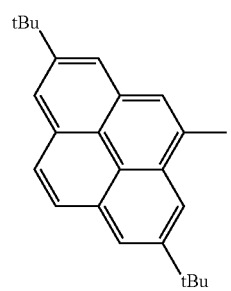 |
| 136 | 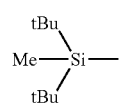 | 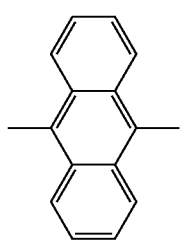 | 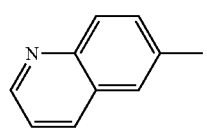 |
| 137 | 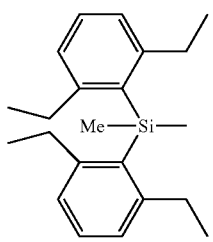 | 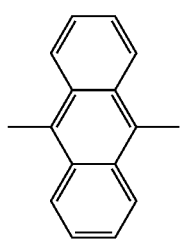 | 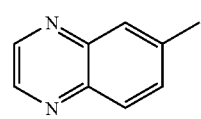 |
| 138 | 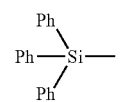 | 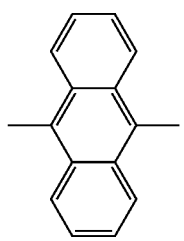 | 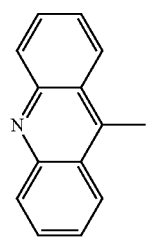 |
| 139 | 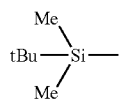 | 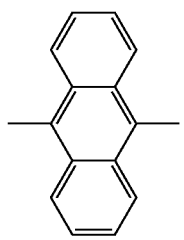 | 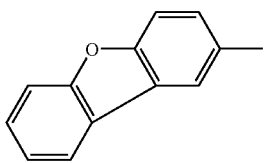 |
| 140 | 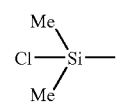 | 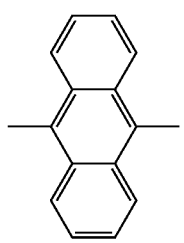 | 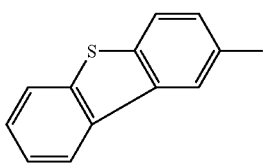 |

-continued
| Compound No. | A | B | C |
|---|---|---|---|
| 141 | 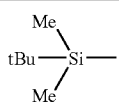 | 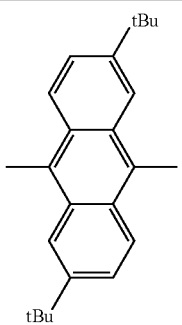 | 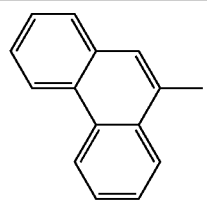 |
| 142 | 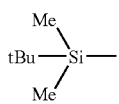 | 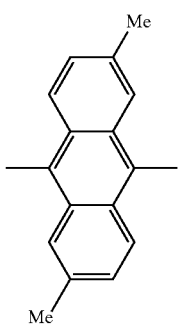 | 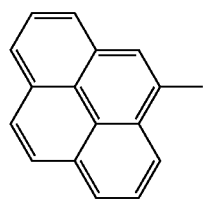 |
| 143 | 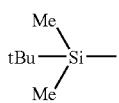 | 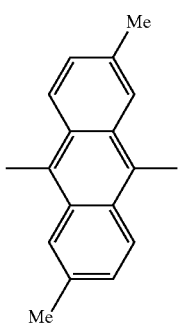 | 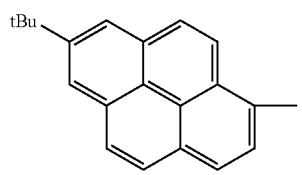 |
| 144 | 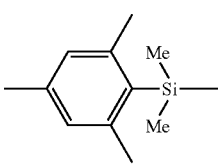 | 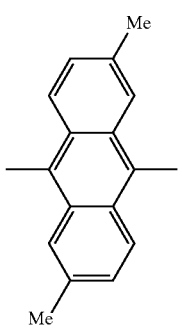 | 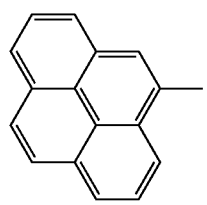 |

-continued
| Compound No. | A | B | C |
|---|---|---|---|
| 145 | 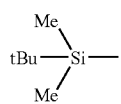 | 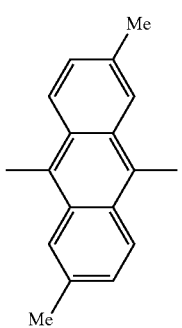 | 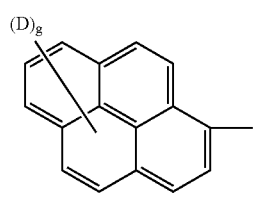 |
| 146 | 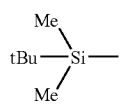 | 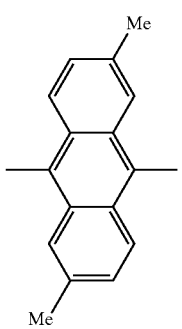 | 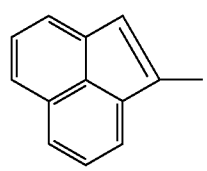 |
| 147 | 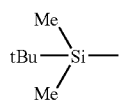 | 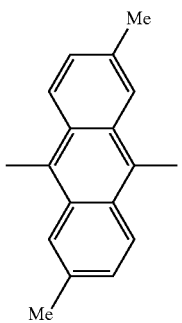 | 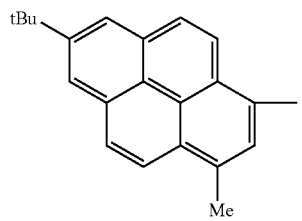 |
| 148 | 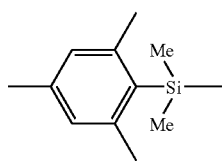 | 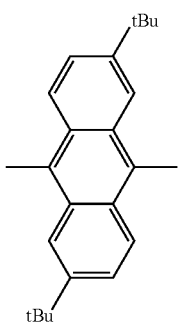 | 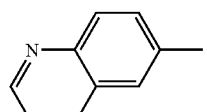 |

-continued
| Compound No. | A | B | C |
|---|---|---|---|
| 149 | 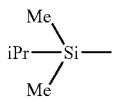 | 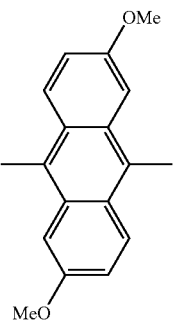 | 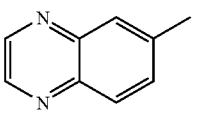 |
| 150 | 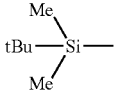 | 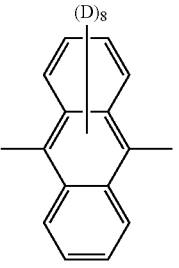 | 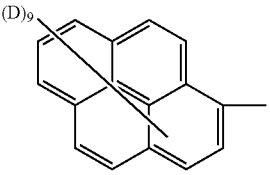 |
| 151 | 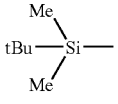 | 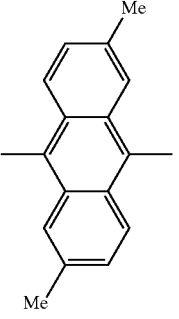 | 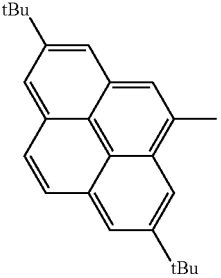 |
General Formula (4)
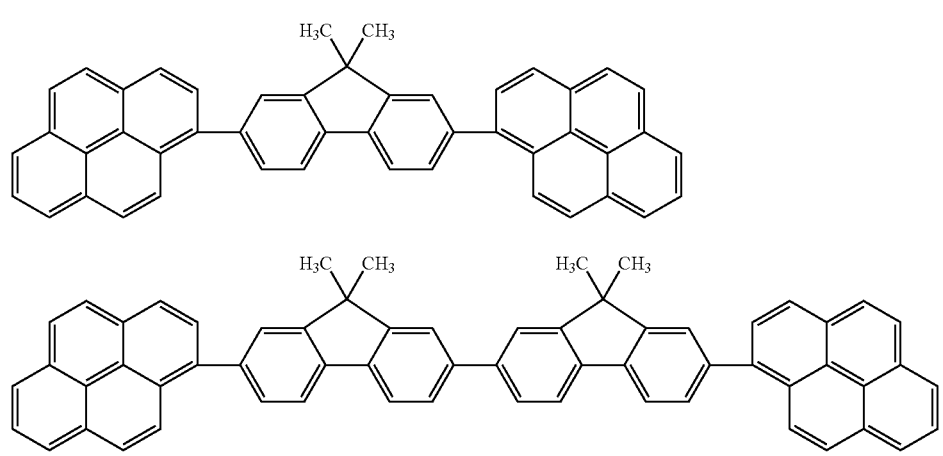
201
202

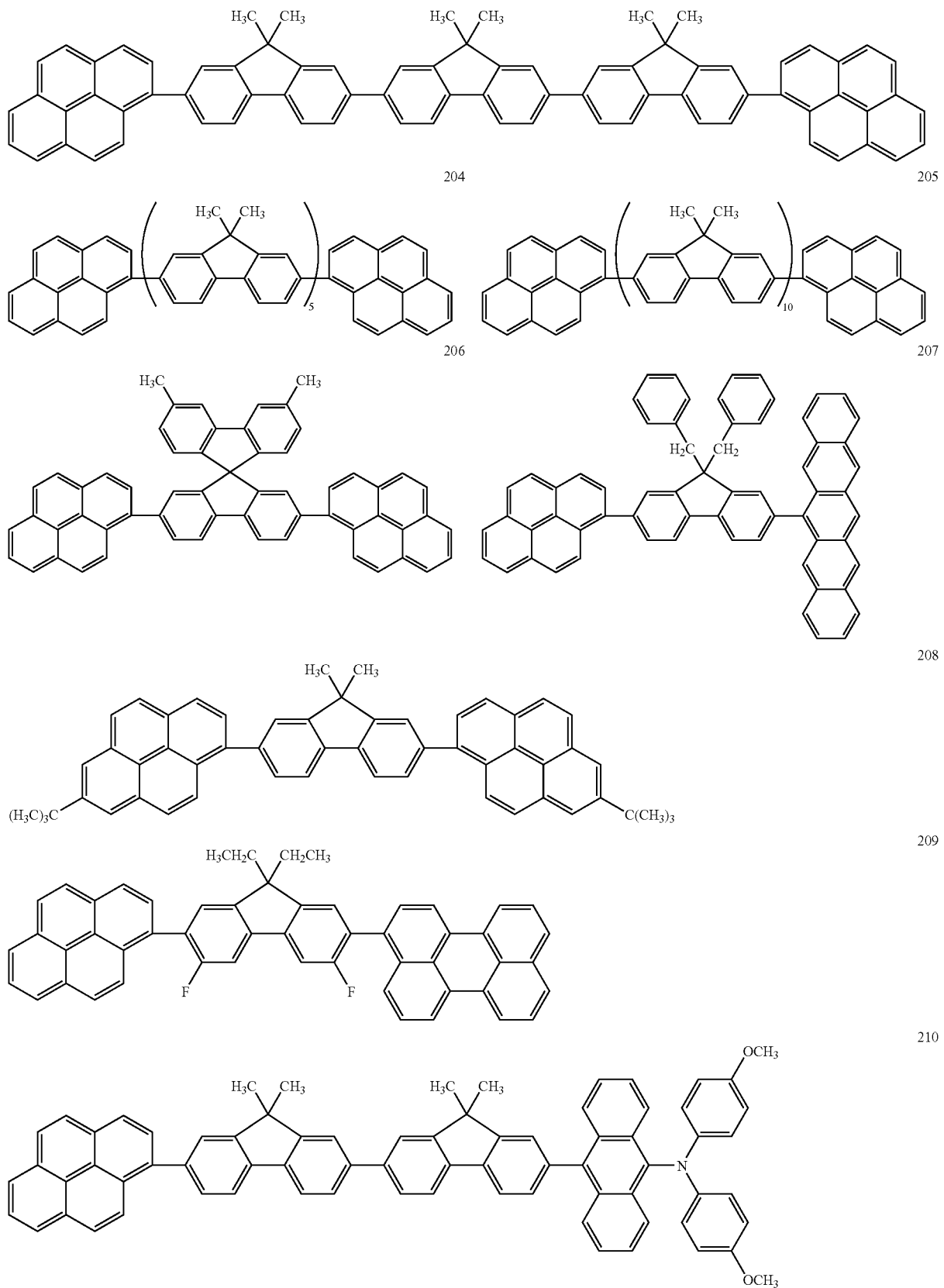

-continued
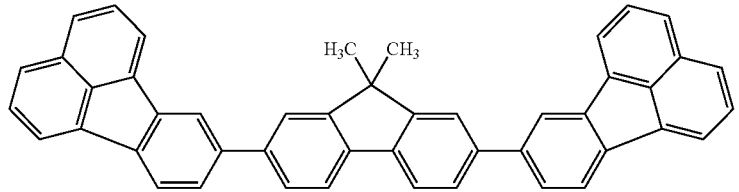
211
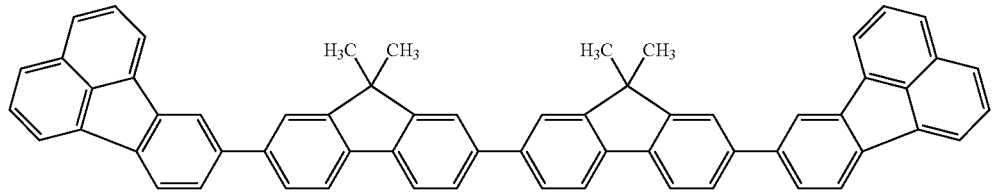
212
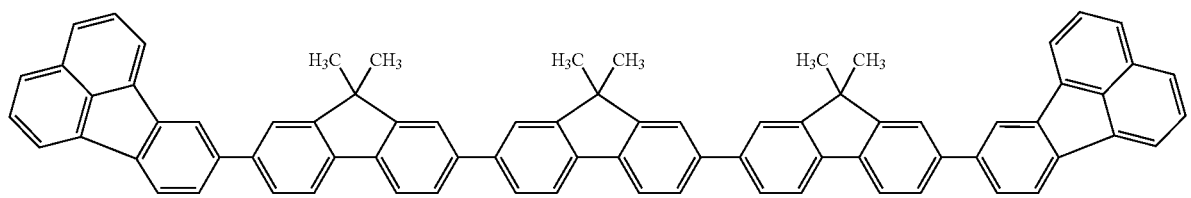
213
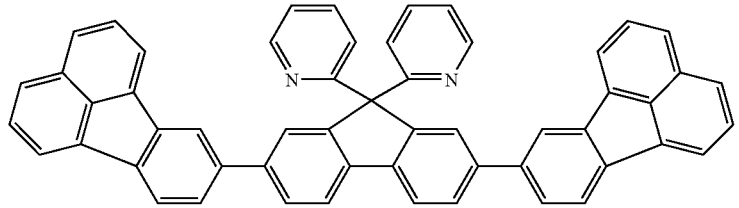
214
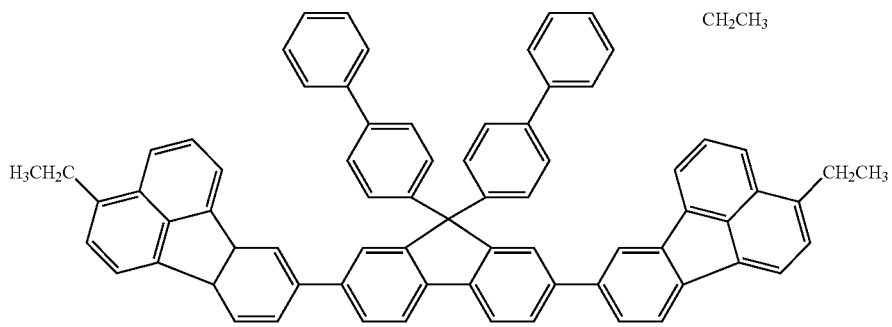
215
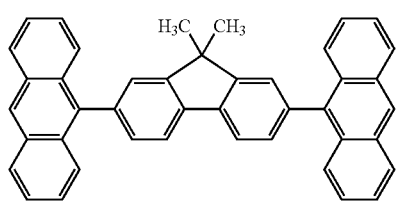
216
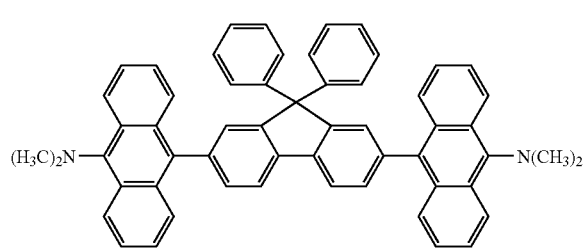
217

-continued
218 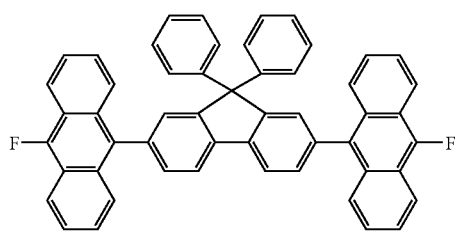
219 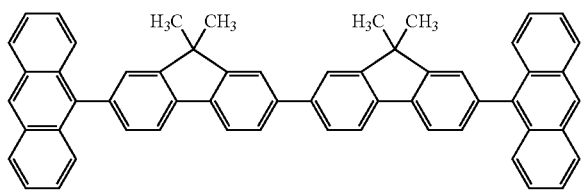
220 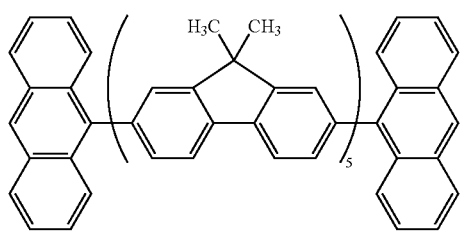
221 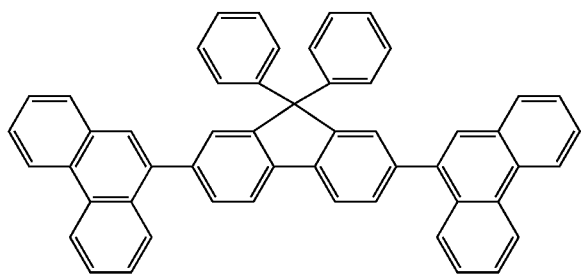
222 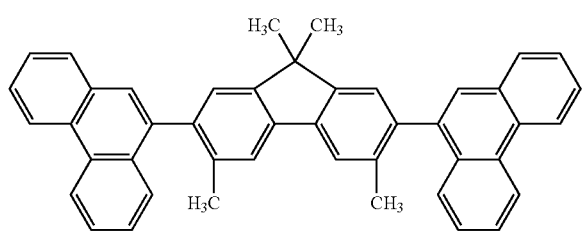
223 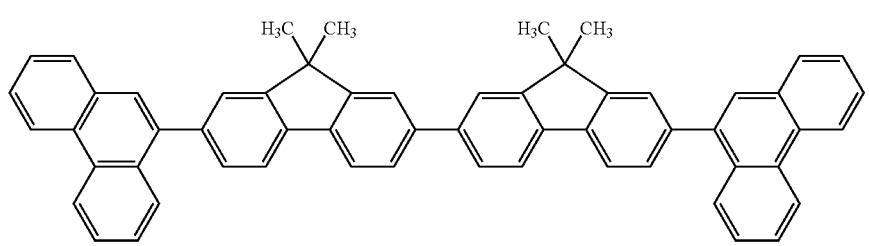
224 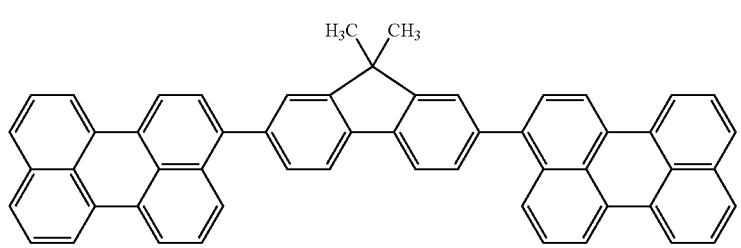
225 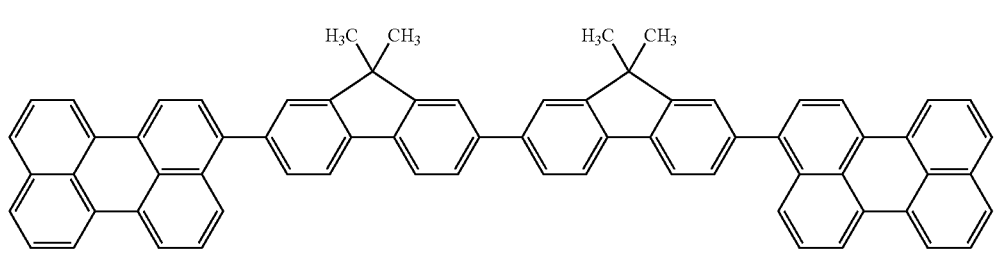

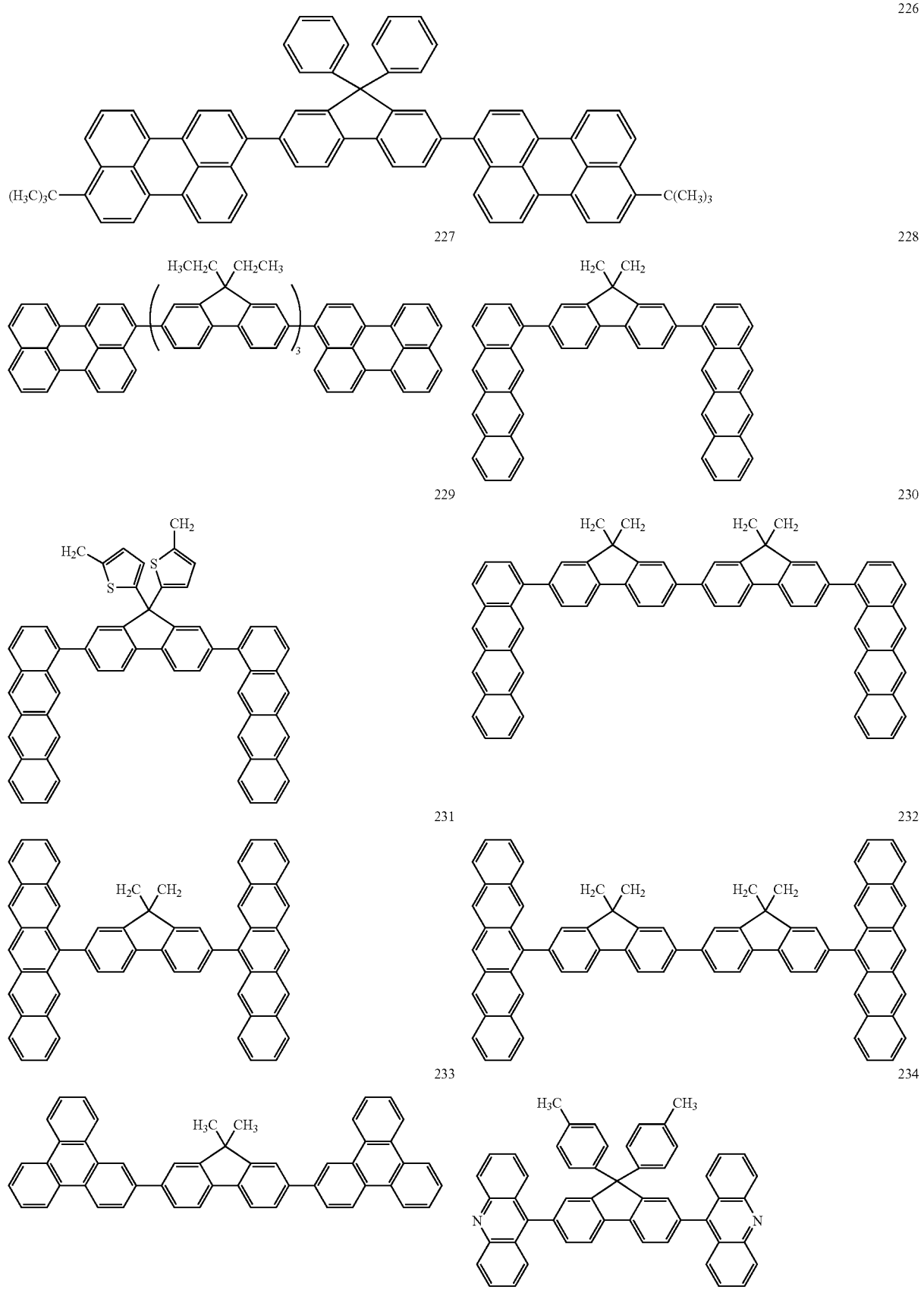

-continued
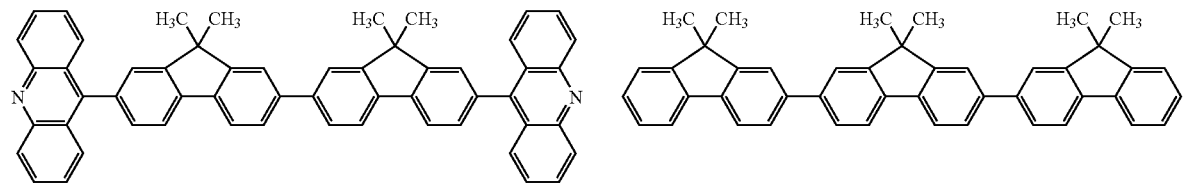
235
236
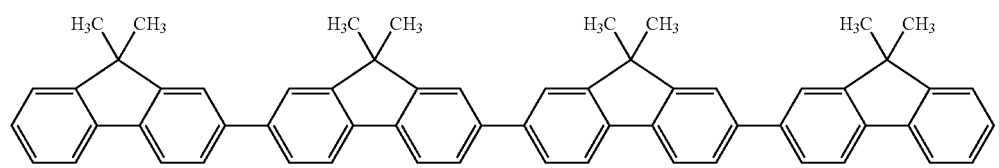
237
General Formula (5)
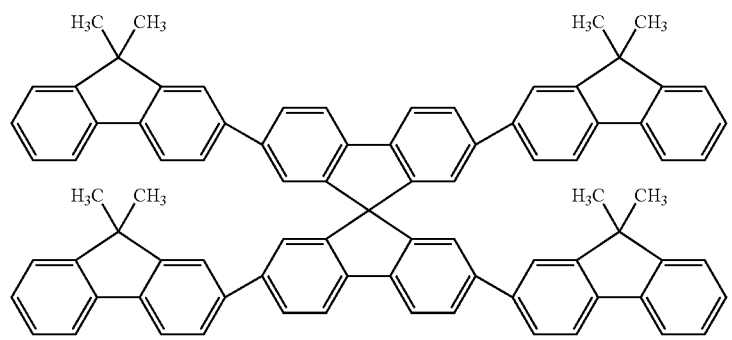
301
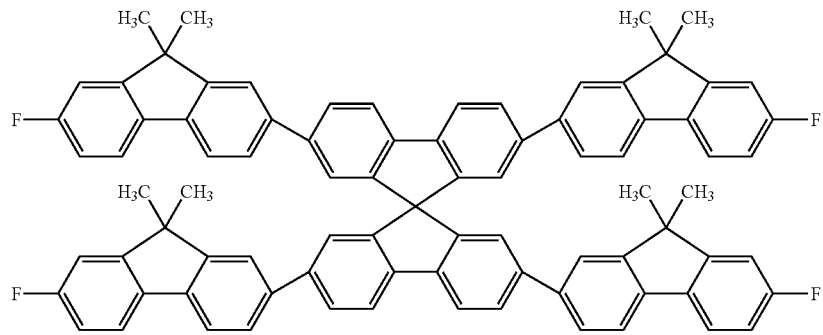
302
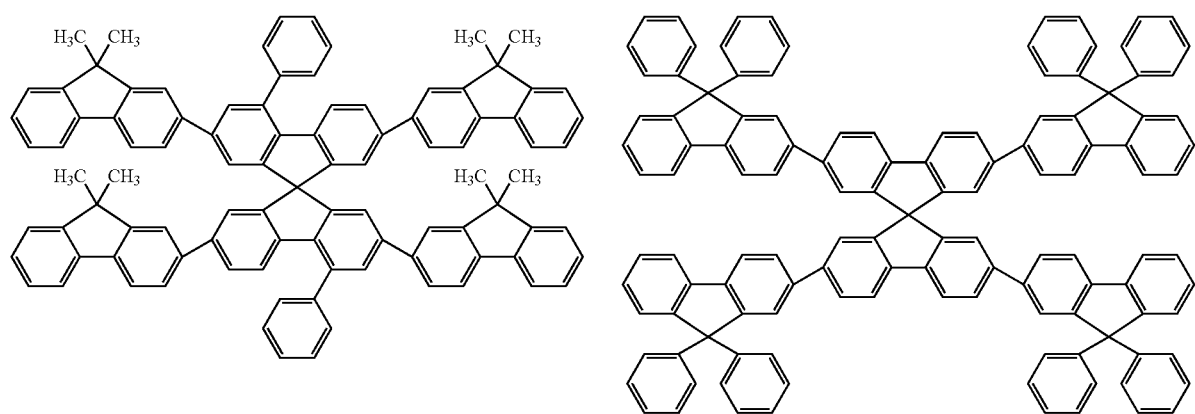
303
304

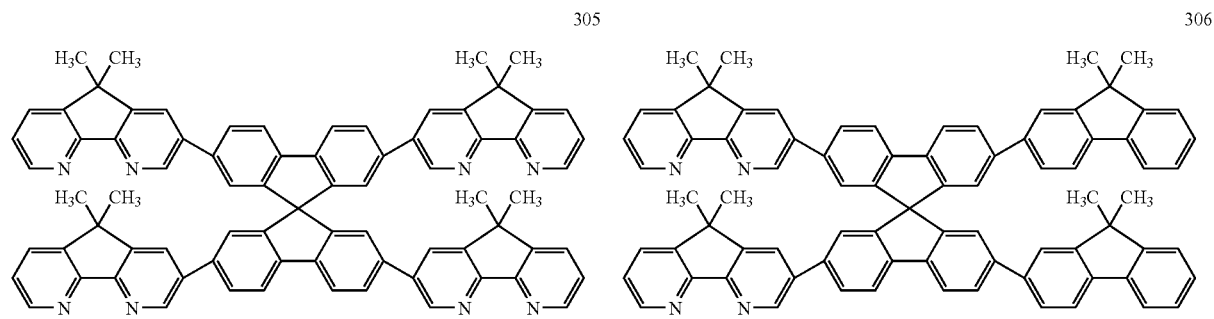
305 306
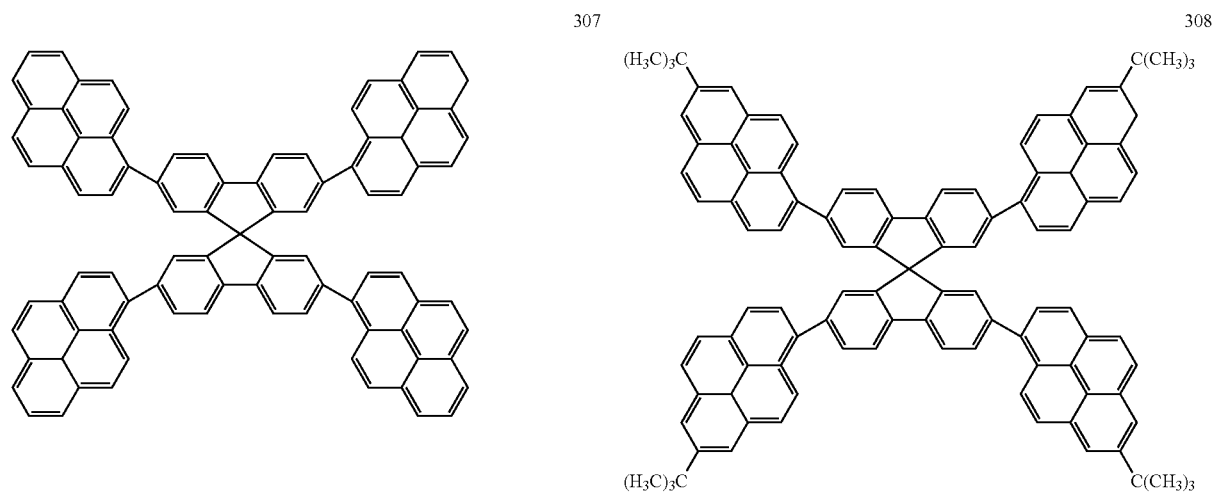
307 308
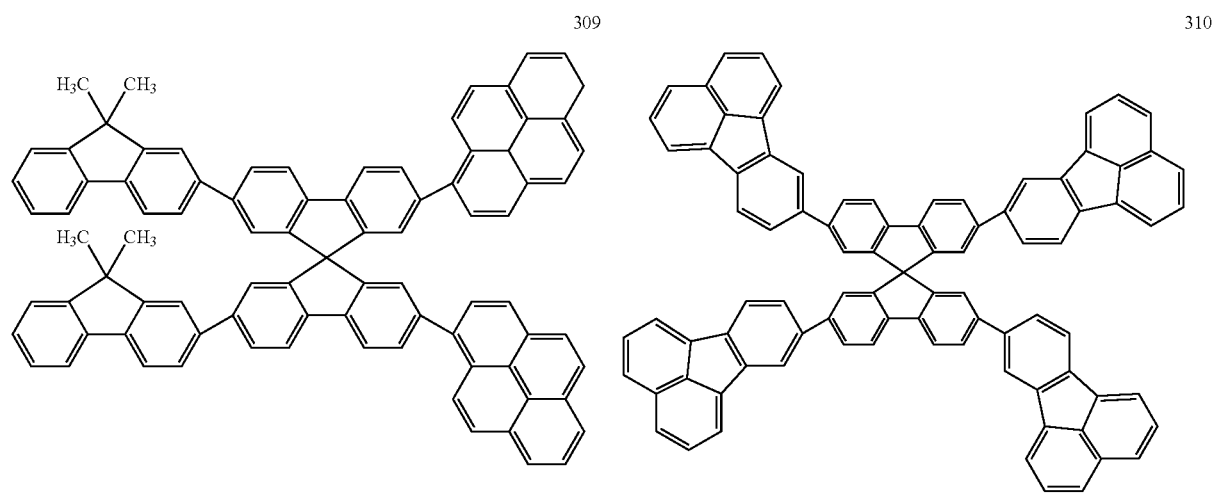
309 310

-continued
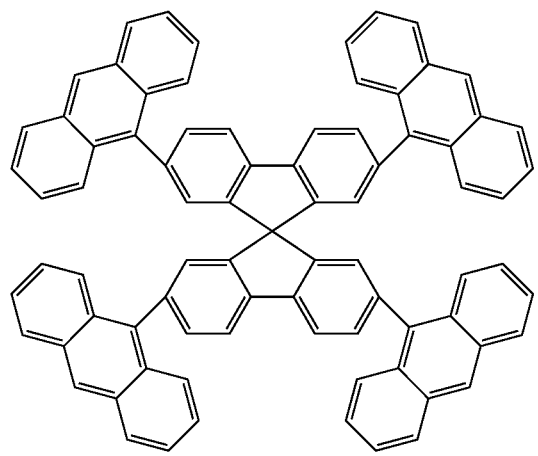
311
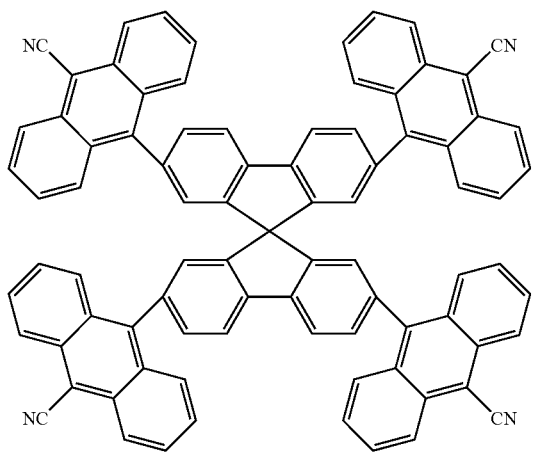
312
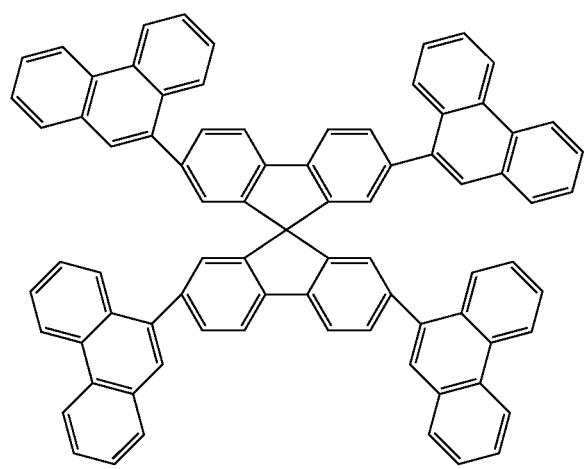
313
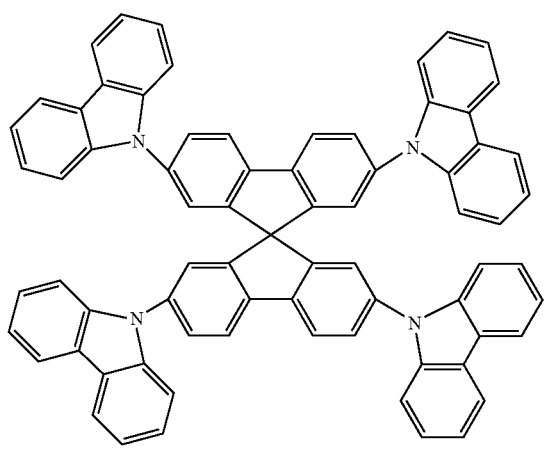
314
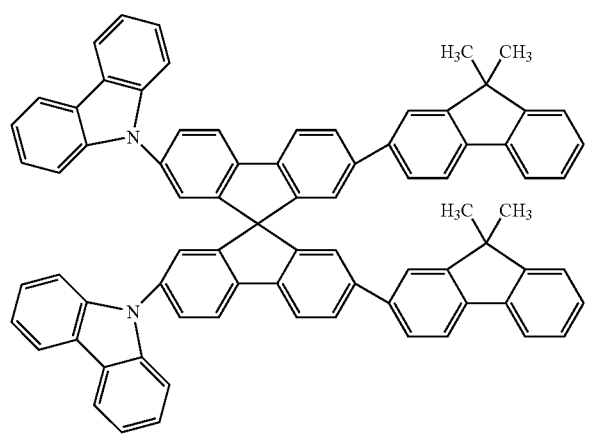
315
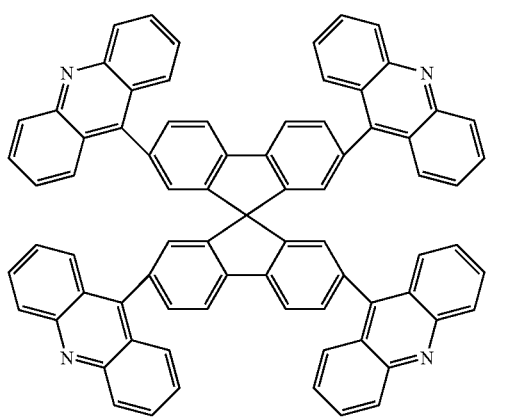
316

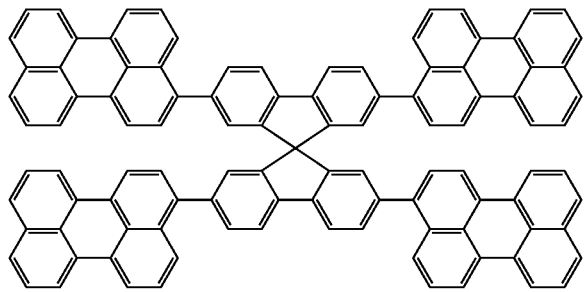 317
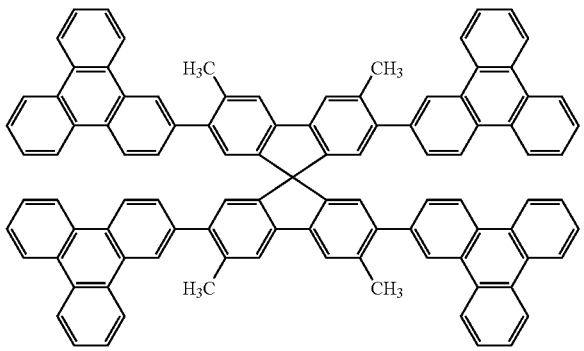 318
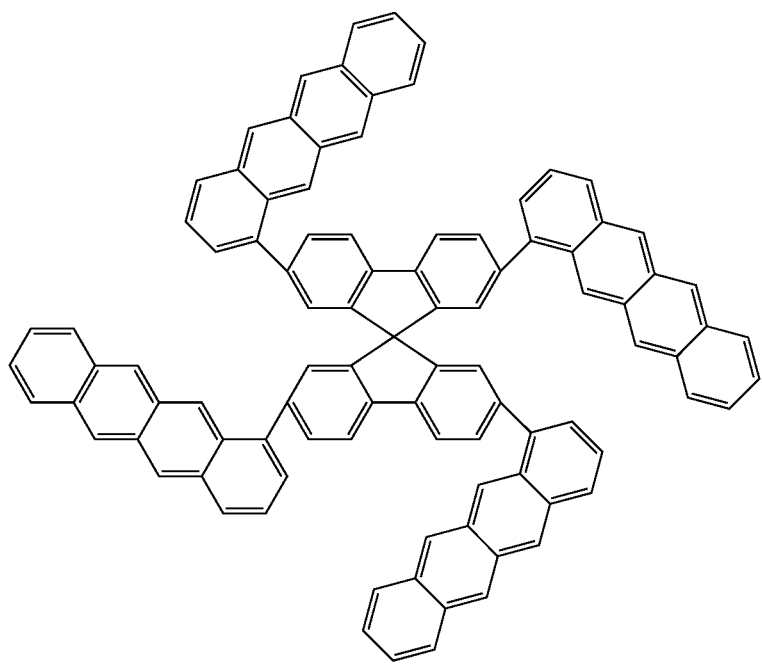 319
General Formula (6)

| Compound No. | | Z3 | | Z2 | Ar9 | Ar10 |
|---|---|---|---|---|---|---|
| 401 |  | Direct bond | 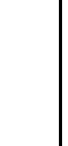 | Direct bond |  |  |
| 402 |  | Direct bond |  | Direct bond |  | 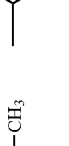 |
| 403 |  | Direct bond | | Direct bond | | |

-continued

| Compound No. | (pyrene core with (R16)p) | Z3 | fluorene core with R12 R13, (R14)j, (R15)k, n | Z2 | Ar9 | Ar10 |
|---|---|---|---|---|---|---|
| 404 | 1-substituted pyrene | Direct bond | 9,9-dimethylfluorene (2,7-disubstituted) | Direct bond | 4-C(CH₃)₃-phenyl | 4-C(CH₃)₃-phenyl |
| 405 | 1-substituted pyrene | Direct bond | 9,9-dimethylfluorene (2,7-disubstituted) | Direct bond | 2,4,6-trimethylphenyl (mesityl) | 1-naphthyl |
| 406 | 1-substituted pyrene | Direct bond | 9,9-dimethylfluorene (2,7-disubstituted) | Direct bond | 2,4,6-trimethylphenyl (mesityl) | 2,4,6-trimethylphenyl (mesityl) |

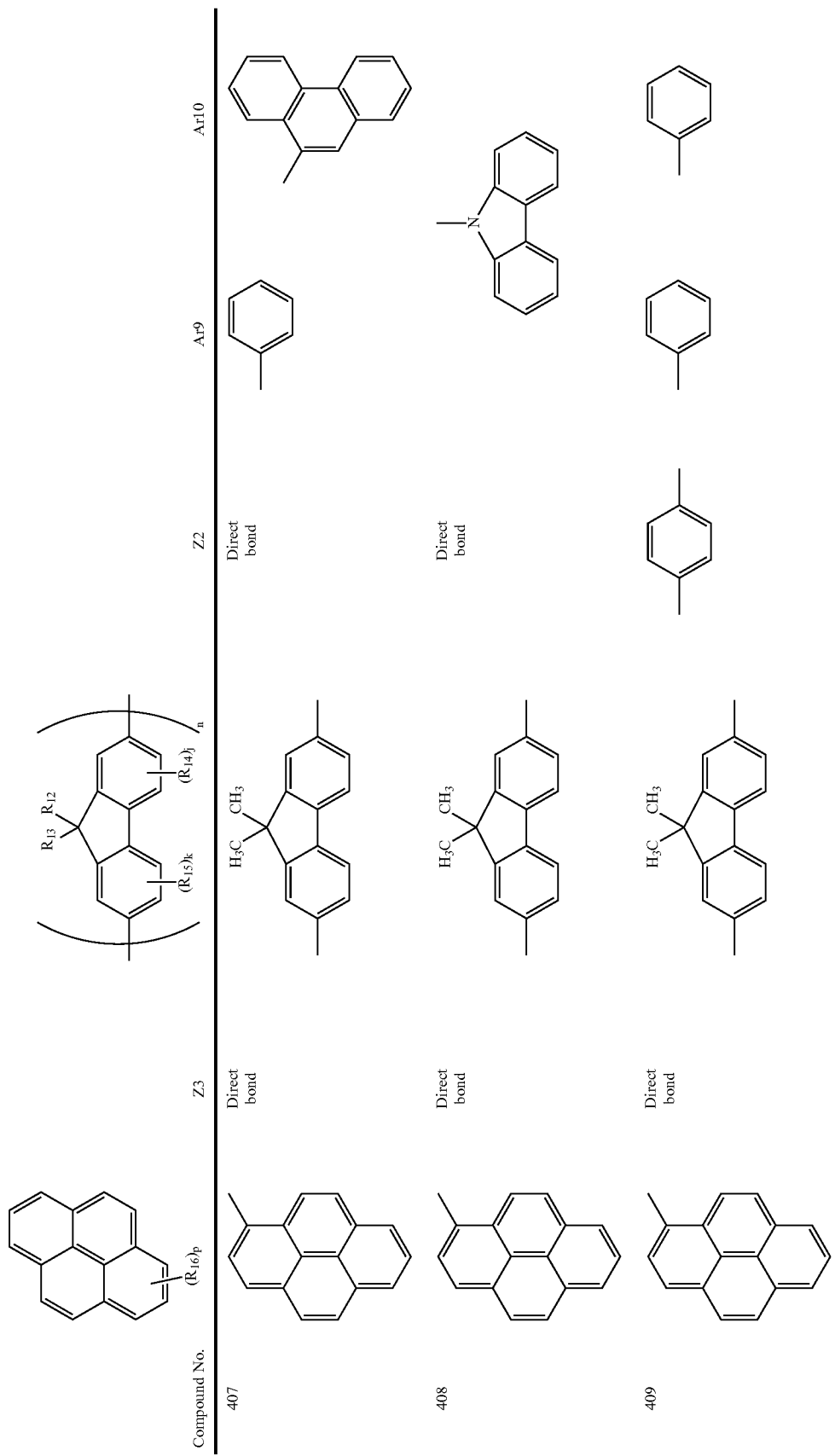

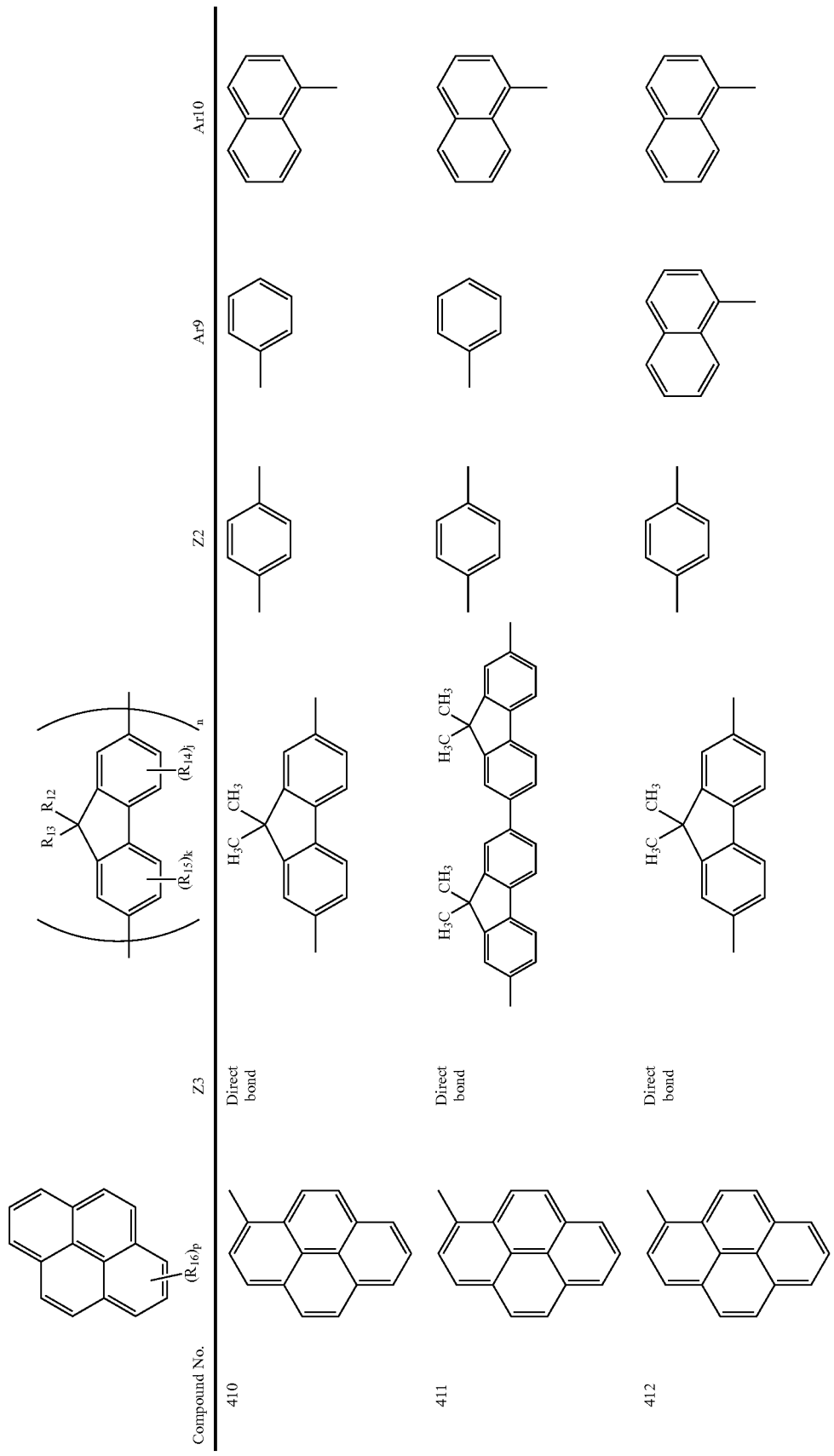

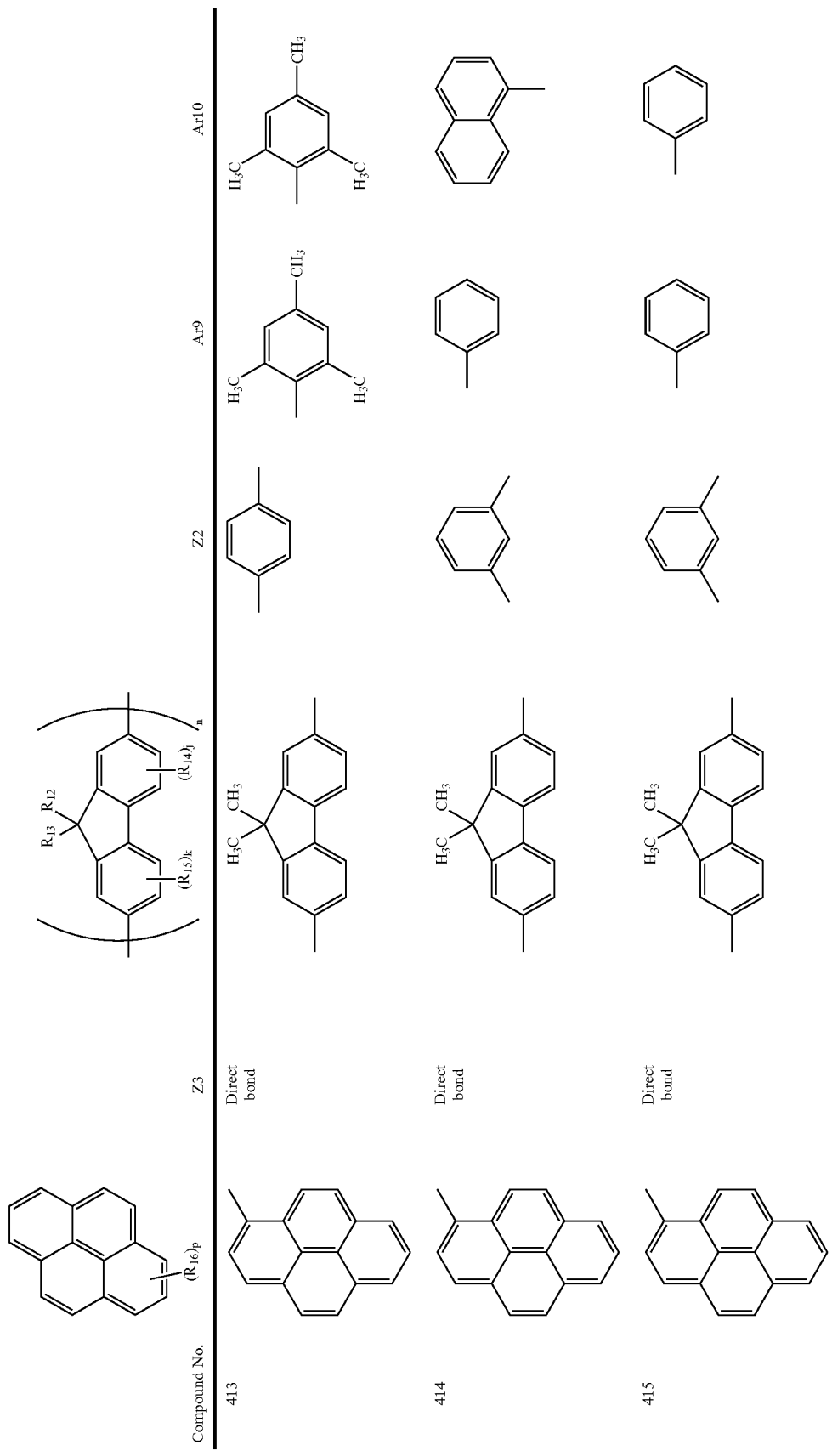

-continued

| Compound No. | | Z3 | | Z2 | Ar9 | Ar10 |
|---|---|---|---|---|---|---|
| 416 | | Direct bond | | | | |
| 417 | | Direct bond | | | | |
| 418 | | Direct bond | | | | |

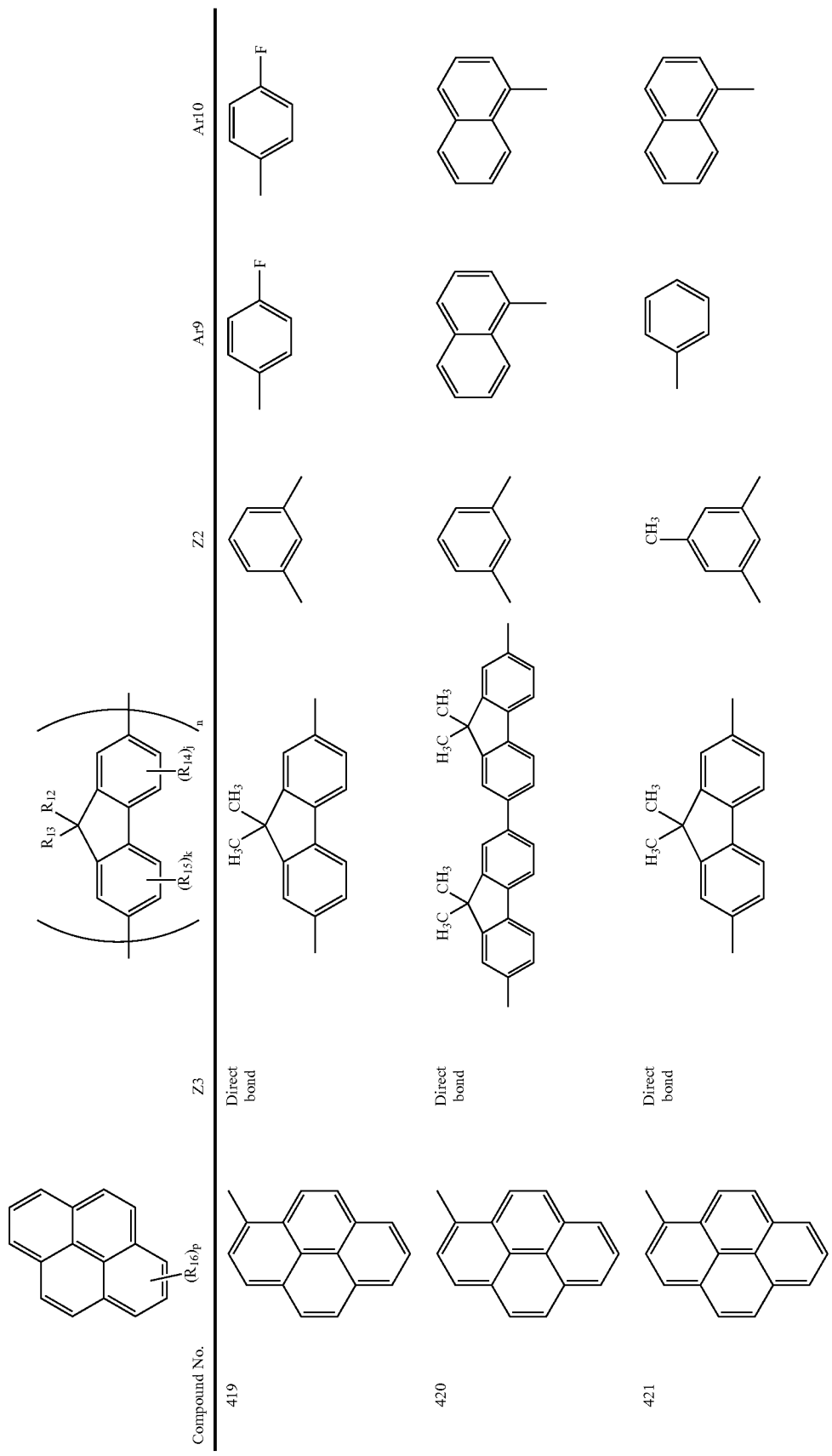

-continued
| Compound No. | 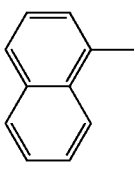 | Z3 | 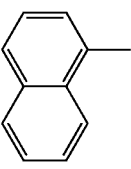 | Z2 | Ar9 | Ar10 |
|---|---|---|---|---|---|---|
| 422 | | Direct bond | | C(CH$_3$)$_3$ on 3,5-dimethylphenyl | phenyl | 1-naphthyl |
| 423 | | Direct bond | | 1,4-naphthyl (with methyls) | phenyl | phenyl |
| 424 | | Direct bond | | 2,5-dimethyl-1,4-phenylene | phenyl | 1-naphthyl |

| Compound No. | | Z3 | | Z2 | Ar9 | Ar10 |
|---|---|---|---|---|---|---|
| 425 | pyrene-(R16)p | Direct bond | fluorene with R12,R13,(R14)j,(R15)k,n | 2,5-dimethylphenyl (CH3 groups) | naphthyl | naphthyl |
| 426 | methylpyrene | p-phenylene | 9,9-dimethylfluorene (dimethyl substituted) | p-tolyl | phenyl | phenyl |
| 427 | methylpyrene | p-phenylene | 9,9-dimethylfluorene (dimethyl substituted) | p-tolyl | phenyl | naphthyl |

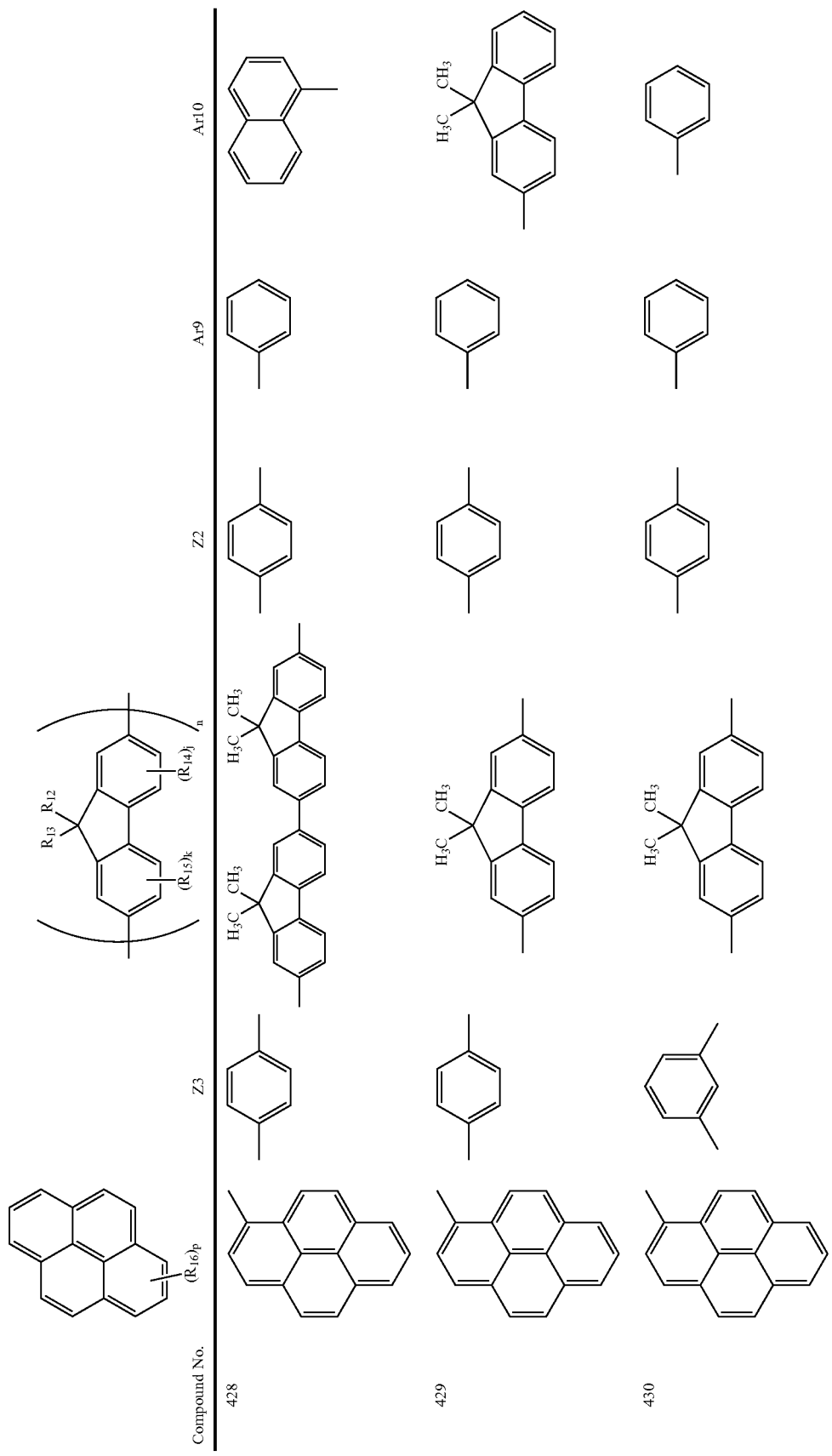

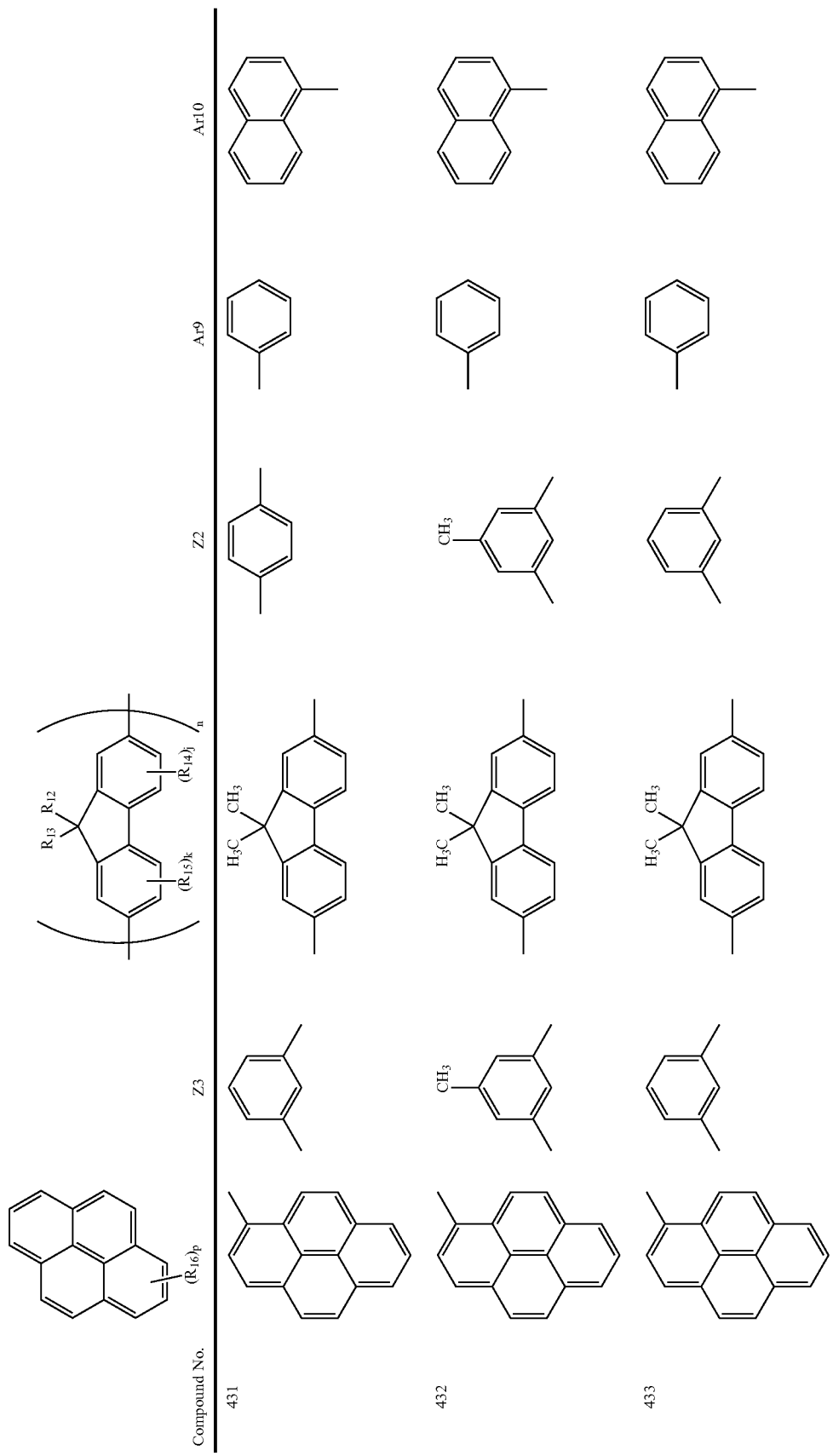

| Compound No. | ![pyrene with (R16)p] | Z3 | ![fluorene structure with R12 R13, (R14)j, (R15)k, n] | Z2 | Ar9 | Ar10 |
|---|---|---|---|---|---|---|
| 434 | ![methylpyrene with t-Bu] | Direct bond | ![9,9-dimethylfluorene with methyl substituents] | Direct bond | ![tolyl] | ![naphthyl] |
| 435 | ![dimethylpyrene with t-Bu and Me] | Direct bond | ![9,9-dimethylfluorene with methyl substituents] | Direct bond | ![p-(t-Bu)phenyl] | ![p-(t-Bu)phenyl] |

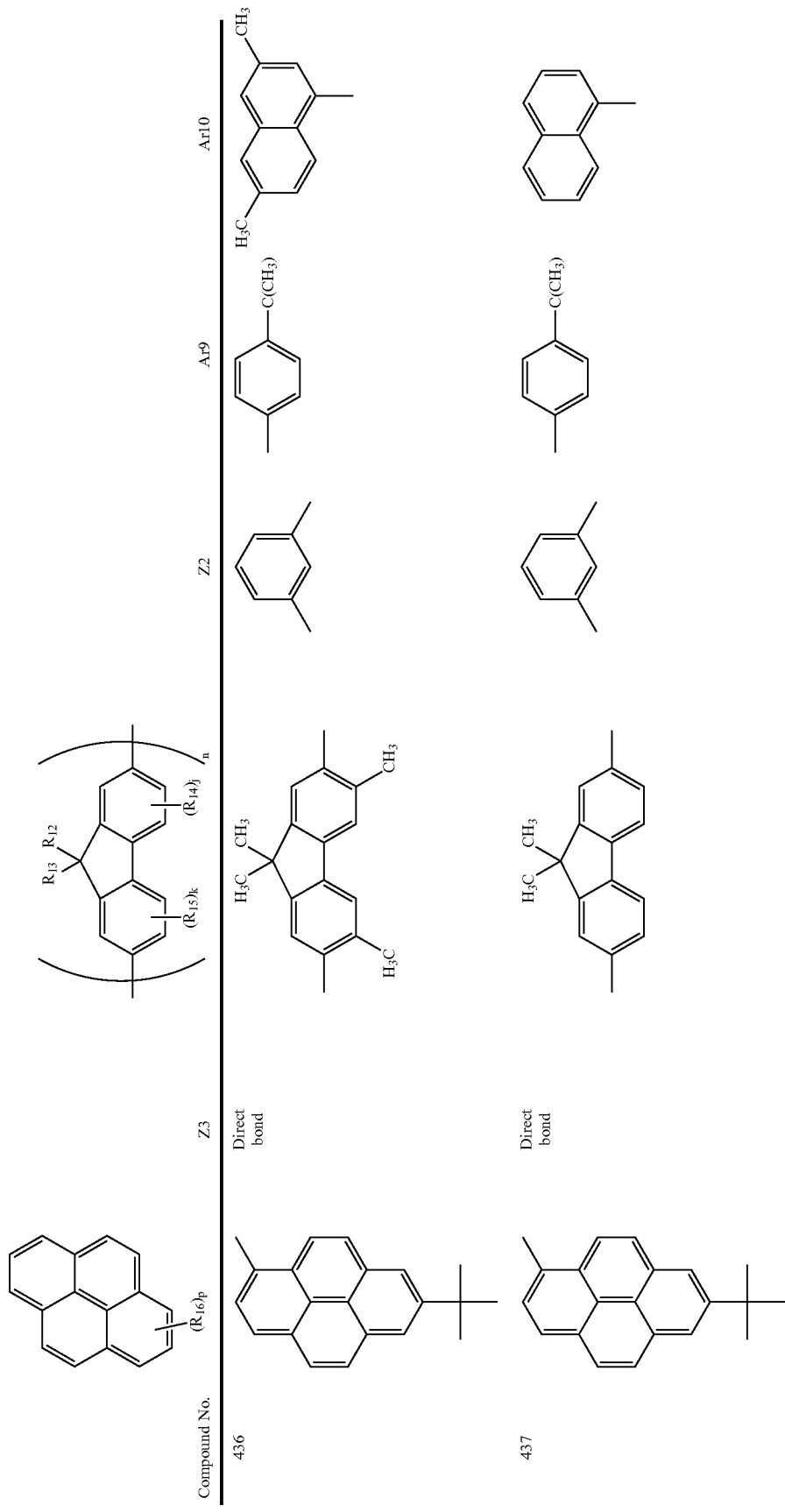

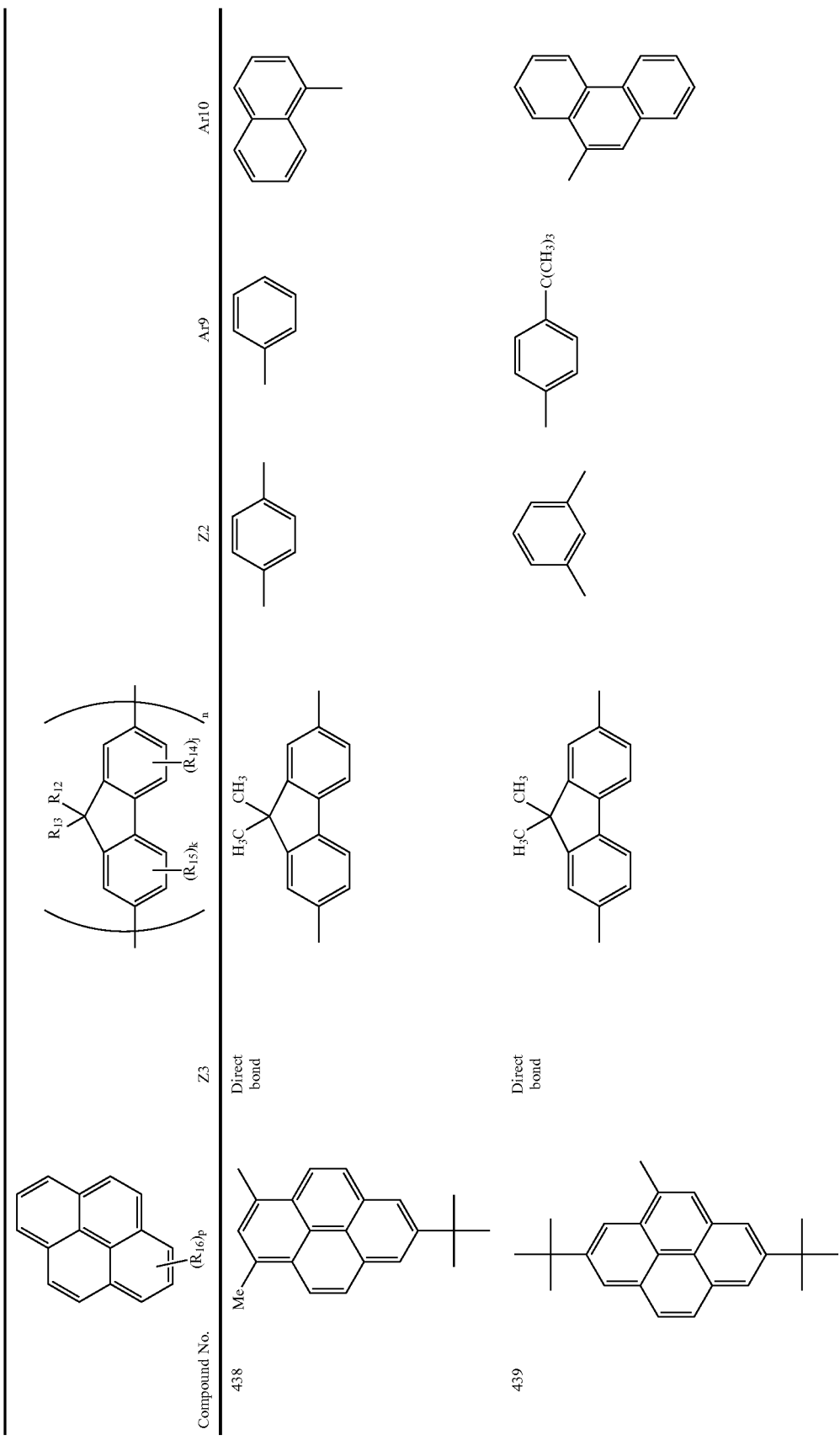

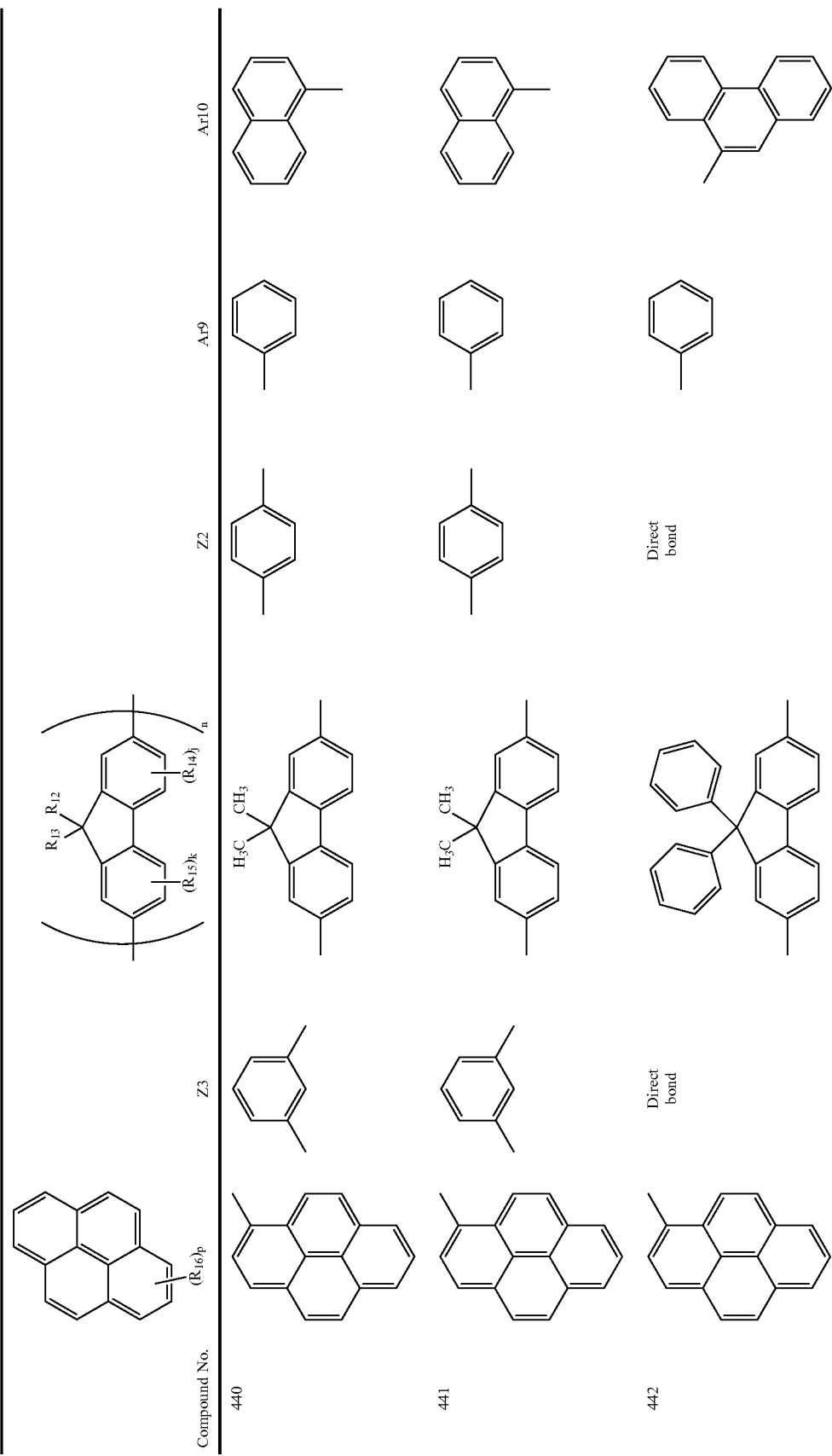

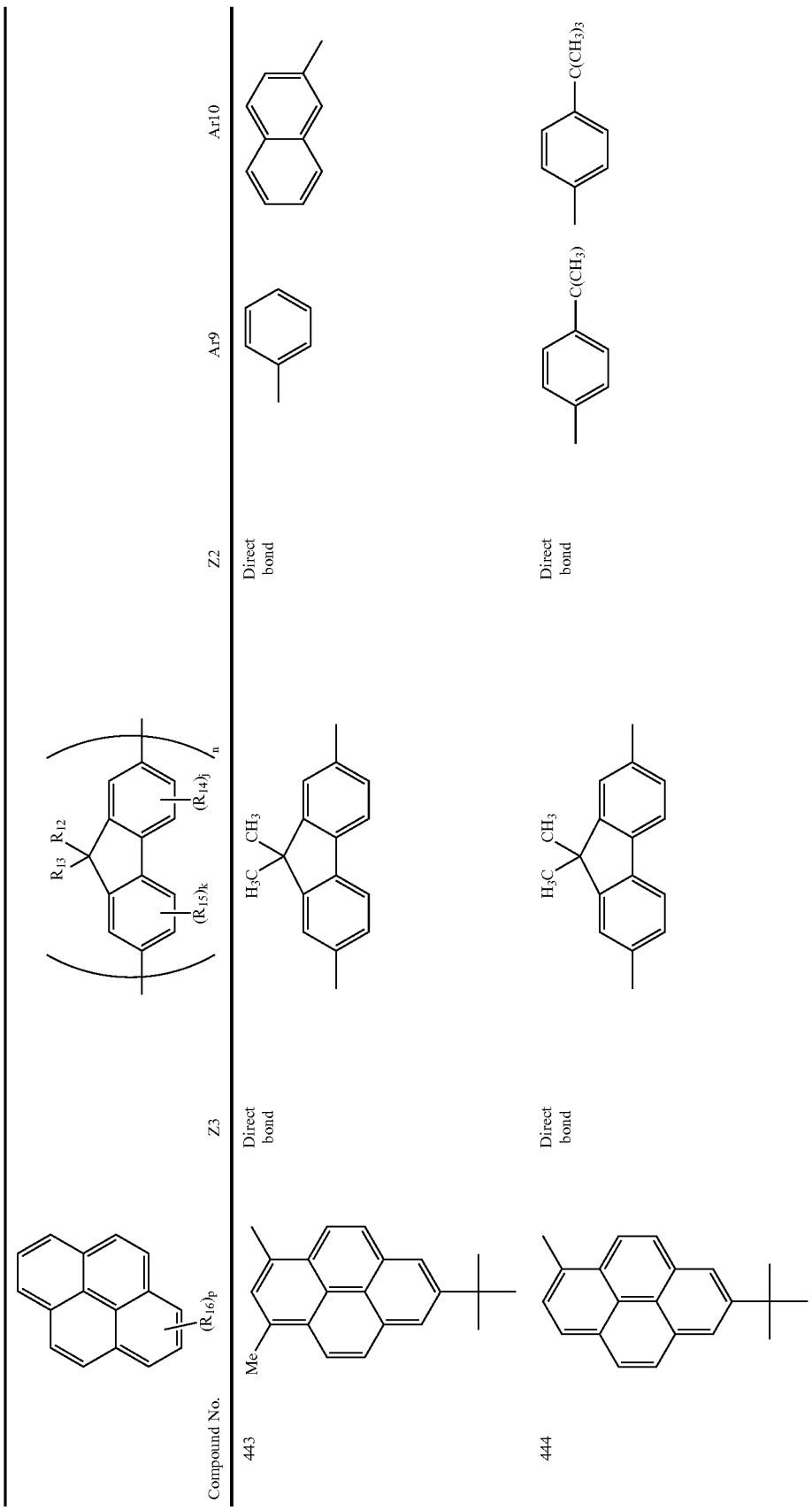

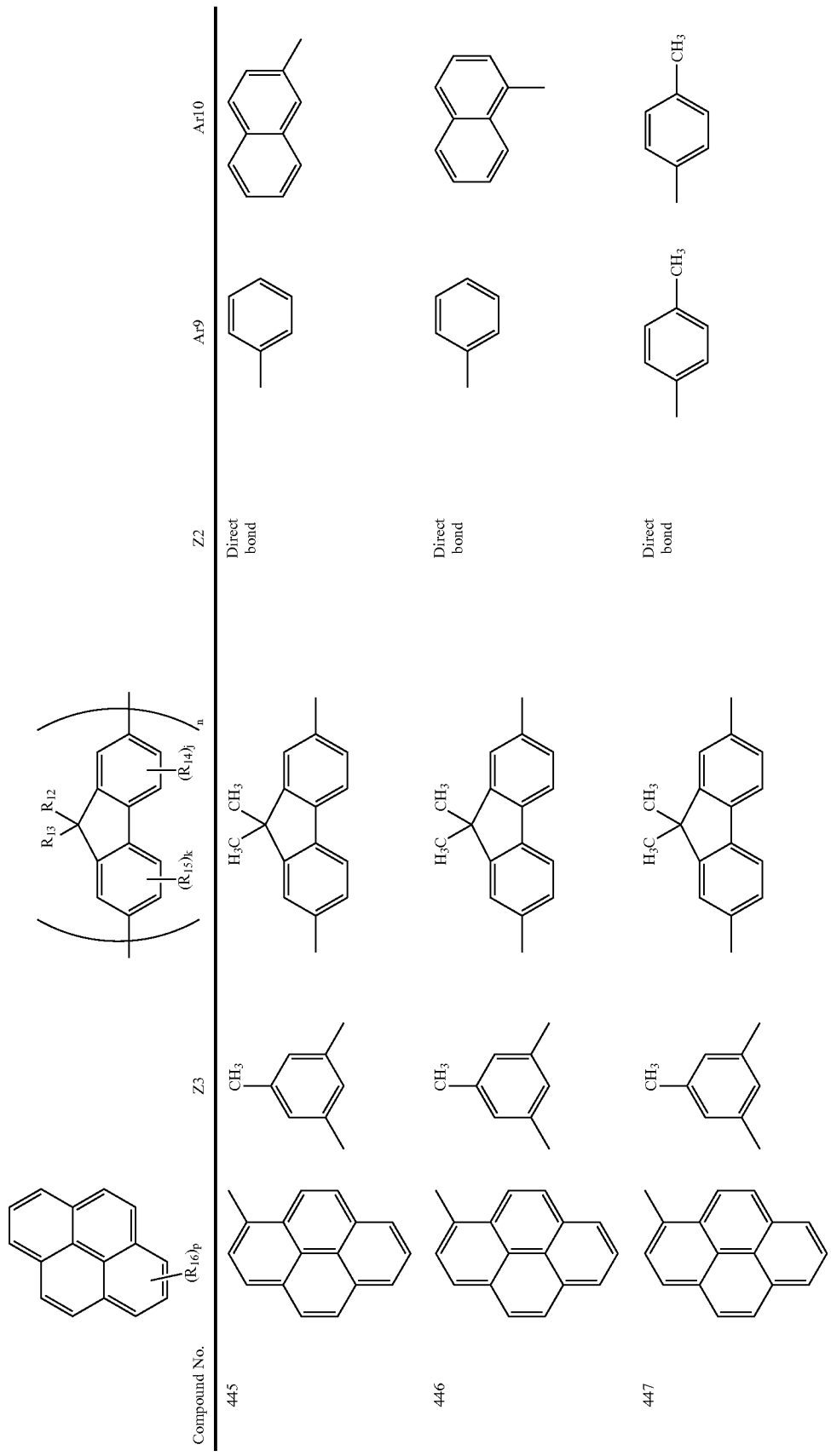

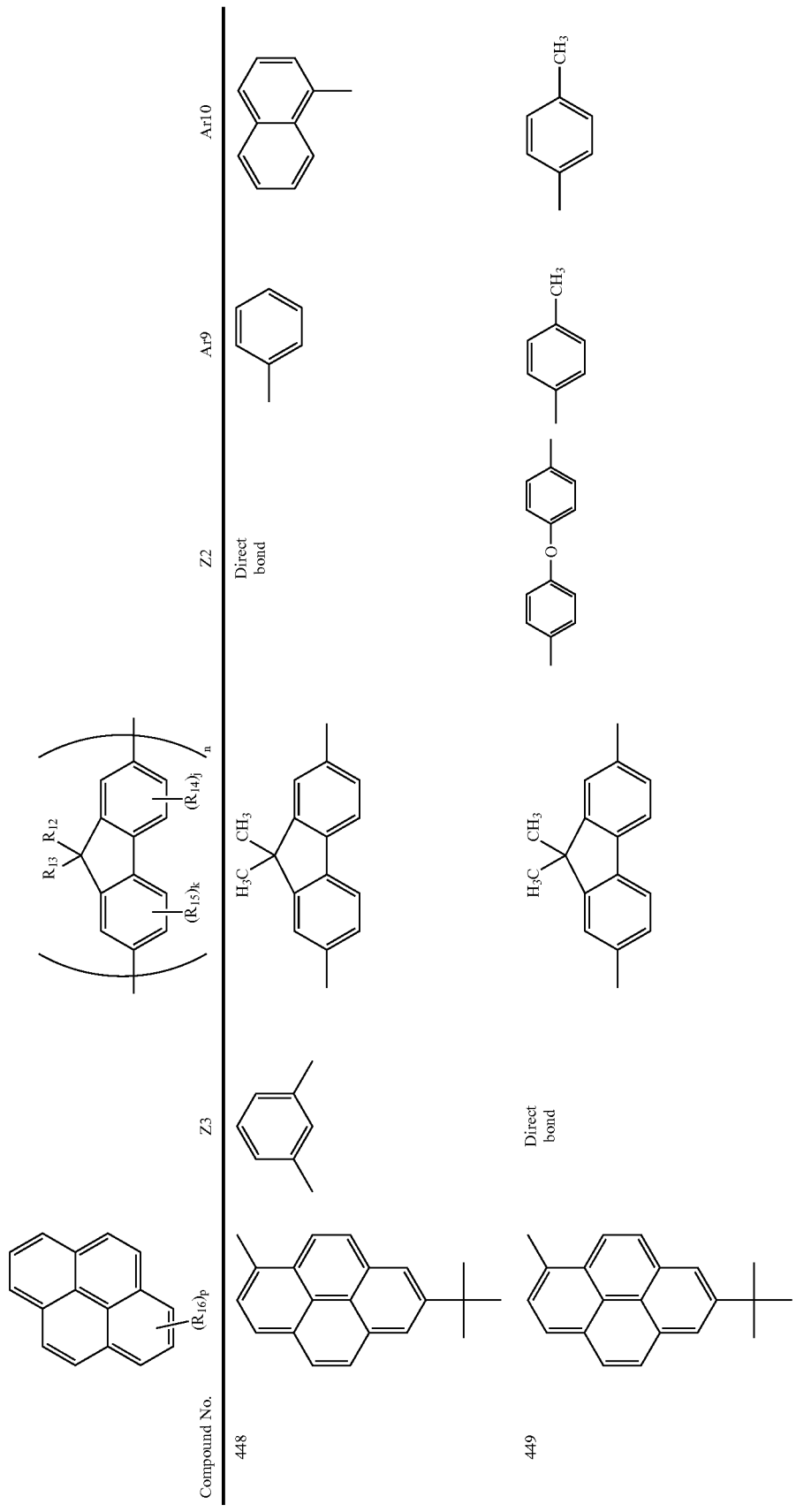

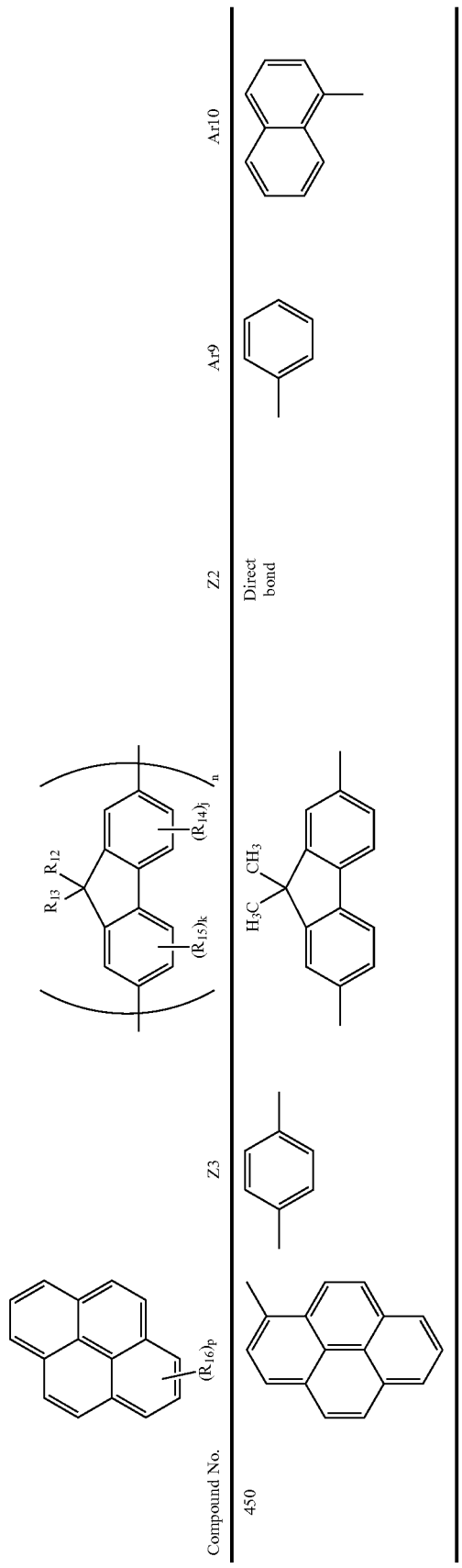

General Formula (7)
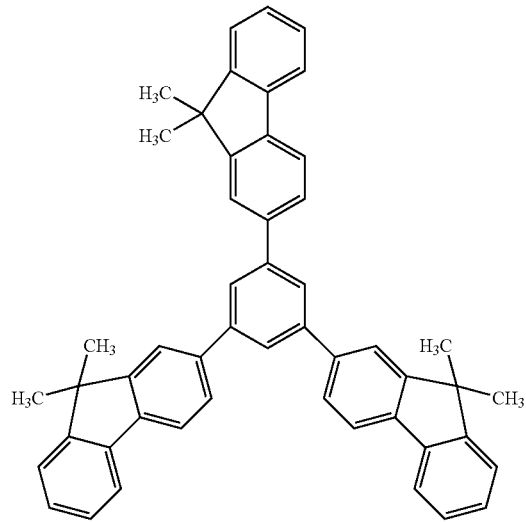
501
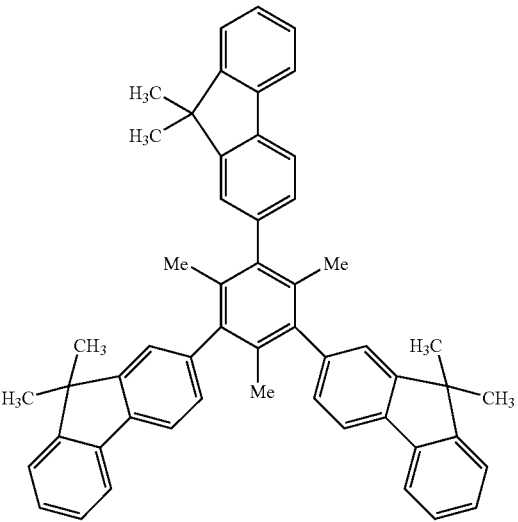
503
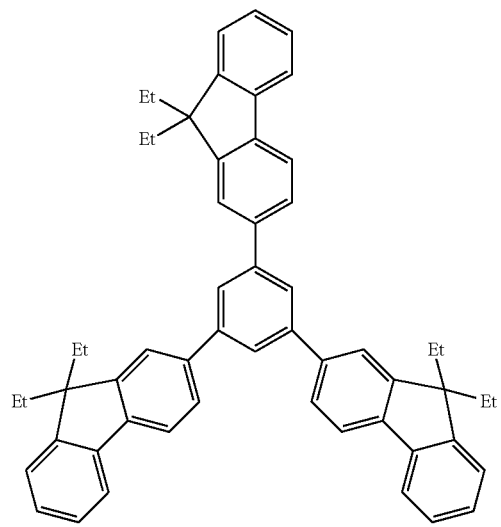
504
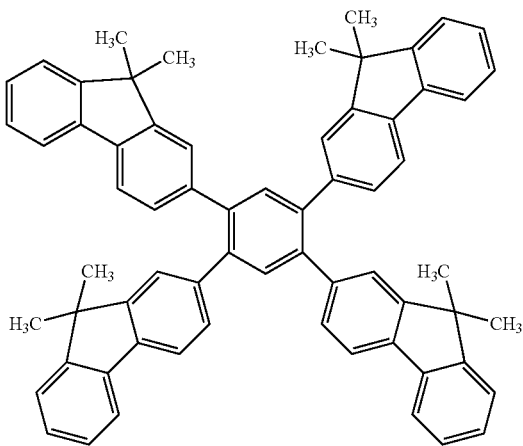
505
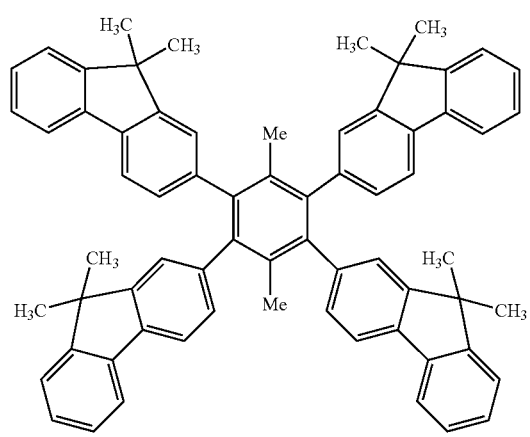
506
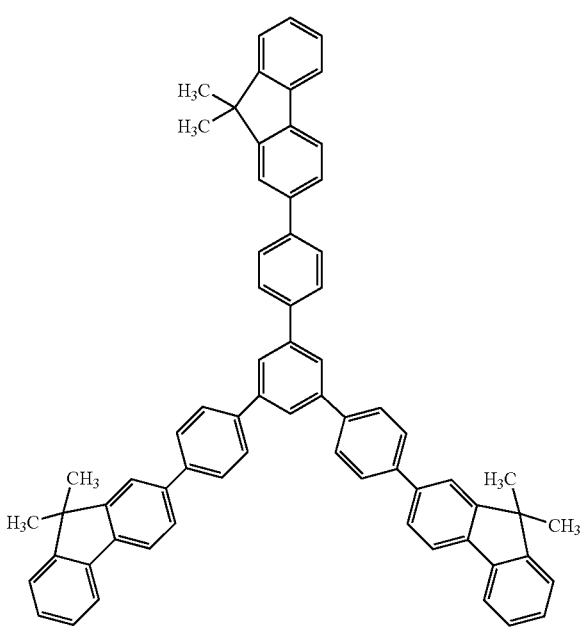

-continued
507
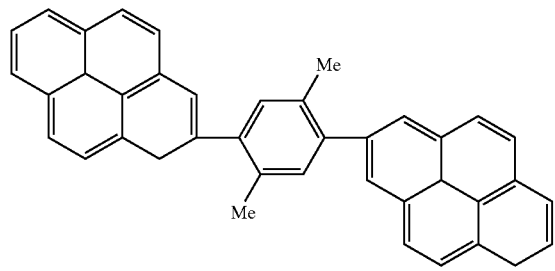
508
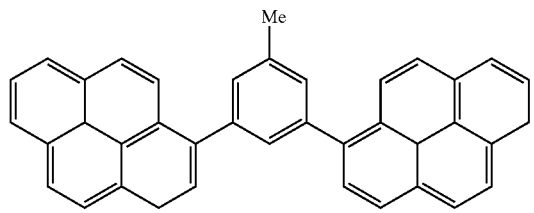
509
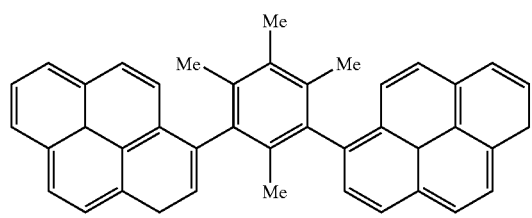
510
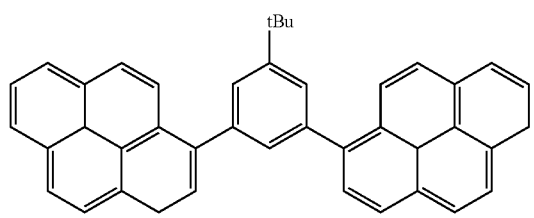
511
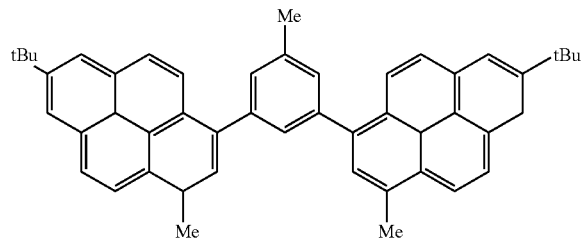
512
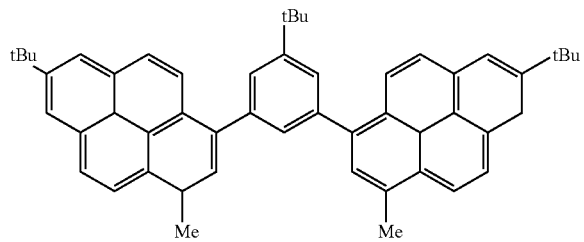
513
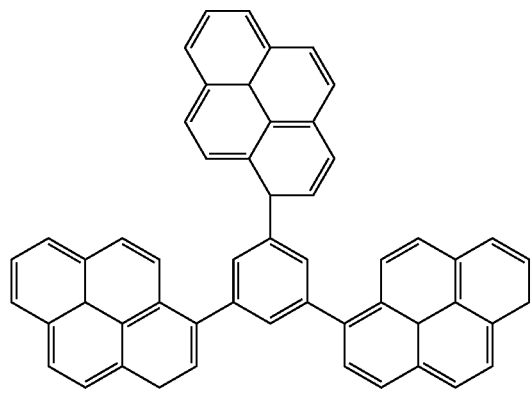
514
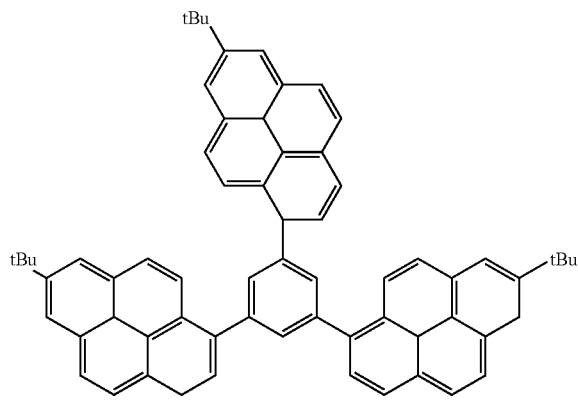
515
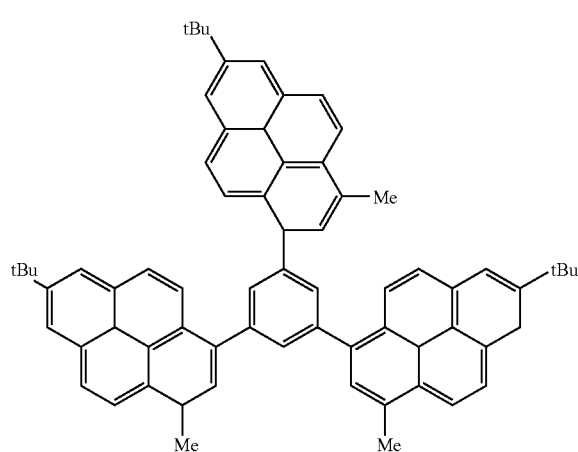
516
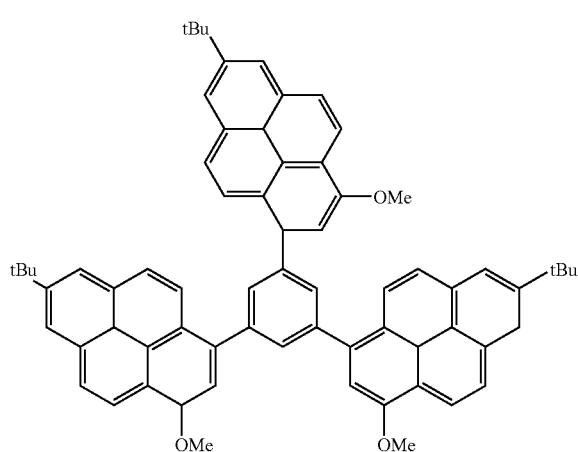

-continued
517
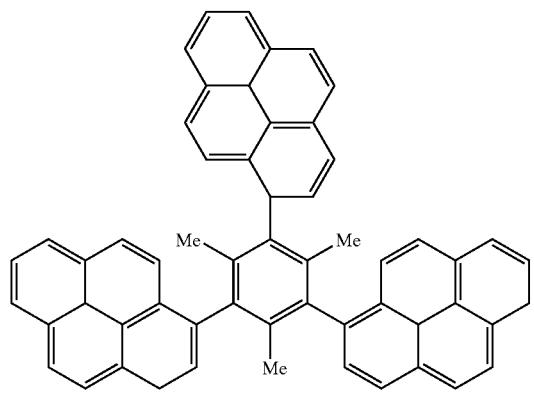
518
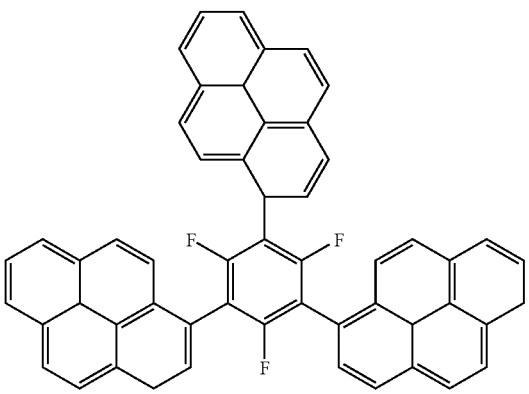
519
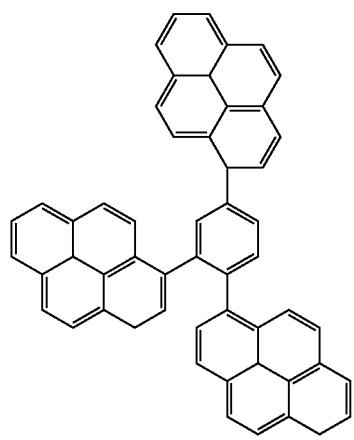
520
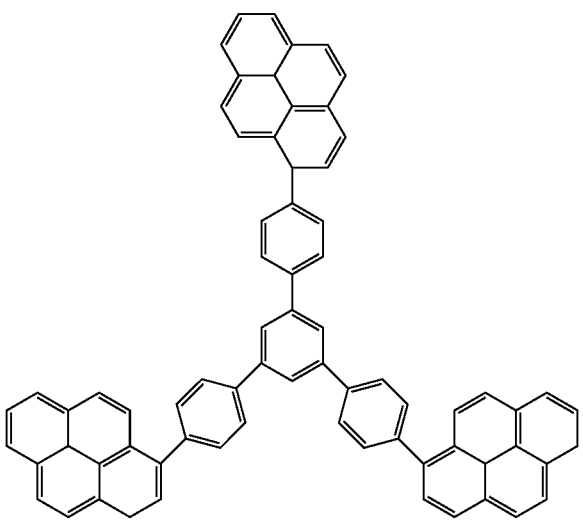
521
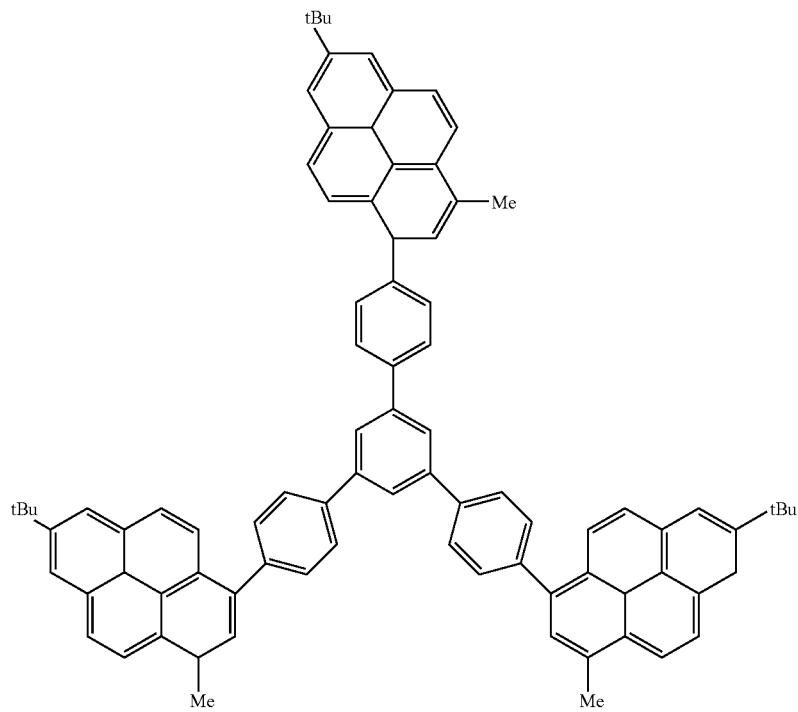

-continued
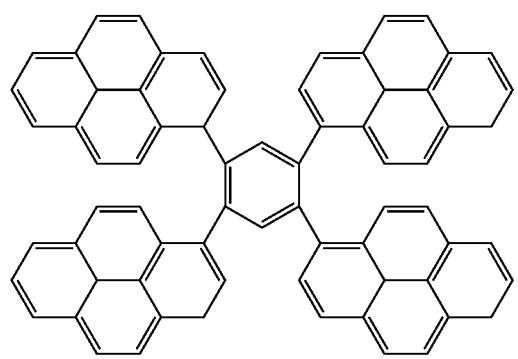
522
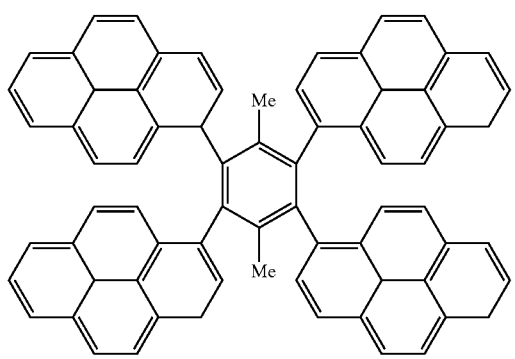
523
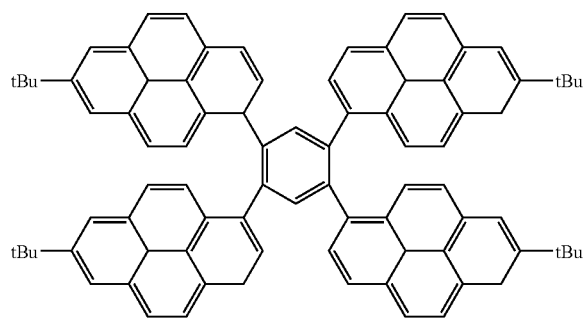
524
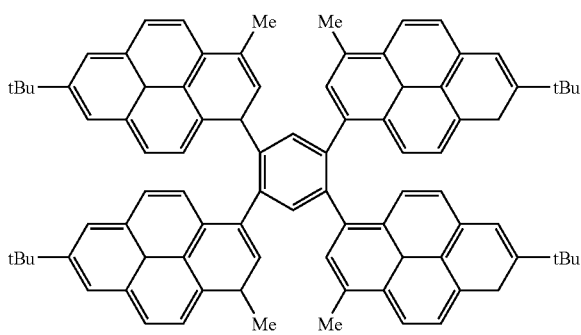
525
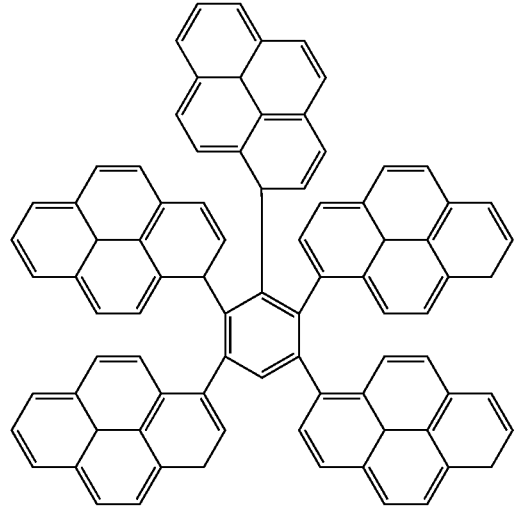
526
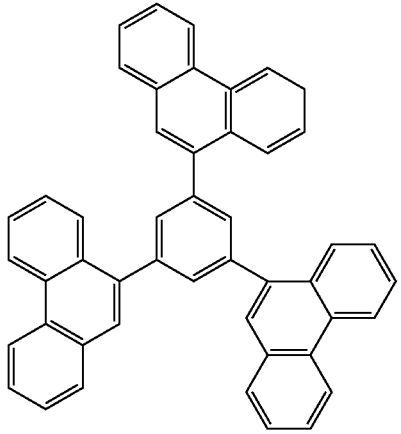
527
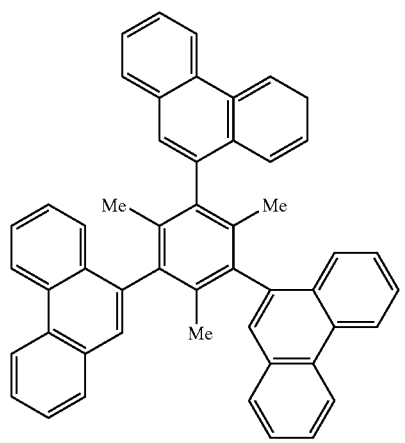
528

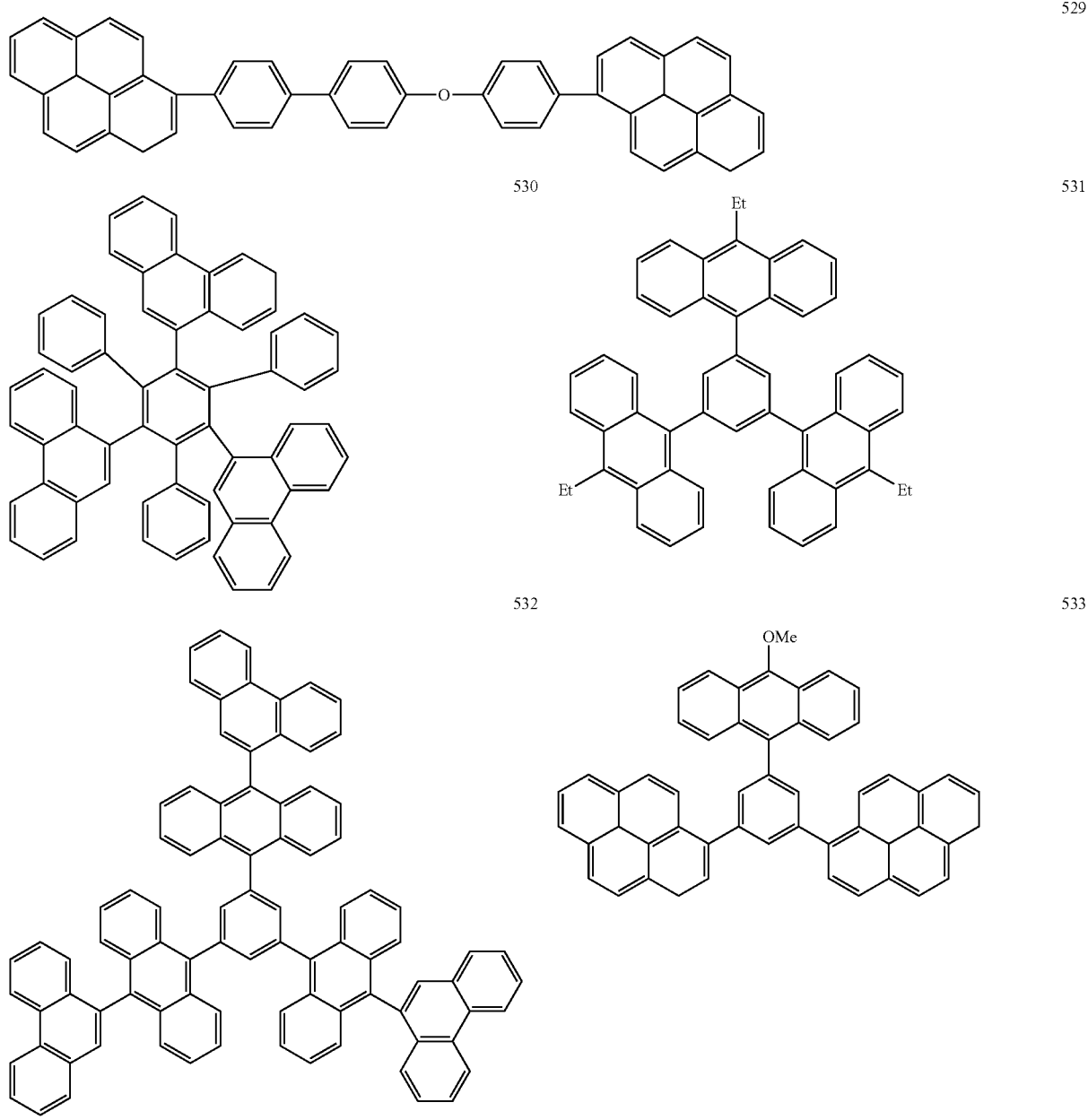

Next, an organic light emitting device of the present invention will be described in more detail.

The organic light emitting device of the present invention includes: a pair of electrodes formed of an anode and a cathode; and an organic compound layer interposed between the pair of electrodes. In the organic light emitting device, the organic compound layer or preferably the light emitting layer contains the above-mentioned silyl compound.

FIGS. 1 to 5 each illustrate a preferable example of the organic light emitting device of the present invention.

First, each reference numeral will be described.

Provided are a substrate 1, an anode 2, a light emitting layer 3, a cathode 4, a hole transporting layer 5, an electron transporting layer 6, a hole injecting layer 7, and a hole/exciton blocking layer 8.

FIG. 1 is a sectional view illustrating an example of an organic light emitting device according to the present invention. As illustrated in FIG. 1, the organic light emitting device has a structure in which the anode 2, the light emitting layer 3, and the cathode 4 are provided on the substrate 1 in this order. The light emitting device used herein is useful in the case where the device itself has hole-transporting property, electron-transporting property, and light-emitting property or where compounds having the respective properties are used in combination.

Figure 2:
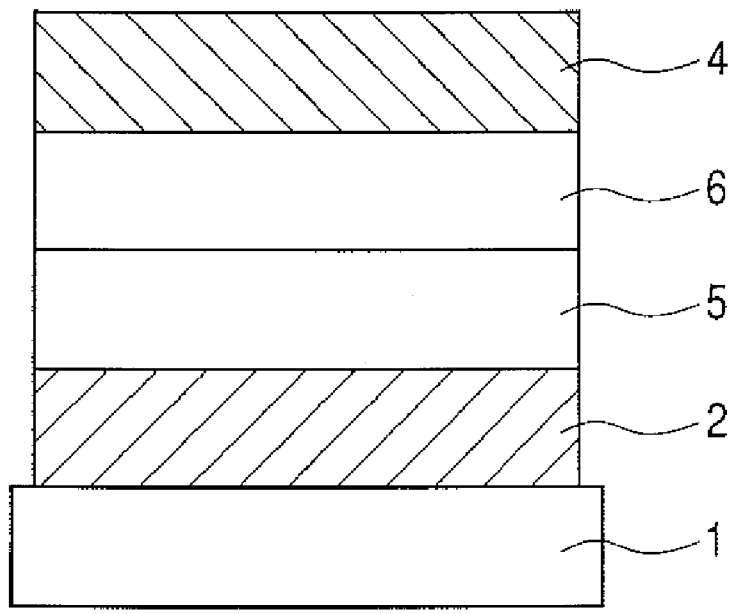
FIG. 2 is a sectional view illustrating another example of the organic light emitting device according to the present invention.

FIG. 2 is a sectional view illustrating another example of the organic light emitting device according to the present invention. As illustrated in FIG. 2, the organic light emitting device has a structure in which the anode 2, the hole transporting layer 5, the electron transporting layer 6, and the cathode 4 are provided on the substrate 1 in this order. A light emitting substance is useful in the case where a material having one or both of hole-transporting property and electron-transporting property is used for each layer, and the light emitting substance is used in combination with a non-illuminant hole transporting substance or electron transporting substance. In this case, the light emitting layer is formed of the hole transporting layer 5 or the electron transporting layer 6.

Figure 3:
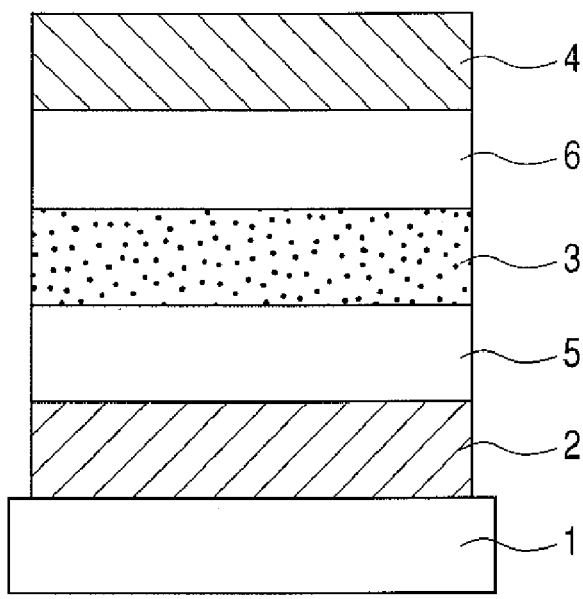
FIG. 3 is a sectional view illustrating still another example of the organic light emitting device according to the present invention.

FIG. 3 is a sectional view illustrating still another example of the organic light emitting device according to the present invention. As illustrated in FIG. 3, the organic light emitting device has a structure in which the anode 2, the hole transporting layer 5, the light emitting layer 3, the electron transporting layer 6, and the cathode 4 are provided on the substrate 1 in this order. This organic light emitting device has separate carrier-transporting function and light-emitting function. The device is used in combination with compounds each having hole-transporting property, electron-transporting property, or light-emitting property as appropriate, thereby allowing a substantial increase in freedom of choice in material to be used. Further, various compounds having different emission wavelengths can be used, thereby allowing an increase in variety of luminescent colors. Further, luminous efficiency may be improved by efficiently trapping each carrier or exciton in the light emitting layer 3 provided in the middle of the device.

Figure 4:
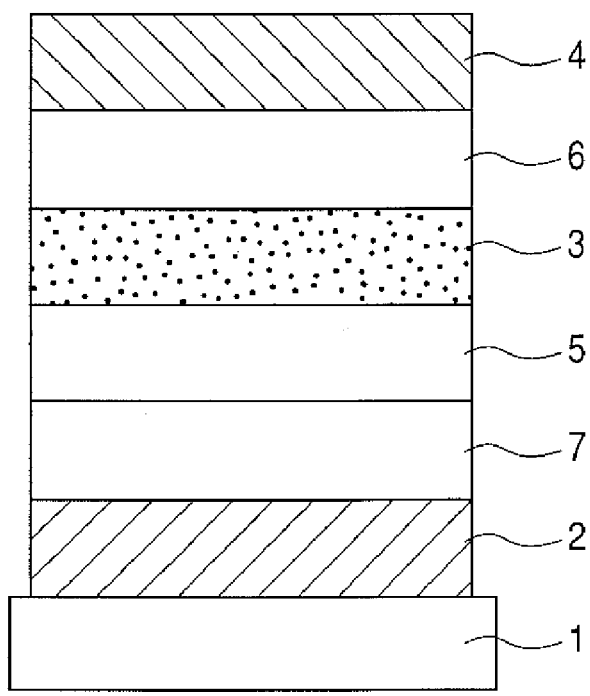
FIG. 4 is a sectional view illustrating yet another example of the organic light emitting device according to of the present invention.

FIG. 4 is a sectional view illustrating yet another example of the organic light emitting device according to the present invention. FIG. 4 has a structure illustrated in FIG. 3 except that a hole injecting layer 7 is inserted into a side of the anode 2. This structure is effective for improving adhesiveness between the anode 2 and the hole transporting layer 5 or for improving hole-injecting property, which is effective in lowering a voltage to be applied to the device.

Figure 5:
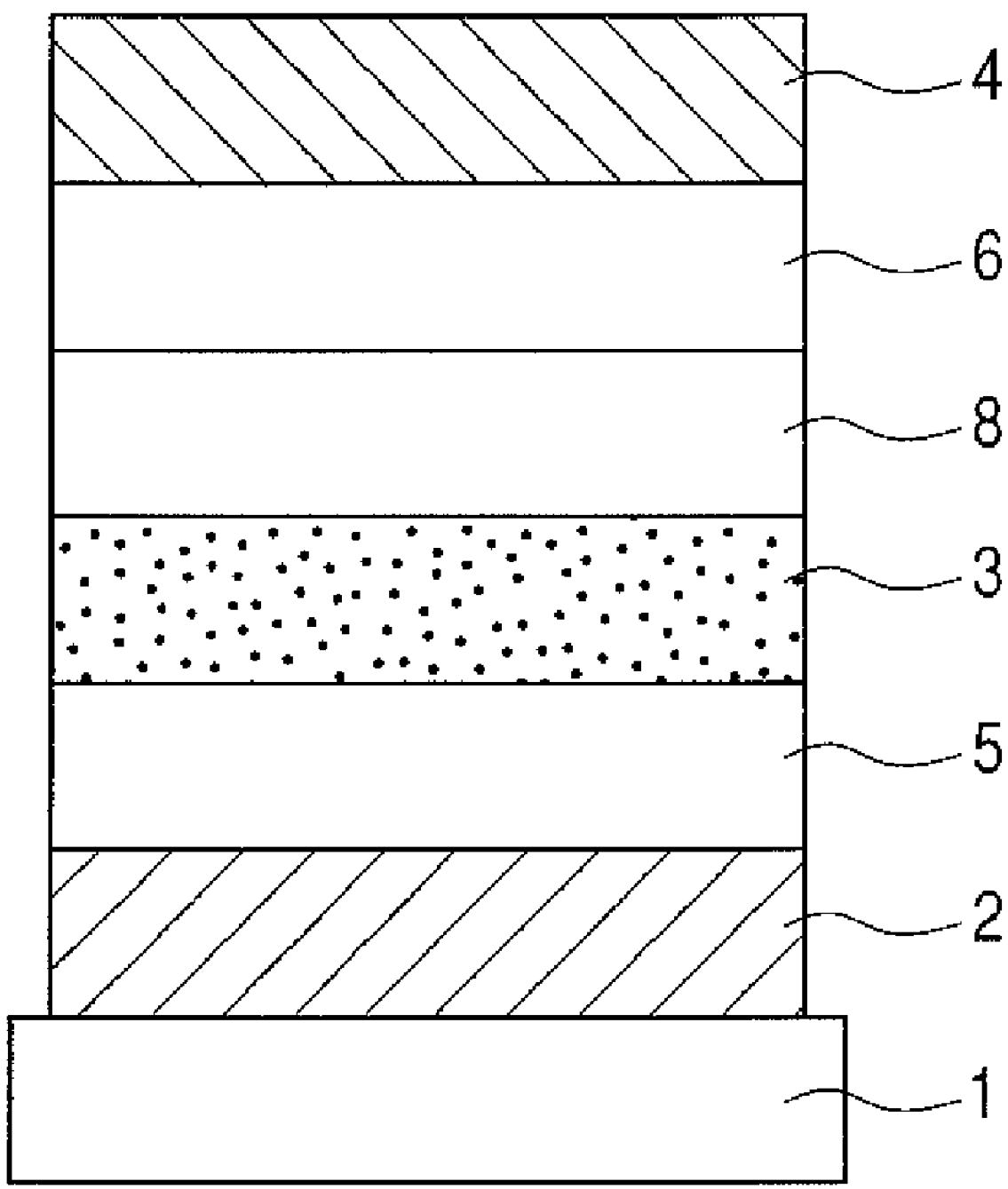
FIG. 5 is a sectional view illustrating still yet another example of the organic light emitting device according to the present invention.

FIG. 5 is a sectional view illustrating still yet another example of the organic light emitting device according to the present invention. FIG. 5 has a structure illustrated in FIG. 3 except that a layer (the hole/exciton blocking layer 8) for blocking travel of a hole or exciton to a side of the cathode 4 is inserted between the light emitting layer 3 and the electron transporting layer 6. This structure uses a compound having an extremely high ionization potential for the hole/exciton blocking layer 8 and is effective for improving luminous efficiency.

Note that FIGS. 1 to 5 each illustrate a basic device structure, and the structure of the organic light emitting device using the silyl compound of the present invention is not limited to the structures illustrated in FIGS. 1 to 5. For example, the organic light emitting device of the present invention may have any one of various layer structures including: a structure in which an insulating layer is provided at an interface between an electrode and an organic layer; a structure in which an adhesive or interference layer is provided; and a structure in which a hole transporting layer is formed of two layers with different ionization potentials.

The organic light emitting device of the present invention may be used for any one of the structures illustrated in FIGS. 1 to 5.

In particular, an organic layer using the silyl compound of the present invention is useful as a light emitting layer, an electron transporting layer, or a hole transporting layer. In addition, a layer formed by a vacuum vapor deposition method, a solution coating method, or the like is hardly crystallized and has excellent stability over time.

In the present invention, the silyl compound is used particularly as a component of the light emitting layer. In addition, a conventionally known additive compound such as a low-molecular-weight-based or polymer-based hole transportable compound, luminescent compound, or electron transportable compound can be used together as required. The load of any one of those compounds when the compound is used as a host material or an auxiliary dopant may be in the range of 0.01 wt % or more to less than 100 wt % with respect to the total of the components of the light emitting layer.

Examples of the compounds will be shown below.

A preferred hole injecting transporting material has excellent mobility for facilitating injection of a hole from an anode and for transporting the injected hole to a light emitting layer. Examples of a low molecular weight or polymer material having hole injecting transporting property include, but are not limited to: a triarylamine derivative; a phenylenediamine derivative; a triazole derivative; an oxadiazole derivative; an imidazole derivative; a pyrazoline derivative; a pyrazolone derivative; an oxazole derivative; a fluorenone derivative; a hydrazone derivative; a stilbene derivative; a phthalocyanine derivative; a porphyrin derivative; poly(vinylcarbazole); poly(silylene); poly(thiophene); and other conductive polymers.

Examples of a material which is mainly involved in a light-emitting function except the silyl compound to be used in the organic light emitting device of the present invention include, but are not limited to: a polycyclic condensed aromatic compound (including a naphthalene derivative, a phenanthrene derivative, a fluorene derivative, a pyrene derivative, a tetracene derivative, a coronene derivative, a chrysene derivative, a perylene derivative, a 9,10-diphenylanthracene derivative, or rubrene); a quinacridone derivative; an acridone derivative; a coumarin derivative; a pyran derivative; Nile red; a pyrazine derivative; a benzoimidazole derivative; a benzothiazole derivative; a benzoxazole derivative; a stilbene derivative; an organometallic complex (including: an organic aluminum complex such as tris(8-quinolinolato)aluminum; or an organic beryllium complex); and a polymer derivative (including a poly(phenylene vinylene) derivative, a poly(fluorene) derivative, a poly(phenylene) derivative, a poly(thienylene vinylene) derivative, or a poly(acetylene) derivative).

The electron injecting transporting material may be arbitrarily selected from materials which facilitate injection of an electron from a cathode and which have a function of transporting the injected electron into a light emitting layer. The material is selected in consideration of, for example, the balance with the mobility of a carrier of the hole transport material. Examples of a material having electron injecting transporting property include, but are not limited to, an oxadiazole derivative, an oxazole derivative, a thiazole derivative, a thiadiazole derivative, a pyrazine derivative, a triazole derivative, a triazine derivative, a perylene derivative, a quinoline derivative, a quinoxaline derivative, a fluorenone derivative, an anthrone derivative, a phenanthroline derivative, and an organometallic complex.

In the organic light emitting device according to the present invention, the layer containing the silyl compound of the present invention and layers containing other organic compounds are each formed by the following method. A thin film is generally formed by a vacuum vapor deposition method, an ionized evaporation method, sputtering, plasma, or a known coating method (such as a spin coating, dipping, casting, LB, or inkjet method) in which a compound is dissolved in an appropriate solvent. In film formation by a coating method, in particular, a film may be formed by using a compound in combination with an appropriate binder resin.

The binder resin may be selected from a wide variety of binder resins. Examples of the binder resin include, but not limited to: a polyvinyl carbazole resin; a polycarbonate resin; a polyester resin; a polyallylate resin; a polystyrene resin; an ABS resin; a polybutadine resin; a polyurethane resin; an acrylic resin; a methacrylic resin; a butyral resin; a polyvinyl acetal resin; a polyamide resin; a polyimide resin; a polyethylene resin; a polyethersulfone resin; a diallyl phthalate resin; a phenol resin; an epoxy resin; a silicone resin; a polysulfone resin; and a urea resin. One kind of binder resin may be used alone, or two or more kinds thereof may be mixed and used as a copolymer. Further, an additive such as a known plasticizer, antioxidant, or ultraviolet absorber may be used in combination as required.

An anode material may have as large a work function as possible, and examples thereof include: a metal element such as gold, platinum, silver, copper, nickel, palladium, cobalt, selenium, vanadium, or tungsten; an alloy thereof; and a metal oxide such as tin oxide, zinc oxide, indium oxide, indium tin oxide (ITO), or indium zinc oxide. Further, a conductive polymer such as polyaniline, polypyrrole, polythiophene, or polyphenylene sulfide may also be used. Each of those electrode materials may be used alone, or two or more kinds thereof may be used in combination. Further, the anode may have a single layer structure or a multilayer structure.

Meanwhile, a cathode material may have a small work function, and examples thereof include: a metal element such as lithium, sodium, potassium, calcium, magnesium, aluminum, indium, ruthenium, titanium, manganese, yttrium, silver, lead, tin, or chromium; and an alloy thereof such as a lithium-indium alloy, a sodium-potassium alloy, a magnesium-silver alloy, an aluminum-lithium alloy, an aluminum-magnesium alloy, or a magnesium-indium alloy. A metal oxide such as indium tin oxide (ITO) may also be used. Each of those electrode materials may be used alone, or two or more kinds thereof may be used in combination. Further, the cathode may have a single layer structure or a multilayer structure.

The substrate to be used in the present invention is not particularly limited, but examples thereof include: an opaque substrate such as a metallic substrate or a ceramics substrate; and a transparent substrate such as a glass substrate, a quartz substrate, or a plastic sheet substrate. In addition, the substrate may have a color filter film, a fluorescent color converting filter film, a dielectric reflection film, or the like for controlling luminescent color.

Further, a protective layer or a sealing layer may be formed on the produced device to prevent contact between the device and oxygen, moisture, or the like. Examples of the protective layer include: a diamond thin film; a film formed of an inorganic material such as metal oxide or metal nitride; a polymer film formed of a fluorine resin, polyparaxylene, polyethylene, a silicone resin, a polystyrene resin, or the like; and a photo-curable resin Further, the device itself may be covered with glass, an airtight film, a metal, or the like and packaged with an appropriate sealing resin.

A thin film transistor (TFT) may be produced on a substrate, and then the device of the present invention may be produced to be connected to TFT.

Regarding the emission direction of a device, the device may have a bottom emission structure (structure in which light is emitted from a substrate side) or a top emission structure (structure in which light is emitted from an opposite side of the substrate).

Hereinafter, the present invention will be described more specifically with reference to examples, but the present invention is not limited to the examples.

EXAMPLE 1

(Method of Producing Exemplified Compound No. 107)
(1) Synthesis of Intermediate 9-bromo-10-trimethylsilylanthracene Under an argon atmosphere, the temperature of a solution of 9,10-dibromoanthracene (5 g, 15 mmol) in dry-THF (50 ml) was cooled to −69° C., and t-butyllithium (18 mmol) was dropped to the solution. After the mixture had been stirred for 3 hours, chlorotrimethylsilane (3 ml, 22.5 mmol) was added to the mixture, and the whole was stirred at −69° C. for an additional 3 hours. After the temperature of the resultant had been increased to room temperature, the resultant was quenched with sodium bicarbonate water, extracted with toluene, and dried with sodium sulfate. Then, the solvent was removed by distillation. The residue was dispersed and washed with hexane, the insoluble matter was removed, and the filtrate was condensed. The condensate was washed with ethanol, and was then subjected to silica gel column chromatography, whereby 1 g of 9-bromo-10-trimethylsilylanthracene was obtained.

Figure 6:
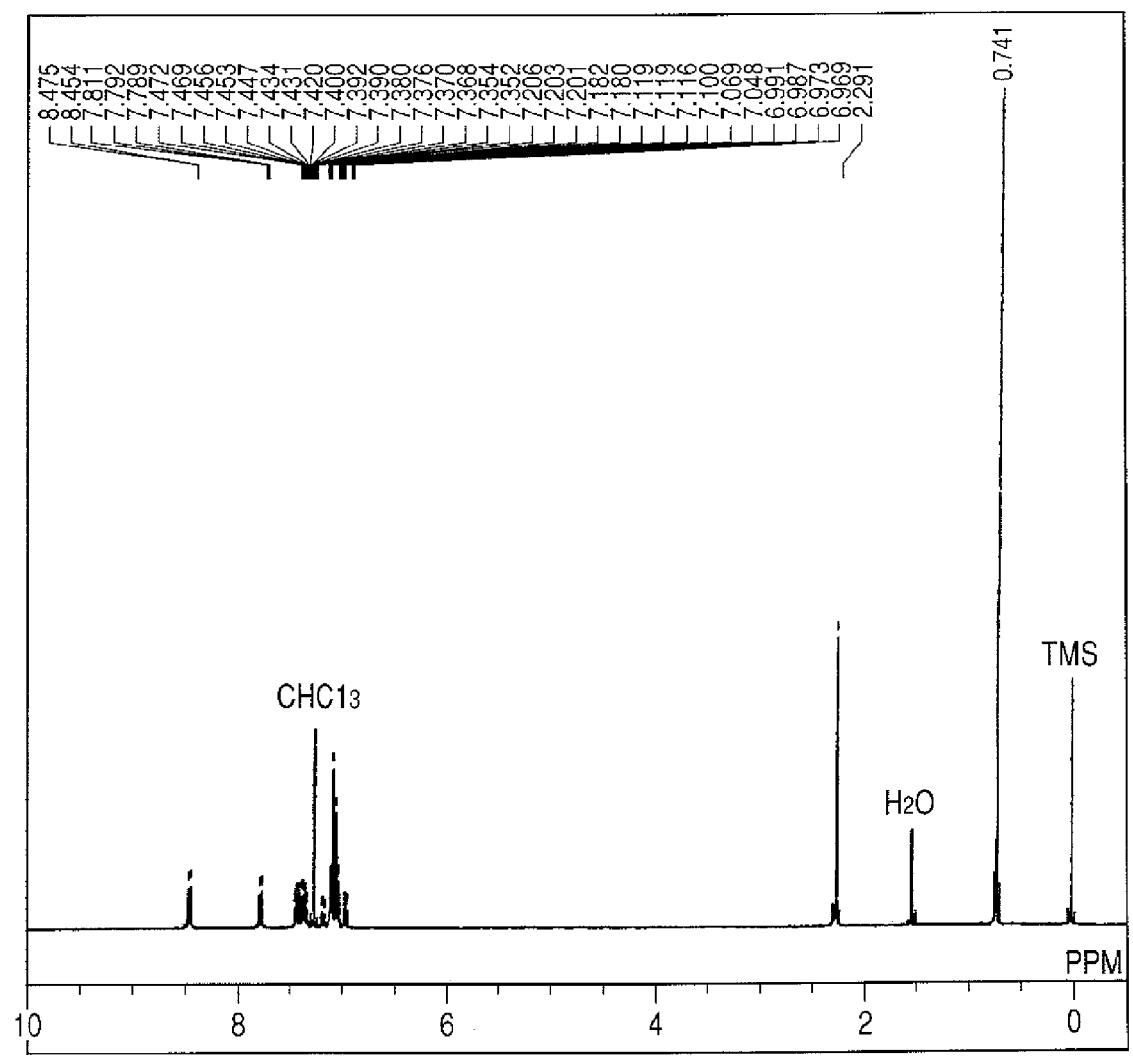
FIG. 6 is a view illustrating $^1$H-NMR spectrum of Exemplified Compound No. 107 obtained in Example 1.

(2) Synthesis of Exemplified Compound No. 107
Under a nitrogen atmosphere, 1.24 g (3.76 mmol) of 9-bromo-10-trimethylsilylanthracene and 1.5 g (3.76 mmol) of 2-[4-[di(4-methylphenyl)amino]phenyl]-4,4,5,5-tetramethyl-[1,3,2]dioxaborolane were dissolved in a mixed solvent of toluene (60 ml) and ethanol (60 ml). Further, an aqueous solution of sodium carbonate (9.40 mmol) was added to the mixture, and the whole was stirred at 50° C. for 30 minutes. Tetrakis(triphenylphosphine)palladium (87 mg, 0.075 mmol) was added to the resultant, and the whole was stirred at 80° C. for 3.5 hours under heat. After the temperature of the resultant had been cooled to room temperature, water and toluene were added to the resultant to separate an organic layer. After having been washed with a saturated salt solution, the organic layer was dried with sodium sulfate. The solvent was removed by distillation, and the residue was purified by means of silica gel column chromatography, whereby 0.68 g of Exemplified Compound No. 107 was obtained. FIG. 6 illustrates the $^1$H-NMR spectrum of Exemplified Compound No. 107 thus obtained.

EXAMPLES 2 TO 8

(Methods of Producing Exemplified Compounds No. 106 and 108 to 113)

Exemplified Compound No. 106 was synthesized in the same manner as in Example 1 except that chloro-tert-butyldimethylsilane was used instead of chlorotrimethylsilane. Exemplified Compound No. 108 was synthesized in the same manner as in Example 1 except that chloro-tert-butyldimethylsilane and 2-[3-[di(4-tert-butylphenyl)amino]-5-methylphenyl]-4,4,5,5-tetramethyl-[1,3,2]dioxaborolane were used instead of chlorotrimethylsilane and 2-[4-[di(4-methylphenyl)amino]phenyl]-4,4,5,5-tetramethyl-[1,3,2]dioxaborolane. Exemplified Compound No. 109 was synthesized in the same manner as in Example 1 except that chloro-tert-butyldimethylsilane and 2-[3-[di(4-tert-butylphenyl)amino]phenyl]-4,4,5,5-tetramethyl-[1,3,2]dioxaborolane were used instead of chlorotrimethylsilane and 2-[4-[di(4-methylphenyl)amino]phenyl]-4,4,5,5-tetramethyl-[1,3,2]dioxaborolane. Exemplified Compound No. 110 was synthesized in the same manner as in Example 1 except that chlorodimesitylmethylsilane and 2-[3-[di(4-tert-butylphenyl)amino]phenyl]-4,4,5,5-tetramethyl-[1,3,2]dioxaborolane were used instead of chlorotrimethylsilane and 2-[4-[di(4-methylphenyl)amino]phenyl]-4,4,5,5-tetramethyl-[1,3,2]dioxaborolane. Exemplified Compound No. 111 was synthesized in the same manner as in Example 1 except that chloro-i-propyldimethylsilane and 2-[3-[di(4-tert-butylphenyl)amino]pyridin-5-yl]-4,4,5,5-tetramethyl-[1,3,2] dioxaborolane were used instead of chlorotrimethylsilane and 2-[4-[di(4-methylphenyl)amino]phenyl]-4,4,5,5-tetramethyl-[1,3,2]dioxaborolane. Exemplified Compound No. 112 was synthesized in the same manner as in Example 1 except that chloro-tert-butyldimethylsilane and 2-[3-[N-[2-(9,9-dimethylfluorenyl)]-N-(4-tert-butylphenyl)amino]phenyl]-4,4,5,5-tetramethyl-[1,3,2]dioxaborolane were used instead of chlorotrimethylsilane and 2-[4-[di(4-methylphenyl)amino]phenyl]-4,4,5,5-tetramethyl-[1,3,2]dioxaborolane. Exemplified Compound No. 113 was synthesized in the same manner as in Example 1 except that chloro-tert-butyldimethylsilane and 2-[2-(di-p-tolylamino)thiophen-5-yl]-4,4,5,5-tetramethyl-[1,3,2]dioxaborolane were used instead of chlorotrimethylsilane and 2-[4-[di(4-methylphenyl)amino]phenyl]-4,4,5,5-tetramethyl-[1,3,2]dioxaborolane.

EXAMPLE 9

(Method of Producing Exemplified Compound No. 118)
Exemplified Compound No. 118 was synthesized in the same manner as in Example 1 except that 2,3,6,7-tetramethyl-9,10-dibromoanthracene was used instead of 9,10-dibromoanthracene.

EXAMPLE 10

(Method of Producing Exemplified Compound No. 134)
(1) Synthesis of Intermediate 9-bromo-10-(tert-butyldimethylsilyl)anthracene
A 9-bromo-10-(tert-butyldimethylsilyl)anthracene intermediate was synthesized in the same manner as in Example 1 except that chloro-tert-butyldimethylsilane was used instead of chlorotrimethylsilane.
(2) Synthesis of Exemplified Compound No. 134
Under a nitrogen atmosphere, 1.40 g (3.76 mmol) of 9-bromo-10-(tert-butyldimethylsilyl)anthracene and 1.28 g (3.76 mmol) of 2-(7-tert-butyl-3-methylpyren-1-yl)-4,4,5,5-tetramethyl-[1,3,2]dioxaborolane were dissolved in a mixed solvent of toluene (60 ml) and ethanol (60 ml). Further, an aqueous solution of sodium carbonate (9.40 mmol) was added to the mixture, and the whole was stirred at 50° C. for 30 minutes. Tetrakis(triphenylphosphine)palladium (87 mg, 0.075 mmol) was added to the resultant, and the whole was stirred at 80° C. for 5 hours under heat. After the temperature of the resultant had been cooled to room temperature, water and toluene were added to the resultant to separate an organic layer. After having been washed with a saturated salt solution, the organic layer was dried with sodium sulfate. The solvent was removed by distillation, and the residue was purified by means of silica gel column chromatography, whereby 0.91 g of Exemplified Compound No. 134 was obtained.

EXAMPLES 11 TO 21

(Methods of Producing Exemplified Compounds No. 122, 124 to 126, 128, 132, 133, 135, 136, and 139)
Exemplified Compound No. 122 was synthesized in the same manner as in Example 10 except that 2-(naphthalen-2-yl)-4,4,5,5-tetramethyl-[1,3,2]dioxaborolane was used instead of 2-(7-tert-butyl-3-methylpyren-1-yl)-4,4,5,5-tetramethyl-[1,3,2]dioxaborolane in Example 10. Exemplified Compound No. 124 was synthesized in the same manner as in Example 10 except that 2-(phenanthren-9-yl)-4,4,5,5-tetramethyl-[1,3,2]dioxaborolane was used instead of 2-(7-tert-butyl-3-methylpyren-1-yl)-4,4,5,5-tetramethyl-[1,3,2] dioxaborolane in Example 10. Exemplified Compound No. 125 was synthesized in the same manner as in Example 10 except that 3-phenanthrene-4,4,5,5-tetramethyl-[1,3,2]dioxaborolane was used instead of 2-(7-tert-butyl-3-methylpyren-1-yl)-4,4,5,5-tetramethyl-[1,3,2]dioxaborolane in Example 10. Exemplified Compound No. 126 was synthesized in the same manner as in Example 10 except that 1-pyrene-d9-4,4,5,5-tetramethyl-[1,3,2]dioxaborolane was used instead of 2-(7-tert-butyl-3-methylpyren-1-yl)-4,4,5,5-tetramethyl-[1,3,2]dioxaborolane in Example 10. Exemplified Compound No. 128 was synthesized in the same manner as in Example 10 except that 3-fluoranthene-4,4,5,5-tetramethyl-[1,3,2]dioxaborolane was used instead of 2-(7-tert-butyl-3-methylpyren-1-yl)-4,4,5,5-tetramethyl-[1,3,2]dioxaborolane in Example 10. Exemplified Compound No. 132 was synthesized in the same manner as in Example 10 except that 2-(pyren-4-yl)-4,4,5,5-tetramethyl-[1,3,2]dioxaborolane was used instead of 2-(7-tert-butyl-3-methylpyren-1-yl)-4,4,5,5-tetramethyl-[1,3,2]dioxaborolane in Example 10. Exemplified Compound No. 133 was synthesized in the same manner as in Example 10 except that 2-(7-tert-butylpyren-1-yl)-4,4,5,5-tetramethyl-[1,3,2]dioxaborolane was used instead of 2-(7-tert-butyl-3-methylpyren-1-yl)-4,4,5,5-tetramethyl-[1,3,2]dioxaborolane in Example 10. Exemplified Compound No. 135 was synthesized in the same manner as in Example 10 except that 2-(2,7-di-tert-butylpyren-4-yl)-4,4,5,5-tetramethyl-[1,3,2] dioxaborolane was used instead of 2-(7-tert-butyl-3-methylpyren-1-yl)-4,4,5,5-tetramethyl-[1,3,2]dioxaborolane in Example 10. Exemplified Compound No. 136 was synthesized in the same manner as in Example 10 except that 2-(quinolin-6-yl)-4,4,5,5-tetramethyl-[1,3,2]dioxaborolane was used instead of 2-(7-tert-butyl-3-methylpyren-1-yl)-4,4,5,5-tetramethyl-[1,3,2]dioxaborolane in Example 10. Exemplified Compound No. 139 was synthesized in the same manner as in Example 10 except that 2-(dibenzo[b,d]furan-2-yl)-4,4,5,5-tetramethyl-[1,3,2]dioxaborolane was used instead of 2-(7-tert-butyl-3-methylpyren-1-yl)-4,4,5,5-tetramethyl-[1,3,2]dioxaborolane in Example 10.

EXAMPLE 22

An organic light emitting device having the structure illustrated in FIG. 3 was produced by the method described below.

Indium tin oxide (ITO) as the anode 2 was formed as a film having a thickness of 120 nm on a glass substrate as the substrate 1 by a sputtering method, and the resultant was used as a transparent conductive supporting substrate. The resultant substrate was subjected to ultrasonic cleaning in acetone and isopropyl alcohol (IPA) in this order. Then, the substrate was washed in boiling IPA and dried. The substrate was further subjected to UV/ozone cleaning to be used as a transparent conductive supporting substrate.

A chloroform solution containing 0.2 wt % of a compound represented by the following structural formula as a hole transport material was prepared.

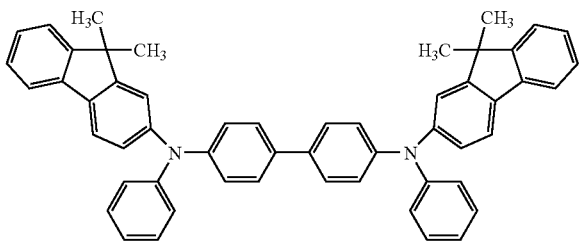

This solution was dropped onto the above-mentioned ITO electrode and formed into a film on the ITO electrode through spin coating at a revolving speed of 500 rpm for 10 seconds at first and then at a revolving speed of 1,000 rpm for 1 minute. Then, the whole was placed in a vacuum oven at 80° C. and dried for 10 minutes, to thereby completely remove the solvent in the thin film. The thus-formed hole transporting layer 5 had a thickness of 25 nm.

Next, as the light emitting layer 3, Exemplified Compound No. 109 described above was vapor-deposited on the hole transporting layer 5. The resultant light emitting layer 3 had a thickness of 20 nm. A degree of vacuum during vapor deposition was $1.0 \times 10^{-4}$ Pa and a film formation rate was 0.2 to 0.3 nm/second.

Further, as the electron transporting layer 6, 2,9-[2-(9,9'-dimethylfluorenyl)]-1,10-phenanthroline was formed into a film having a thickness of 50 nm through a vacuum vapor deposition method. A degree of vacuum during vapor deposition was $1.0 \times 10^{-4}$ Pa and a film formation rate was 0.2 to 0.3 nm/second.

Next, aluminum lithium (AlLi) was formed into a film having a thickness of 0.5 nm on the electron transporting layer 6 by a vacuum vapor deposition method, and an aluminum film having a thickness of 150 nm was formed thereon through a vacuum vapor deposition method, to thereby produce an electron injecting electrode (cathode 4). As a result, an organic light emitting device with the electron injecting electrode (cathode 4) was produced. A degree of vacuum during vapor deposition was $1.0 \times 10^{-4}$ Pa. According to the condition of formation, a lithium fluoride film formation rate was 0.05 nm/second, and an aluminum film formation rate was 1.0 to 1.2 nm/second. The obtained organic EL device was covered with a protective glass and sealed with an acrylic resin binder in a dry air atmosphere to prevent degradation of the device by adsorption of moisture thereon.

Under application of a voltage of 4 V to the thus-obtained organic light emitting device having the ITO electrode (anode 2) as a positive electrode and the Al electrode (cathode 4) as a negative electrode, blue light emission with an emission luminance of 190 cd/m² and luminous efficiency of 1.9 lm/W was observed.

Further, the voltage was applied to the device for 100 hours while a current density was maintained at 30 mA/cm² in a nitrogen atmosphere, resulting in slight luminance degradation from an initial luminance of 300 cd/m² to a luminance of 230 cd/m² after 100 hours.

EXAMPLES 23 TO 27

Organic light emitting devices were produced in the same manner as in Example 22 and were subjected to the same evaluation except that the compounds shown in Table 1 were used instead of Exemplified Compound No. 109. Table 1 shows the results.

TABLE 1

| Example | Exemplified Compound No. | Applied voltage (V) | Luminance (cd/m²) | Efficiency (lm/W) |
|---|---|---|---|---|
| 23 | 102 | 4.0 | 420 | 6.5 |
| 24 | 112 | 4.0 | 240 | 2.1 |
| 25 | 128 | 4.0 | 240 | 2.4 |
| 26 | 134 | 4.0 | 300 | 2.8 |
| 27 | 147 | 4.0 | 230 | 2.8 |

COMPARATIVE EXAMPLE 1

An organic light emitting device was produced in the same manner as in Example 1 and was subjected to the same evaluation except that the following Comparative Compound 1 was used instead of Exemplified Compound No. 109.

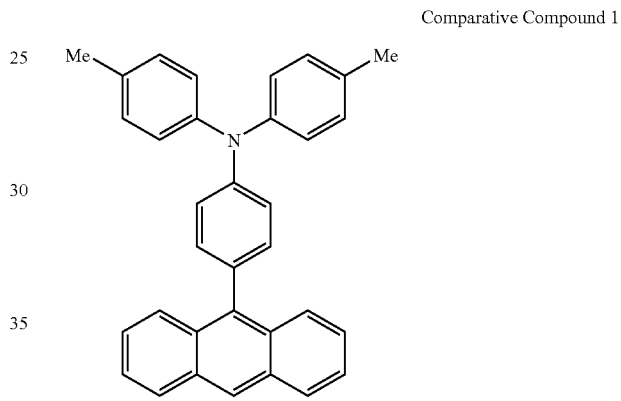

Comparative Compound 1

Under application of a voltage of 4 V, blue light emission with an emission luminance of 70 cd/m² and a luminous efficiency of 1.4 lm/W was observed. Further, when the voltage was applied to the device for 100 hours while a current density was maintained at 30 mA/cm² in a nitrogen atmosphere, a luminance change from an initial luminance of 110 cd/m² to a luminance of 53 cd/m² after 100 hours was observed.

EXAMPLES 28 TO 45

Next, devices were each produced in the same manner as in Example 1 except that a first compound shown in Table 2 as a dopant material and a second compound shown in Table 2 as a host material were co-vapor-deposited to provide a light emitting layer having a thickness of 20 nm as the light emitting layer 3. The devices were each evaluated in the same manner as in Example 1. Table 2 shows the results.

In addition, a voltage was applied to the device produced in Example 31 for 100 hours under a nitrogen atmosphere while a current density was kept at 30 mA/cm². As a result, an initial luminance of 590 cd/m² reduced to 475 cd/m² in 100 hours. This result means that luminance deterioration was small.

TABLE 2

| Example | First compound No. | Second compound No. | Co-vapor deposition ratio Compound 1:Compound 2 | Applied voltage (V) | Luminance (cd/m$^2$) | Efficiency (lm/W) |
|---|---|---|---|---|---|---|
| 28 | 102 | 201 | 20:80 | 4.0 | 1420 | 10.2 |
| 29 | 109 | 202 | 15:85 | 4.0 | 390 | 3.8 |
| 30 | 107 | 208 | 15:85 | 4.0 | 380 | 3.7 |
| 31 | 118 | 201 | 15:85 | 4.0 | 420 | 3.6 |
| 32 | 128 | 201 | 10:90 | 4.0 | 420 | 3.3 |
| 33 | 133 | 201 | 15:85 | 4.0 | 560 | 4.0 |
| 34 | 135 | 201 | 15:85 | 4.0 | 430 | 3.4 |
| 35 | 147 | 201 | 10:90 | 4.0 | 570 | 4.5 |
| 36 | 106 | 301 | 15:85 | 4.0 | 300 | 3.4 |
| 37 | 110 | 301 | 10:90 | 4.0 | 220 | 2.8 |
| 38 | 116 | 301 | 15:85 | 4.0 | 250 | 2.9 |
| 39 | 133 | 307 | 10:90 | 4.0 | 530 | 3.8 |
| 40 | 109 | 450 | 15:85 | 4.0 | 430 | 3.4 |
| 41 | 107 | 407 | 10:90 | 4.0 | 300 | 2.9 |
| 42 | 134 | 402 | 15:85 | 4.0 | 530 | 3.8 |
| 43 | 124 | 504 | 15:85 | 4.0 | 220 | 2.4 |
| 44 | 128 | 514 | 15:85 | 4.0 | 480 | 3.4 |
| 45 | 143 | 512 | 15:85 | 4.0 | 580 | 3.8 |

COMPARATIVE EXAMPLE 2

A device was produced in the same manner as in Example 30 except that: Comparative Compound 1 was used as a first compound instead of Exemplified Compound No. 109; and a co-vapor-deposition ratio was changed to 20:80 (weight ratio). The device was evaluated in the same manner as in Example 30.

Under application of a voltage of 4 V, blue light emission with an emission luminance of 200 cd/m$^2$ and a luminous efficiency of 1.8 lm/W was observed. Further, when the voltage was applied to the device for 100 hours while a current density was maintained at 30 mA/cm$^2$ in a nitrogen atmosphere, a luminance change from an initial luminance of 310 cd/m$^2$ to a luminance of 145 cd/m$^2$ after 100 hours was observed.

The silyl compound of the present invention in which a silyl group is directly bonded to an anthracene ring can be utilized in an organic light emitting device because the incorporation of the compound particularly into a light emitting layer can provide highly efficient light emission.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims priority from Japanese Patent Application No. 2006-056958 filed on Mar. 2, 2006, which is hereby incorporated by reference herein.

What is claimed is:

1. A silyl compound represented by the following general formula (1):

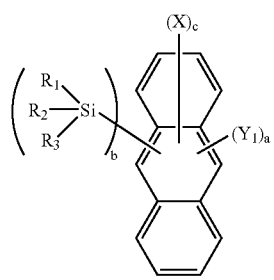

[1]

wherein $R_1$, $R_2$, and $R_3$ each represent a group selected from the group consisting of a hydrogen atom, a halogen atom, a substituted or unsubstituted alkyl group, a substituted or unsubstituted aralkyl group, a substituted or unsubstituted aryl group, and a substituted or unsubstituted heterocyclic group, and may be identical to or different from one another, X represents a group selected from the group consisting of a halogen atom, a substituted or unsubstituted alkyl group, a substituted or unsubstituted aralkyl group, a substituted or unsubstituted alkenyl group, a substituted or unsubstituted alkynyl group, a substituted or unsubstituted alkoxy group, a substituted or unsubstituted sulfide group, a substituted or unsubstituted silyl group, a substituted or unsubstituted amino group, a substituted or unsubstituted aryl group, and a substituted or unsubstituted heterocyclic group, and X's may be identical to or different from each other, $Y_1$ is represented by the following general formula (3):

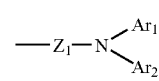

[3]

wherein $Z_1$ represents a group selected from the group consisting of an arylene group and a divalent heterocyclic group, $Ar_1$ and $Ar_2$ each represent a group selected from the group consisting of a substituted or unsubstituted alkyl group, a substituted or unsubstituted aralkyl group, a substituted or unsubstituted aryl group, and a substituted or unsubstituted heterocyclic group, and $Ar_1$ and $Ar_2$ may be identical to or different from each other, and furthermore, when X represents a substituted or unsubstituted silyl group, X substitutes at any one of 1- to 8-positions of the anthracene ring except a substitution site of the $R_1R_2R_3Si$— group, a represents an integer of 1 or more to 3 or less, b represents an integer of 1 or more to 3 or less, and c represents an integer of 0 or more to 8 or less provided that a relationship of a+b+c≦10 is established.

2. A silyl compound represented by the following general formula (2):

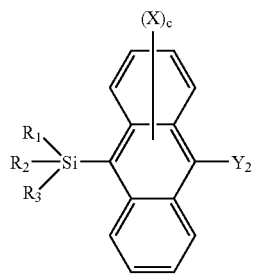

wherein $R_1$, $R_2$, and $R_3$ each represent a group selected from the group consisting of a hydrogen atom, a halogen atom, a substituted or unsubstituted alkyl group, a substituted or unsubstituted aralkyl group, a substituted or unsubstituted aryl group, and a substituted or unsubstituted heterocyclic group, and may be identical to or different from one another, X represents a group selected from the group consisting of a halogen atom, a substituted or unsubstituted alkyl group, a substituted or unsubstituted aralkyl group, a substituted or unsubstituted alkenyl group, a substituted or unsubstituted alkynyl group, a substituted or unsubstituted alkoxy group, a substituted or unsubstituted sulfide group, a substituted or unsubstituted silyl group, a substituted or unsubstituted amino group, a substituted or unsubstituted aryl group, and a substituted or unsubstituted heterocyclic group, and X's may be identical to or different from each other, $Y_2$ is represented by the following general formula (3):

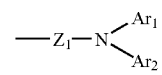

wherein $Z_1$ represents a group selected from the group consisting of an arylene group and a divalent heterocyclic group, $Ar_1$ and $Ar_2$ each represent a group selected from the group consisting of a substituted or unsubstituted alkyl group, a substituted or unsubstituted aralkyl group, a substituted or unsubstituted aryl group, and a substituted or unsubstituted heterocyclic group, and $Ar_1$ and $Ar_2$ may be identical to or different from each other and c represents an integer of 0 or more to 8 or less.

* * * * *

UNITED STATES PATENT AND TRADEMARK OFFICE
CERTIFICATE OF CORRECTION

PATENT NO. : 7,365,198 B2 Page 1 of 1
APPLICATION NO. : 11/677925
DATED : April 29, 2008
INVENTOR(S) : Akihito Saitoh et al.

It is certified that error appears in the above-identified patent and that said Letters Patent is hereby corrected as shown below:

ON COVER PAGE AT (56) FOREIGN PATENT DOCUMENTS

"2004103463" should read --2004-103463--.

COLUMN 3

Lines 15-18, " —$Z_1$—N(Ar/Ar) " should read -- —$Z_1$—N($Ar_1$/$Ar_2$) --.

COLUMN 4

Lines 40-43, " —$Z_1$—N(Ar/Ar) " should read -- —$Z_1$—N($Ar_1$/$Ar_2$) --.

COLUMN 6

Line 5, "$Ar_3$" should read --$Ar_3$ and--.

COLUMN 14

Lines 27-30, " —$Z_1$—N(Ar/Ar) " should read -- —$Z_1$—N($Ar_1$/$Ar_2$) --.

Signed and Sealed this

Twenty-fourth Day of February, 2009

JOHN DOLL
*Acting Director of the United States Patent and Trademark Office*